US007892730B2

(12) United States Patent
Morris et al.

(10) Patent No.: US 7,892,730 B2
(45) Date of Patent: Feb. 22, 2011

(54) COMPOSITIONS AND METHODS FOR CANCER

(75) Inventors: David W. Morris, Davis, CA (US); Eric K. Engelhard, Davis, CA (US)

(73) Assignee: Sagres Discovery, Inc., Emeryville, CA (US)

( * ) Notice: Subject to any disclaimer, the term of this patent is extended or adjusted under 35 U.S.C. 154(b) by 2350 days.

(21) Appl. No.: 10/087,192

(22) Filed: Mar. 1, 2002

(65) Prior Publication Data

US 2002/0182586 A1 Dec. 5, 2002

Related U.S. Application Data

(63) Continuation of application No. 09/747,377, filed on Dec. 22, 2000, now abandoned, and a continuation of application No. 09/798,586, filed on Mar. 2, 2001, now abandoned.

(51) Int. Cl.
C12Q 1/00 (2006.01)
C12Q 1/68 (2006.01)
G01N 1/00 (2006.01)
G01N 33/48 (2006.01)
G01N 33/53 (2006.01)
G01N 33/567 (2006.01)
G01N 33/574 (2006.01)

(52) U.S. Cl. .................. 435/6; 435/4; 435/7.1; 435/7.21; 435/7.23; 436/63; 436/64; 436/174

(58) Field of Classification Search ............ 435/4, 435/6, 7.1, 7.21, 7.23; 436/63, 64, 174
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,469,863 A | 9/1984 | Ts'o et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,816,567 A | 3/1989 | Cabilly et al. | |
| 5,034,506 A | 7/1991 | Summerton et al. | |
| 5,124,246 A | 6/1992 | Urdea et al. | |
| 5,216,141 A | 6/1993 | Benner | |
| 5,235,033 A | 8/1993 | Summerton et al. | |
| 5,359,100 A | 10/1994 | Urdea et al. | |
| 5,360,733 A | 11/1994 | Fukuda et al. | |
| 5,386,023 A | 1/1995 | Sanghvi et al. | |
| 5,445,934 A | 8/1995 | Fodor et al. | |
| 5,545,730 A | 8/1996 | Urdea et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,571,670 A | 11/1996 | Urdea et al. | |
| 5,580,731 A | 12/1996 | Chang et al. | |
| 5,591,584 A | 1/1997 | Chang et al. | |
| 5,594,117 A | 1/1997 | Urdea et al. | |
| 5,594,118 A | 1/1997 | Urdea et al. | |
| 5,597,909 A | 1/1997 | Urdea et al. | |
| 5,602,240 A | 2/1997 | De Mesmaeker et al. | |
| 5,624,802 A | 4/1997 | Urdea et al. | |
| 5,625,126 A | 4/1997 | Lonberg et al. | |
| 5,633,425 A | 5/1997 | Lonberg et al. | |
| 5,635,352 A | 6/1997 | Urdea et al. | |
| 5,637,684 A | 6/1997 | Cook et al. | |
| 5,644,048 A | 7/1997 | Yau | |
| 5,661,016 A | 8/1997 | Lonberg et al. | |
| 5,681,697 A | 10/1997 | Urdea et al. | |
| 5,681,702 A | 10/1997 | Collins et al. | |
| 5,700,637 A | 12/1997 | Southern | |
| 5,759,776 A | 6/1998 | Smith et al. | |
| 5,776,683 A | 7/1998 | Smith et al. | |
| 5,928,870 A | 7/1999 | Lapidus et al. | |
| 6,074,825 A | 6/2000 | Rundell et al. | |
| 6,153,441 A | 11/2000 | Appelbaum et al. | |

FOREIGN PATENT DOCUMENTS

| | | |
|---|---|---|
| WO | WO 87/05330 | 9/1987 |
| WO | WO 90/10448 | 9/1990 |
| WO | WO 91/04753 | 4/1991 |
| WO | WO 93/22443 | 11/1993 |
| WO | WO 95/25116 | 9/1995 |
| WO | WO 95/28490 | 10/1995 |
| WO | WO 95/35505 | 12/1995 |

(Continued)

OTHER PUBLICATIONS

Topalovski et al. Lymphoma of the breast. A clinicopathologic study of primary and secondary cases. Arch. Pathol. Lab Med. 123: 1208-1218, Dec. 1999.*

(Continued)

Primary Examiner—Alana M. Harris
(74) Attorney, Agent, or Firm—David A. Carpenter; Astrid Spain

(57) ABSTRACT

The present invention relates to novel sequences for use in diagnosis and treatment of carcinomas, especially lymphoma carcinomas. In addition, the present invention describes the use of novel compositions for use in screening methods.

19 Claims, No Drawings

FOREIGN PATENT DOCUMENTS

| | | |
|---|---|---|
| WO | WO 97/27212 | 7/1997 |
| WO | WO 97/27213 | 7/1997 |
| WO | WO 01/57182 | 8/2001 |
| WO | WO 01/94629 | 12/2001 |
| WO | WO 02/22660 | 3/2002 |
| WO | WO 03/008583 | 1/2003 |

OTHER PUBLICATIONS

Aguilera et al. T-cell lymphoma presenting in the breast: a histologic, immunophenotypic and molecular genetic study of four cases. Mod. Pathol. 13(6): 599-604, 2000.*

Database GeneCore Accession No. U78076, created on May 14, 1999, last visited on Oct. 24, 2004. Lee et al. "Cloning of Mouse Sepiapterin Reductase Gene and Characterization of its promoter Region," Gene Sequence, *Biochim Biophys Acta* (1999). vol. 1445, No. 1 pp. 165-171. MPSRCH Search Report 2004, 1 page.

International Search Report mailed on Nov. 10, 2004 for PCT patent application No. PCT/US02/41414 filed Dec. 26, 2002, 8 pages.

Allen, J. D. and Berns, A. (1996). "Complementation Tagging of Cooperating Oncogenes in Knockout Mice," *Cancer Biology* 7:299-306.

Altschul, S. F. and Gish, W. (1996). "Local Alignment Statistics" In *Methods in Enzymology* vol. 266, Academic Press, Inc., pp. 460-480.

Altschul, S. F. et al. (1990). "Basic Local Alignment Search Tool," *J. Mol. Biol.* 215:403-410.

Aplin, J. D. and Wriston, Jr., J. C. (1981). "Preparation, Properties, and Applications of Carbohydrate Conjugates of Proteins and Lipids," *CRC Crit. Rev. Biochem.* pp. 259-306.

Arenberg, D. A. et al. (2001). "The Murine CC Chemokine, 6C-Kine, Inhibits Tumor Growth and Angiogenesis in a Human Lung Cancer SCID Mouse Model," *Cancer Immunol. Immunother.* 49:587-592.

Ausubel, F. M. et al., eds. (1992). *Short Protocols in Molecular Biology*. Greene Publishing Associates and John Wiley & Sons, pp. iii-xviii (Table of Contents Only).

Bai, J. et al. (1999). "Sequence Comparison of JSRV with Endogenous Proviruses: Envelope Genotypes and a Novel ORF With Similarity to a G-Protein-Coupled Receptor," *Virology* 258:333-343.

Beaucage, S. L. and Iyer, R. P. (1993). "The Functionalization of Oligonucleotides Via Phosphoramidite Derivatives," *Tetrahedron* 49(10):1925-1963.

Boener, P. et al. (1991). "Production of Antigen-Specific Human Monoclonal Antibodies from in Vitro-Primed Human Splenocytes," *J. Immunol.* 147(1):86-95.

Bolli. M. et al. (1994). "α-Bicyclo-DNA: Synthesis, Characterization, and Pairing Properties of α-DNA-Analogues with Restricted Conformational Flexibility in the Sugar-Phosphate Backbone," Chapter 7 In *Carbohydrate Modifications in Antisense Research*. ACS Symposium Series 580, Shanghvi, Y. S and Cook, P. D, eds, American Chemical Society, Washington, pp. 100-117.

Brill, W. et al. (1989). "Synthesis of Oligodeoxynucleoside Phosphoridithioates via Thioamidites," *J. Am Chem soc.* 111:2321-2322.

Brower, V. (1998). "Naked DNA Vaccines Come of Age," *Nature Biotechnology* 16:1304-1305.

Carlsson, C. et al. (1996). "Screening for Genetic Mutations," *Nature* 380:207 (1 page total).

Cole, S.P.C., et al. (1985). "The EBV-Hybridoma Technique and Its Application to Human Lung Cancer," In *Monoclonal Antibodies and Cancer Therapy*, Reisfeld, R. A. and Sell, S., ed., Alan R. Liss, New York, p. 77-96 (Includes Table of Contents).

Creighton, T. E., ed. (1983). "Posttranslational Covalent Modifications of Polypeptide Chains," Chapter 2.4 In *Proteins: Structure and Molecular Properties*. W. H. Freeman & Co., San Francisco pp. 78-86 (Includes Table of Contents).

David, G. S. and Reisfeld, R. A. (1974). "Protein Iodination with Solid State Lactoperoxidase," *Biochemistry* 13(5):1014-1021.

De Mesmaeker, A. et al. (1994). "Comparison of Rigid and Flexible Backbones in Antisense Oligonucleotides," *Bioorganic & Medicinal Chem. Lett.* 4(3):395-398.

De Mesmaeker, A. et al. (1994). "Novel Backbone Replacements for Oligonucleotides," Chapter 2 In *Carbohydrate Modifications in Antisense Research*, ACS Symposium Series 580 . . . Shanghvi, Y. S Cook, P. D, eds, American Chemical Society, Washington, pp. 24-39.

Dempcy, R. O. et al. (1995). "Synthesis of a Thymidyl Pentamer of Deoxyribonucleic Guanidine and Binding Studies with DNA Homopolynucleotides," *Proc. Natl Acad. Sci. USA* 92:6097-6101.

Desbois, C. et al. (1996). "Exclusion of *Int*-6 from PML Nuclear Bodies by Binding to the HTLV-1 Tax Oncoprotein," *Science* 273:951-953.

Devereux et al. (1984). "A Comprehensive Set of Sequence Analysis Programs for the VAX," *Nuc. Acid. Res.* 12(1):387-395.

Doudney, K. et al. (2001). "Comparative Physical and Transcript Maps of~1 Mb around *looptail*, a Gene for Severe Neural Tube Defects on Distal Mouse Chromosome 1 and Human Chromosome 1q22-q23," *Genomics* 72(2):180-192.

Eckstein. F., ed. (1991). *Oligonucleotides and Analogues: A Practical Approach*, Oxford University Press, vii-xvii. (Table of Contents Only).

Edge, A. S. B. et al. (1981). "Deglycosylation of Glycoproteins by Trifluoromerathneusulfonic Acid," *Anal. Biochem.* 118:131-137.

Egholm, M. (1993). "PNA Hybridizes to Complementary Oligonucleotides Obeying the Watson-Crick Hydrogenbonding," *Nature* 365:566-568.

Elgholm, M. et al. (1992). "Peptide Nucleic Acids (PNA). Oligonucleotide Analogues with an Achiral Peptide Backbone," *J. Am. Chem. Soc.* 114:1895-1897.

Erny, K. M. et al. (1996). "Involvement of the *Tpl-2/cot* Oncogene in MMTV Turmorigenesis," *Oncogene* 13:2015-2020.

Evan, G. I. et al. (1985). "Isolation of Monoclonal Antibodies Specific for Human c-myc Proto-Oncogene Product," *Biology* 5(12):3610-3616.

Fan, L. et al. (2000). "Cutting Edge: Ectopic Expression of the Chemokine TCA4/SLC is Sufficient to Trigger Lymphoid Neogenesis,"*J. Immunol.* 164(8):3955-3959.

Feng, D. F. & Doolittle, R. F. (1987). "Progressive Sequence Alignment as a Prerequisite to Correct Phylogenetic Trees," *J. Mol. Evol.* 25:351-360.

Field, J. et al. (1988). "Purification of a RAS-Responsive Adenylyl Cyclase Complex from *Saccharomyces cerevisiae* by Use of a Epitope Addition Method," *Mol Cell. Biol.* 8(5):2159-2165.

Fishwild, D. M.et al. (1996). "High-Avidity Human IgGk Monoclonal Antibodies from a Novel Strain of Minilocus Transgenic Mice," *Nature Biotechnology* 14:845-851.

Gallahan, D. and Callahan, R. (1987). "Mammary Tumorigenesis in Feral Mice: Identification of a New *int* Locus in Mouse Mammary Tumor Virus (Czech II)-Induced Mammary Tumors," *J. Virol.* 61(1):66-74.

Gao, X. and Jeffs, W. P. (1994). "Unusual Conformation of a 3'-thioformacetal Linkage in a DNA Duplex," *J. Biomolecular NMR* 4:17-34.

Germer, S. et al. (2000). "High-Throughput SNP Allele-Frequency Determination in Pooled DNA Samples by Kinetic PCR," *Genome Res.* 10:258-266.

Goding, J. W. (1986). "Production of Monoclonal Antibodies," Chapter 3 In *Monoclonal Antibodies: Principles and Practice*, Academic Press, Inc., $2^{nd}$ edition, pp. 59-103.

Hansen, G. M. et al. (2000), "Genetic Profile of Insertion Mutations in Mouse Leukemias and Lymphomas," *Genome Res.* 10(2):237-243.

Heid, C. A et al. (1996). "Real Time Quantitative PCR," *Genome Research* 6:986-994.

Herdewjn, P. et al. (1994). "Hexopyranosyl-Like Oligonucleotides," Chapter 6 In *Carbohydrate Modifications in Antisense Research*. Shanghvi, Y. S and Cook, P. D, eds, ACS Symposium Series 580, American Chemical Society, Washington, pp. 80-99.

Higgins, D. G. and Sharp, P. M. (1989). "Fast and Sensitive Multiple Sequence Alignments on a Microcomputer," *CABIOS Communications* 5(2):151-153.

Hoogenboom, H. R. and Winter, G. (1991). "By-Passing Immunisation Human Antibodies from Synthetic Repertoires of Germline $V_H$ Gene Segments Rearranged in Vitro," *J. Mol. Biol.* 227:381-388.

Hopp, T. P. et al. (1988). "A Short Polypeptide Marker Sequence Useful for Recombinant Protein Identification and Purification," *Biotechnology* 6:1204-1210.

Horn, T. et al. (1996). "Oligonucleotides with Alternating Anionic and Cationic Phosphoramidate Linkages: Synthesis and Hybridization of Stereo-Uniform Isomers," *Tetrahedron Letters* 37(6):743-746.

Hwang, H. C. et al. (2002). "Identification of Oncognes Collaborating with p27$^{Kip1}$ Loss by Insertional Mutagenesis and High-Throughput Insertion Site Analysis," *Proc. Natl Acad. Sci. USA* 99(17):11293-11298 (Includes supporting information).

Jenkins, G. N. and Turner, N. J. (1995). "The Biosynthesis of Carbocyclic Nucleosides," *Chem. Soc. Rev.* pp. 169-176.

Jones, P. T. et al. (1986). "Replacing the Complementarity-Determining Regions in a Human Antibody with Those from a Mouse," *Nature* 321:522-525.

Jonkers, J. and Berns, A. (1996). "Retroviral Insertional Mutagenesis as a Strategy to Identify Cancer Genes," *Biochim. Biophys. Acta* 1287:29-57.

Joosten, M. et al. (2000). "Phenotyping of Evi 1, Evi 11/Cb2, and Evi 12 Transformed Leukemias Isolated from a Novel Panel of Cas-Br-M Murine Leukemia Virus-Infected Mice," *J. Virology* 268:308-318.

Jung, M. P. et al. (1994). "Hybridization of alternating Cationic/Anionic Oligonucleotides to RNA Segments," *Nucleosides & Nucleotides* 13(6&7):1597-1605.

Karlin, S. and Altschul, S.F. (1993). "Applications and Statistics for Multiple High-Scoring Segments in Molecular Sequences," *Proc. Natl Acad. Sci. USA* 90:5873-5877.

Köhler, G. and Milstein, C. (1975). "Continuous Cultures of Fused Cells Secreting Antibody of Predefined Specificity," *Nature* 256:495-497.

Kohno, T. et al. (2000). "Identification of Genes Associated with the Progression of Adult T-Cell Leukemia (ATL)," *Jpn. J. Cancer Res.* 91:1103-1110.

Lee, F. S. et al. (1995). "Insertional Mutagenesis Identifies a Member of the *Wnt* Gene Family as a Candidate Oncogene in the Mammary Eptithelium of *int-2/Fgf-3* Transgenic Mice,"*Proc. Natl. Acad. Sci. USA* 92:2268-2272.

Lee, S. Wong et al. (1999). "Cloning of Mouse Sepiapterin Reductase Gene and Characterization of its Promoter Region," *Biochimica and Biophysica Acta* 1445(1):165-171.

Letsinger, R. L. et al. (1986). "Effects of Pendant Groups at Phosphorus on Binding Properties of d-ApA Analogues," *Nucl. Acids. Res* 14(8):3487-3499.

Letsinger, R. L. et al. (1988). "Cationic Oligonucleotides," *J. Am. Chem. Soc.* 110:4470-4471.

Letsinger, R.L. and Mungall, W. S. (1970). "Phosphoramidate Analogs of Oligonucleotides," *J. Org. Chem* 35(11):3800-3803.

Li, J. et al. (1999). "Leukaemia Disease Genes: Large-Scale Cloning and Pathway Predictions," *Nature Genetics* 23:348-353.

Lockhart, D. J. et al. (1996). "Expression Monitoring by Hybridization High-Density Oligonucleotide Arrays," *Nature Biotechnology*, 14:1675-1680.

Lonberg, N. and Huszar, D. (1995). "Human Antibodies from Transgenic Mice," *Intern. Rev. Immunol.* 13:65-93.

Longberg, N. et al. (1994). "Antigen-Specific Human Antibodies from Mice Comprising Four Distinct Genetic Modifications," *Nature* 368:856-859.

Lund, A. H. et al. (2002). "Genome-Wide Retroviral Insertional Tagging of Genes Involved in Cancer in Cdkn2a-Deficient Mice," *Nature Genetics Advance online Publication* pp. 1-6.

Lutz-Freyermuth, C. et al. (1990). "Quantitative Determination That One of Two Potential RNA-Binding Domains of the A Protein Component of the U1 Small Nuclear Ribonucleoprotein Complex Binds with High Affinity to Stem-Loop II of U1 RNA," *Proc. Natl Acad. Sci. USA* 87:6393-6397.

MacArthur, C. A. et al. (1995). "*Fgf-8*, Activated by Proviral Insertion, Cooperates with the *Wnt-1* Transgene in Murine Mammary Tumorigenesis," *J. Virol.* 69(4):2501-2507.

Maddry, J. A. et al. (1994). "Synthesis of Nonionic Olgonucleotide Analogues," Chapter 3 *In Carbohydrate Modifications in Antisense Research*. Shanghvi, Y. S and Cook, P. D, eds, ACS Symposium Series 580 American Chemical Society, Washington, pp. 40-51.

Mag, M. et al. (1991). "Synthesis and Selective Cleavage of an Oligodeoynucleotide Containing a Bridged Internucleotide 5'-Phosphorotiate Linkage," *Nucleic Acids Res.* 19(7):1437-1441.

Marchetti, A. et al. (1995). "*Int-6*, a Highly Conserved, Widely Expressed Gene, is Mutated by Mouse Mammary Tumor Virus in Mammary Preneoplasia," *J. Virol.* 69(3):1932-1938.

Marks, J. D. et al. (1991). "By-Passing Immunization, Human Antibodies from V-Gene Libraries Displayed on Phage," *J. Mol. Biol.* 222:581-597.

Marks, J. D. et al. (1992). "By-Passing Immunization: Building High Affinity Human Antibodies by Chain Shuffling," *Bio/Technology* 10:779-783.

Martin, G. A. et al. (1992). "GAP Domains Responsible for Ras p21-Dependent Inhibition of Muscarinic Atrial K+ Channel Currents," *Science* 255:192-194.

Meier, C. et al. (1992). "Peptide Nucleic Acids (PNAs)—Unusual Properties of Nonionic Oligonucleotide Analogues," *Angew Chem. Int. Ed. Engl.* 31(8):1008-1010.

Mikkers ,H. et al. (2002). "High-Throughput Retroviral Tagging to Identify Components of Specific Signaling Pathways in Cancer," *Nature Genetics Advance Online Publication*, pp. 1-7.

Moore, A. S. (2001). "The Role of Chemoattraction in Cancer Metastases," *BioEssays* 23(8):674-676.

Morris, D. W. et al. (1986). "Transfer, by Selective Breeding, of the Pathogenic *Mtv-2* Endogenous Provirus from the GR strain to a Wild Mouse Line Free of Endogenous and Exogenous Mouse Mammary Tumor Virus," *J. Virol.* 58(2):247-252.

Morris, D. W. et al. (1990). "Insertion Mutation of the *Int-1* and *Int-2* Loci by Mouse Mammary Tumor Virus in Premalignant and Malignant Neoplasms from the GR Mouse Strain," *J. Virol.* 64(4):1794-1802.

Morrison, S. L. (1994). "Success in Specification," *Nature* 368:812-813.

Müller, A. et al. (2001). "Involvement of Chemokine Receptors in Breast Cancer Metastasis," *Nature* 410:50-56.

Needleman, S. B. and Wunsch, C. D. (1970). "A General Method Applicable to the Search for Similiarities in the Amino Acid Sequence of Two Proteins," *J. Mol. Biol.* 48:443-453.

Neuberger, M. (1996). "Generating High-Avidity Human Mabs in Mice," *Nature Biotechnology* 14:826 (1 page total).

Nusse, R. and Varmus, H. E. (1982). "Many Tumors Induced by the Mouse Mammary Tumor Virus Contain a Provirus Integrated in the Same Region of the Host Genome," *Cell* 31:99-109.

Nygren, H. (1982). "Conjugation of Horseradish Peroxidase to Fab Fragments with Different Homobifunctional and Heterobifunctional Cross-Linking Reagents," *J. Histochem. and Cytochem.* 30(5):407-412.

Paborsky, L. R. et al. (1990). "Mammalian Cell Transient Expression of Tissue Factor for the Production of Antigen," *Protein Engineering* 3(6):547-553.

Pain, D. and Surolia, A. (1981). "Preparation of Protein A-Peroxidase Monoconjugate Using A Heterobifunctional Reagent, and its Use in Enzyme Immunoassays," *J. Immunol. Meth.* 40:219-230.

Palmarini, M. et al. (1999). "Jaagsiekte Sheep Retrovirus is Necessary and Sufficient to Induce a Contagious Lung Cancer in Sheep," *J. Virol.* 73(8):6964-6972.

Pauwels, R. et al. (1986). "Biological Activity of New 2-5A Analogues," *Chemica Scripta* 26:141-145.

Pearson, W. R. and Lipman, D. J. (1988). "Improved Tools for Biological Sequence Comparison," 85:2444-2448.

Peters, G. et al. (1983). "Tumorigenesis by Mouse Mammary Turmor Virus: Evidence for a Common Region for Provirus Integration in Mammary Tumors," *Cell* 33:369-377.

Peters, G. et al. (1989). "The Mouse Homolog of the *Hst/k-FGF* Gene is Adjacent to *int-2* and is Activated by Proviral Insertion in Some Virally Induced Mammary Tumors," *Proc. Natl. Acad. Sci. USA* 86:5678-5682.

Pierce (1994). "Cross-Linking," *Pierce Catalog and Handbook* pp. 155-200.

Presta, L. G. (1992). "Antibody Engineering", *Current Opinion in Structural Biology* 2:593-596.

Rawls, R. L. (1997). "Optimistic About Antisense," *C & E News* pp. 35-40.

Riechmann, L. et al. (1988). "Reshaping Human Antibodies for Therapy," *Nature* 332:323-327.

Roelink, H. et al. (1990). "*Wnt-3*, a Gene Activated by Proviral Insertion in Mouse Mammary Tumors is Homologous to *int-1/Wnt-1* and is Normally Expressed in Mouse Embryos and Adult Brain," *Proc. Natl. Acad. Sci USA* 87:4519-4523.

Sambrook, J. et al., eds. (1989). *Molecular Cloning, a Laboratory Manual*, Second Edition. Cold Spring Harbor Laboraroty Press. pp. xi-xxxviii. (Table of Contents Only).

Scopes, R. K.,ed. (1982). *Protein Purification: Principles and Practice*. Springer-Verlag, New York, Heidelberg, Berlin, pp. xi-xiii.

Shiramizu, B. et al. (1994). "Identification of a Common Clonal Human Immunodeficiency Virus Integration Site in Human Immunodeficiency Virus-Associated Lymphomas," *Cancer Res.* 54:2069-2072.

Smith, T. F. and Waterman, M. S. (1981). "Comparison of Biosequences," *Adv. Appl. Math.* 2:482-489.

Sojar, H. T. and Bahl, O. P. (1987). "A Chemical Method for the Deglycosylation of Proteins," *Archives of Biochemistry and Biophysics* 259(1):52-57.

Sorensen, A. B. et al. (1993). "Amplification and Sequence Analysis of DNA Flanking Integrated Proviruses by a Simple Two-Step Polymerase Chain Reaction Method," *Journal of Virology* 67(12):7118-7124.

Sorensen, A. B. et al. (1993). "Sequence Tags for Provirus Integration Sites in DNAs of Tumors Induced by the Murine Retrovirus SL3-3," *Journal of Virology* 70(6):4063-4070.

Sorensen, A. B. et al. (2000). "Sintl, a Common Integration Site in SL3-3-Induced T-Cell Lymphomas, Harbors a Putative Proto-Oncogene with Homology to the Septin Gene Family, "*J. Virology* 74(5):2161-2168.

Sprinzl, M. et al. (1977). "Enzymatic Incorporation of ATP and CTP Analogues Into the 3' End of tRNA," *Eur. J. Biochem* 81:579-589.

Stein, C. A. and Cohen, J. S. (1988). "Oligodeoxynucleotides as Inhibitors of Gene Expression: A Review," *Cancer Res.* 48:2659-2668.

Sternsdorf, T. et al. (1997). "Nuclear Dots: Actors on Many Stages," *Immunobiology* 198:307-331.

Suzuki, T. et al. (2002). "New Genes Involved in Cancer Identified by Retroviral Tagging," *Nature Genetics Advance Online Publication* pp. 1-9.

Suzuki, T. et al. (2002). "Web Note A: CIS Definition, Retroviral Tagging in the Post-Genome Era Identifies New Genes Involved in Cancer". (1 page total).

Thotakura, N. R. and Bahl, O. P. (1987). "Enzymathic Deglycosylation of Glycoproteins," *In Methods in Enzymology* Academic Press, Inc., vol. 138. pp. 350-359.

Tijssen (1993). "Overview of Principles of Hybridization and the strategy of nucleic acid assays," Chapter 2 *In Laboratory Techniques in Biochemistry and Molecular Biology*, Hybridization with Nucleic Acid Probes, Van der Vliet, P. C., ed. Elsevier, Amsterdam, London, New York, and Tokyo, vol. 24 pp. 20-78.

Van der Krol, A. R et al. (1988). "Modulation of Eukaryotic Gene Expression by Complementary RNA or DNA Sequences," *Biotechniques* 6(10):958-976.

Varmus, H. E. (1983). "Using Retroviruses as Insertional Mutagens to Identify Cellular Oncogenes," *In Oncogenes and Retroviruses: Evaluation of Basic Findings and Clinical Potential*. Alan R. Liss, Inc., New York. pp. 23-35.

Vaughn, J. et al. (2000). "Genomic Structure and Expression of Human *KCNJ9* (Kir3.3/GIRK3)," *Biochem. Biophys. Res. Commun.* 274(2):302-309.

Verhoeyen, M. et al. (1988). "Reshaping Human Antibodies: Grafting an Antilysozyme Activity," *Science* 239:1534-1536.

von Kiedrowski, G. et al. (1991). "Parabolic Growth of a Self-Replicating Hexdeoxynucleotide Bearing a 3'-5'-Phosphoamidate Linkage," *Angew. Chem. Int. Ed. Engl* 30(4):423-426.

Washington University. (2002). "Washington University BLAST Archives" located at http://blast.wustl visited on Dec. 15, 2002.

Wolford, J. K. (2001). "Analysis of Linkage Disequilibrium Between Polymorphisms in the *KCNJ9* Gene with Type 2 Diabetes Mellitus in Pima Indians," *Mol. Genet. Metab* 73(1):97-103.

Zhang, W-X and Yang, S. Y. (2000). "Cloning and Characterization of a New Member of the T-Box Gene Family," *Genomics* 70(1):41-48.

Zlokarnik, G. et al. (1998). "Quantitation of Transcription and Clonal Selection of Single Living Cells with β-Lactamase as Reporter," *Science* 279:84-88.

International Search Report mailed on Dec. 1, 2003, for PCT patent application No. PCT/US02/33835 filed on Oct. 22, 2002, 4 pages.

Berns, A. (Date unknown). "Table A: Retroviral insertion Sites in $E\mu Myc$ and $E\mu Myc;Pim1^{-/-}$; $Pim2^{-/-}$lymphomas$^{a}$", published in the advance online issue of *Nature Genetics*, 13 pages total.

Berns, A. (Date Unknown). "Web Fig. A", describing PIM protein actions, published in the advance online issue of the *Nature Genetics*, 1 page total.

Campbell, A. M. (1984). "The Production and Characterization of Rodent and Human Hybridomas", Chapter 1 *In Monoclonal Antibody Technology*. Burdon, R. H. and van Knippenberg, P.H., eds, Elsevier, pp. 1-32.

Database GenCore on STN, Accession No. U52152, Schoots et al. "Cloning of four inwardly rectifying potassium channels from human", Direct Submission Mar. 25, 2996 amino acid and nucleic acid sequences.

Database GenCore on STN, on Accession No. AF275818, Yang et al. Jul. 23, 2000. "A family of novel PR-Domain (PRDM) genes as candidate tumor suppressors".

Hunter, W. M. and Greenwood, F. C., "Preparation of Iodine-131 Labelled Human Growth Hormone of High Specific Activity", *Nature* May 5, 1962, vol. 194: pp. 495-496.

Jiang, G-L et al. (2000). "The *yin-yang* of PR-domain family genes in tumorigenesis", *Histol. Histopathol* 15(1): pp. 109-117.

Lohuizen, V. (Date unknown). "Web Table A", describing genomic positions insertion site sequences analyzed against the Celera Mouse Genome Database (CMGD Release 12), published in the advance online issue of *Nature Genetics*, 9 pages total.

Lohuizen, V. (Date unknown). "Web Table B", describing genomic positions of insertion site sequences analyzed against the Ensembl Mouse Genome Database (Feb. 2002 freeze), published in the advance online issue of *Nature Genetics*, 12 pages total.

Lohuizen, V. (Date unknown). "Web Table C", listing GenBank accession Nos., published in the advance online issue of *Nature Genetics*, 11 pages total.

Sawai, H. et al. (1984). "Synthesis and Properties of Oligoadenylic Acids Containing 2'-5' Phosphoramide Linkage", *Chem. Lett.* pp. 805-808.

Schoots, O. et al (1999). "Co-expression of Human Kir3 Subunits Can Yield Channels with Different Functional Properties", *Cell. Signal.* 11(12) pp. 871-883.

Skinner, R. H. et al. (1991). "Use of the Glu-Glu-Phe C-terminal Epitope for Rapid Purification of the Catalytic Domain of Normal and Mutant *ras* GTPase-activating Proteins", *J. Biol. Chem.* 266(22) pgs. 14163-14166.

GenBank Accession No. AF357835. Sasaki, S.et al. (2000 ). "Cloning and Expression of Human B Cell-Specific Transcription Factor $BACH_2$ Mapped to Chromosome 6q15," *Oncogene* 19:3739-3749. (Abstract Only).

International Search Report mailed on Jun. 15, 2004, for PCT patent application No. PCT/US02/36071 filed on Nov. 8, 2002, 5 pages.

International Search Report mailed on Jun. 16, 2004, for PCT patent application No. PCT/US03/40082 filed on Dec. 15, 2003, 5 pages.

Sasaki, S.et al. (2000). "Cloning and Expression of Human B Cell-Specific Transcription Factor $BACH_2$ Mapped to Chromosome 6q15," *Oncogene* 19:3739-3749.

Kudo, S. et al., (1991), *The Journal of Biological Chemistry* 266:8483-8489.

Lai, R. et al., (1999), *American Journal of Clinical Pathology* 111:488-494.

Santamaria, M. et al., (1996) *Cancer Research* 56:3526-3529.

Sikut, R. et al., (1997) *Biochemical and Biophysical Research Communications* 238:612-619.

Sikut, R. et al., (1999) *International Journal of Cancer* 82:52-58.

Traweek, S. T. et al., (1993) *The American Journal of Surgical Pathology* 17(10):1011-1019.

Treasure, J. et al. (1992) *Journal of Clinical Pathology* 45:1018-1022.

International Search Report mailed on Jul. 26, 2004, for PCT patent application No. PCT/US02/38582, filed on Dec. 2, 2002, 8 pages.

Database EMBL, Accession No. AF127773.1, Szelei et al., "Identification of human estrogen-inducible transcripts from a serum-resistant variant of breast cancer MCF7 cells," (1999).

Databse EMBL, Accession No. AC110769, Kozlowicz et al., "*Homo sapiens* BAC clone RP11-141B14 from 2, complete sequence," (2002)**.

Database EMB, Accession No. AF006083, Welch et al., "*Homo sapiens* actin-related protein Arp3 (ARP3) mRNA, complete cds," (1999).

Database Geneseq, Accession No. AAM78861, "Human protein SEQ ID No. 1523," (2001).

Database Geneseq, Accession No. ADJ66601, "Actin-like protein 3 for anti-cancer protein complex," (2004).

Database Uniport, Accession No. "Actin-like protein 3; Actin-2," (2001), P32391.

Shindo-Okada et al., Isolation of a novel actin-related gene expressed in low-metastatic PC-14 human lung adenocarinoma, *Biochem. and Biophys. Res. Comm.* 280(1):61-67 (2001).

Otsubo et al., "Involvement of Arp2/3 complex in the process of colorectal carcinogensis," *Modern Pathology* 17:461-467 (2004).

Szelei et al., "Identification of human estrogen-inducible transcripts that potentially mediate the apoptotic response in breast cancer," *J. of Steroid Biochem. and Mol. Biol.* 72(3-4):89-102 (2000).

Welch et al., "The human Arp2/3 complex is composed of evolutionary conserved subunits and is localized to cellular regions of dynamic actin filament assembly," *J. of Cell Biology* 138(2): 375-384 (1997).

Wulfkuhle et al., "Proteomic analysis of ductal carcinoma in situ of the human breast," *Proceedings of the American Association for Cancer Research Annual Meeting* 43:38 (2002).

Zheng et al., "Arp2/3 overexpression contributed to pathogenesis, growth and invasion of gastric carcinoma," *Anticancer Res.* 28:2225-2232 (2008).

* cited by examiner ns COMPOSITIONS AND METHODS FOR CANCER

The present application is a continuing application of U.S. Ser. Nos. 09/747,377, filed Dec. 22, 2000 now abandoned and 09/798,586, filed Mar. 2, 2001, now abandoned both of which are expressly incorporated herein by reference.

SEQUENCE LISTING

The Sequence Listing submitted on compact disc under 37 C.F.R. §1.821(c), is incorporated herein by reference. Two identical discs submitted on CD-R are labeled "CRF" and "Sequence Listing".

FIELD OF THE INVENTION

The present invention relates to novel sequences for use in diagnosis and treatment of cancer, especially carcinomas, as well as the use of the novel compositions in screening methods.

BACKGROUND OF THE INVENTION

Oncogenes are genes that can cause cancer. Carcinogenesis can occur by a wide variety of mechanisms, including infection of cells by viruses containing oncogenes, activation of protooncogenes in the host genome, and mutations of protooncogenes and tumor suppressor genes.

There are a number of viruses known to be involved in human cancer as well as in animal cancer. Of particular interest here are viruses that do not contain oncogenes themselves; these are slow-transforming retroviruses. They induce tumors by integrating into the host genome and affecting neighboring protooncogenes in a variety of ways, including promoter insertion, enhancer insertion, and/or truncation of a protooncogene or tumor suppressor gene. The analysis of sequences at or near the insertion sites led to the identification of a number of new protooncogenes.

With respect to lymphoma and leukemia, murine leukemia retrovirus (MuLV), such as SL3-3 or Akv, is a potent inducer of tumors when inoculated into susceptible newborn mice, or when carried in the germline. A number of sequences have been identified as relevant in the induction of lymphoma and leukemia by analyzing the insertion sites; see Sorensen et al., J. of Virology 74:2161 (2000); Hansen et al., Genome Res. 10(2):237-43 (2000); Sorensen et al., J. Virology 70:4063 (1996); Sorensen et al. J. Virology 67:7118 (1993); Joosten et al., Virology 268:308 (2000); and Li et al., Nature Genetics 23:348 (1999); all of which are expressly incorporated by reference herein.

Accordingly, it is an object of the invention to provide sequences involved in cancer and in particular in oncogenesis.

SUMMARY OF THE INVENTION

In accordance with the objects outlined above, the present invention provides methods for screening for compositions which modulate carcinomas, especially lymphoma and leukemia. Also provided herein are methods of inhibiting proliferation of a cell, preferably a lymphoma cell. Methods of treatment of carcinomas, including diagnosis, are also provided herein.

In one aspect, a method of screening drug candidates comprises providing a cell that expresses a carcinoma associated (CA) gene or fragments thereof. Preferred embodiments of CA genes are genes which are differentially expressed in cancer cells, preferably lymphatic, breast, prostate or epithelial cells, compared to other cells. Preferred embodiments of CA genes used in the methods herein include, but are not limited to the nucleic acids selected from Table 1 06-001 to 06-343. The method further includes adding a drug candidate to the cell and determining the effect of the drug candidate on the expression of the CA gene.

In one embodiment, the method of screening drug candidates includes comparing the level of expression in the absence of the drug candidate to the level of expression in the presence of the drug candidate.

Also provided herein is a method of screening for a bioactive agent capable of binding to a CA protein (CAP), the method comprising combining the CAP and a candidate bioactive agent, and determining the binding of the candidate agent to the CAP.

Further provided herein is a method for screening for a bioactive agent capable of modulating the activity of a CAP. In one embodiment, the method comprises combining the CAP and a candidate bioactive agent, and determining the effect of the candidate agent on the bioactivity of the CAP.

Also provided is a method of evaluating the effect of a candidate carcinoma drug comprising administering the drug to a patient and removing a cell sample from the patient. The expression profile of the cell is then determined. This method may further comprise comparing the expression profile of the patient to an expression profile of a healthy individual.

In a further aspect, a method for inhibiting the activity of an CA protein is provided. In one embodiment, the method comprises administering to a patient an inhibitor of a CA protein preferably selected from the group consisting of the sequences outlined in Table 1 06-001 to 06-343 or their complements.

A method of neutralizing the effect of a CA protein, preferably a protein encoded by a nucleic acid selected from the group of sequences outlined in Table 1 06-001 to 06-343, is also provided. Preferably, the method comprises contacting an agent specific for said protein with said protein in an amount sufficient to effect neutralization.

Moreover, provided herein is a biochip comprising a nucleic acid segment which encodes a CA protein, preferably selected from the sequences outlined in Table 1 06-001 to 06-343.

Also provided herein is a method for diagnosing or determining the propensity to carcinomas, especially lymphoma or leukemia by sequencing at least one carcinoma or lymphoma gene of an individual. In yet another aspect of the invention, a method is provided for determining carcinoma including lymphoma and leukemia gene copy number in an individual.

Novel sequences are also provided herein. Other aspects of the invention will become apparent to the skilled artisan by the following description of the invention.

DETAILED DESCRIPTION OF THE INVENTION

The present invention is directed to a number of sequences associated with carcinomas, especially lymphoma, breast cancer or prostate cancer. The relatively tight linkage between clonally-integrated proviruses and protooncogenes forms "provirus tagging", in which slow-transforming retroviruses that act by an insertion mutation mechanism are used to isolate protooncogenes. In some models, uninfected animals have low cancer rates, and infected animals have high cancer rates. It is known that many of the retroviruses involved do not carry transduced host protooncogenes or pathogenic transacting viral genes, and thus the cancer incidence must therefor be a direct consequence of proviral integration effects into host protooncogenes. Since proviral integration is random, rare integrants will "activate" host protooncogenes that provide a selective growth advantage, and these rare events result in new proviruses at clonal stoichiometries in tumors.

The use of oncogenic retroviruses, whose sequences insert into the genome of the host organism resulting in carcinoma, allows the identification of host sequences involved in carcinoma. These sequences may then be used in a number of different ways, including diagnosis, prognosis, screening for modulators (including both agonists and antagonists), antibody generation (for immunotherapy and imaging), etc. However, as will be appreciated by those in the art, oncogenes that are identified in one type of cancer such as lymphoma or leukemia have a strong likelihood of being involved in other types of cancers as well. Thus, while the sequences outlined herein are initially identified as correlated with lymphoma, they can also be found in other types of cancers as well, outlined below.

Accordingly, the present invention provides nucleic acid and protein sequences that are associated with carcinoma, herein termed "carcinoma associated" or "CA" sequences. In a preferred embodiment, the present invention provides nucleic acid and protein sequences that are associated with carcinomas which originate in lymphatic tissue, herein termed "lymphoma associated", "leukemia associated" or "LA" sequences.

Suitable cancers which can be diagnosed or screened for using the methods of the present invention include cancers classified by site or by histological type. Cancers classified by site include cancer of the oral cavity and pharynx (lip, tongue, salivary gland, floor of mouth, gum and other mouth, nasopharynx, tonsil, oropharynx, hypopharynx, other oral/pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix uteri; corpus uteri; uterus, nos; ovary; vagina; vulva; and other female genital); cancers of the male genital system (prostate gland; testis; penis; and other male genital); cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); cancers of the lymphomas (hodgkin's disease and non-hodgkin's lymphoma), multiple myeloma, and leukemias (lymphocytic leukemia; myeloid leukemia; monocytic leukemia; and other leukemias).

Other cancers, classified by histological type, that may be associated with the sequences of the invention include, but are not limited to, Neoplasm, malignant; Carcinoma, NOS; Carcinoma, undifferentiated, NOS; Giant and spindle cell carcinoma; Small cell carcinoma, NOS; Papillary carcinoma, NOS; Squamous cell carcinoma, NOS; Lymphoepithelial carcinoma; Basal cell carcinoma, NOS; Pilomatrix carcinoma; Transitional cell carcinoma, NOS; Papillary transitional cell carcinoma; Adenocarcinoma, NOS; Gastrinoma, malignant; Cholangiocarcinoma; Hepatocellular carcinoma, NOS; Combined hepatocellular carcinoma and cholangiocarcinoma; Trabecular adenocarcinoma; Adenoid cystic carcinoma; Adenocarcinoma in adenomatous polyp; Adenocarcinoma, familial polyposis coli; Solid carcinoma, NOS; Carcinoid tumor, malignant; Branchiolo-alveolar adenocarcinoma; Papillary adenocarcinoma, NOS; Chromophobe carcinoma; Acidophil carcinoma; Oxyphilic adenocarcinoma; Basophil carcinoma; Clear cell adenocarcinoma, NOS; Granular cell carcinoma; Follicular adenocarcinoma, NOS; Papillary and follicular adenocarcinoma; Nonencapsulating sclerosing carcinoma; Adrenal cortical carcinoma; Endometroid carcinoma; Skin appendage carcinoma; Apocrine adenocarcinoma; Sebaceous adenocarcinoma; Ceruminous adenocarcinoma; Mucoepidermoid carcinoma; Cystadenocarcinoma, NOS; Papillary cystadenocarcinoma, NOS; Papillary serous cystadenocarcinoma; Mucinous cystadenocarcinoma, NOS; Mucinous adenocarcinoma; Signet ring cell carcinoma; Infiltrating duct carcinoma; Medullary carcinoma, NOS; Lobular carcinoma; Inflammatory carcinoma; Paget's disease, mammary; Acinar cell carcinoma; Adenosquamous carcinoma; Adenocarcinoma w/ squamous metaplasia; Thymoma, malignant; Ovarian stromal tumor, malignant; Thecoma, malignant; Granulosa cell tumor, malignant; Androblastoma, malignant; Sertoli cell carcinoma; Leydig cell tumor, malignant; Lipid cell tumor, malignant; Paraganglioma, malignant; Extra-mammary paraganglioma, malignant; Pheochromocytoma; Glomangiosarcoma; Malignant melanoma, NOS; Amelanotic melanoma; Superficial spreading melanoma; Malig melanoma in giant pigmented nevus; Epithelioid cell melanoma; Blue nevus, malignant; Sarcoma, NOS; Fibrosarcoma, NOS; Fibrous histiocytoma, malignant; Myxosarcoma; Liposarcoma, NOS; Leiomyosarcoma, NOS; Rhabdomyosarcoma, NOS; Embryonal rhabdomyosarcoma; Alveolar rhabdomyosarcoma; Stromal sarcoma, NOS; Mixed tumor, malignant, NOS; Mullerian mixed tumor; Nephroblastoma; Hepatoblastoma; Carcinosarcoma, NOS; Mesenchymoma, malignant; Brenner tumor, malignant; Phyllodes tumor, malignant; Synovial sarcoma, NOS; Mesothelioma, malignant; Dysgerminoma; Embryonal carcinoma, NOS; Teratoma, malignant, NOS; Struma ovarii, malignant; Choriocarcinoma; Mesonephroma, malignant; Hemangiosarcoma; Hemangioendothelioma, malignant; Kaposi's sarcoma; Hemangiopericytoma, malignant; Lymphangiosarcoma; Osteosarcoma, NOS; Juxtacortical osteosarcoma; Chondrosarcoma, NOS; Chondroblastoma, malignant; Mesenchymal chondrosarcoma; Giant cell tumor of bone; Ewing's sarcoma; Odontogenic tumor, malignant; Ameloblastic odontosarcoma; Ameloblastoma, malignant; Ameloblastic fibrosarcoma; Pinealoma, malignant; Chordoma; Glioma, malignant; Ependymoma, NOS; Astrocytoma, NOS; Protoplasmic astrocytoma; Fibrillary astrocytoma; Astroblastoma; Glioblastoma, NOS; Oligodendroglioma, NOS; Oligodendroblastoma; Primitive neuroectodermal; Cerebellar sarcoma, NOS; Ganglioneuroblastoma; Neuroblastoma, NOS; Retinoblastoma, NOS; Olfactory neurogenic tumor; Meningioma, malignant; Neurofibrosarcoma; Neurilemmoma, malignant; Granular cell tumor, malignant; Malignant lymphoma, NOS; Hodgkin's disease, NOS; Hodgkin's; paragranuloma, NOS; Malignant lymphoma, small lymphocytic; Malignant lymphoma, large cell, diffuse; Malignant lymphoma, follicular, NOS; Mycosis fungoides; Other specified non-Hodgkin's lymphomas; Malignant histiocytosis; Multiple myeloma; Mast cell sarcoma; Immunoproliferative small intestinal disease; Leukemia, NOS; Lymphoid leukemia, NOS; Plasma cell leukemia; Erythroleukemia; Lymphosarcoma cell leukemia; Myeloid leukemia, NOS; Basophilic leukemia; Eosinophilic leukemia; Monocytic leukemia, NOS; Mast cell leukemia; Megakaryoblastic leukemia; Myeloid sarcoma; and Hairy cell leukemia.

In addition, the genes may be involved in other diseases, such as but not limited to diseases associated with aging or neurodegenerative diseases.

Association in this context means that the nucleotide or protein sequences are either differentially expressed, activated, inactivated or altered in carcinomas as compared to normal tissue. As outlined below, CA sequences include those that are up-regulated (i.e. expressed at a higher level), as well as those that are down-regulated (i.e. expressed at a lower level), in carcinomas. CA sequences also include sequences which have been altered (i.e., truncated sequences or sequences with substitutions, deletions or insertions, including point mutations) and show either the same expression profile or an altered profile. In a preferred embodiment, the CA sequences are from humans; however, as will be appreciated by those in the art, CA sequences from other organisms may be useful in animal models of disease and drug evaluation; thus, other CA sequences are provided, from vertebrates, including mammals, including rodents (rats, mice, hamsters, guinea pigs, etc.), primates, farm animals (including sheep, goats, pigs, cows, horses, etc). In some cases, prokaryotic CA sequences may be useful. CA sequences from other organisms may be obtained using the techniques outlined below.

CA sequences can include both nucleic acid and amino acid sequences. In a preferred embodiment, the CA sequences are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an CA protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In a preferred embodiment, the CA sequences are nucleic acids. As will be appreciated by those in the art and is more fully outlined below, CA sequences are useful in a variety of applications, including diagnostic applications, which will detect naturally occurring nucleic acids, as well as screening applications; for example, biochips comprising nucleic acid probes to the CA sequences can be generated. In the broadest sense, then, by "nucleic acid" or "oligonucleotide" or grammatical equivalents herein means at least two nucleotides covalently linked together. A nucleic acid of the present invention will generally contain phosphodiester bonds, although in some cases, as outlined below (for example in antisense applications or when a candidate agent is a nucleic acid), nucleic acid analogs may be used that have alternate backbones, comprising, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365: 566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done for a variety of reasons, for example to increase the stability and half-life of such molecules in physiological environments for use in anti-sense applications or as probes on a biochip.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. As will be appreciated by those in the art, the depiction of a single strand "Watson" also defines the sequence of the other strand "Crick"; thus the sequences described herein also includes the complement of the sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

An CA sequence can be initially identified by substantial nucleic acid and/or amino acid sequence homology to the CA sequences outlined herein. Such homology can be based upon the overall nucleic acid or amino acid sequence, and is generally determined as outlined below, using either homology programs or hybridization conditions.

The CA sequences of the invention were initially identified as described herein; basically, infection of mice with murine leukemia viruses (MLV) resulted in lymphoma, although many of these sequences will also be involved in other cancers as is generally outlined herein.

The CA sequences outlined herein comprise the insertion sites for the virus. In general, the retrovirus can cause carcinomas in three basic ways: first of all, by inserting upstream of a normally silent host gene and activating it (e.g. promoter insertion); secondly, by truncating a host gene that leads to oncogenesis; or by enhancing the transcription of a neighboring gene. For example, retrovirus enhancers, including SL3-3, are known to act on genes up to approximately 200 kilobases of the insertion site.

In a preferred embodiment, CA sequences are those that are up-regulated in carcinomas; that is, the expression of these genes is higher in carcinoma tissue as compared to normal tissue of the same differentiation stage. "Up-regulation" as used herein means at least about 50%, more preferably at least about 100%, more preferably at least about 150%, more preferably, at least about 200%, with from 300 to at least 1000% being especially preferred.

In a preferred embodiment, CA sequences are those that are down-regulated in carcinomas; that is, the expression of these genes is lower in carcinoma tissue as compared to normal I tissue of the same differentiation stage. "Downregulation" as used herein means at least about 50%, more preferably at least about 100%, more preferably at least about 150%, more preferably, at least about 200%, with from 300 to at least 1000% being especially preferred.

In a preferred embodiment, CA sequences are those that are altered but show either the same expression profile or an altered profile as compared to normal lymphoid tissue of the same differentiation stage. "Altered CA sequences" as used herein refers to sequences which are truncated, contain insertions or contain point mutations.

CA proteins of the present invention may be classified as secreted proteins, transmembrane proteins or intracellular proteins.

In a preferred embodiment the CA protein is an intracellular protein. Intracellular proteins may be found in the cytoplasm and/or in the nucleus. Intracellular proteins are involved in all aspects of cellular function and replication (including, for example, signaling pathways); aberrant expression of such proteins results in unregulated or disregulated cellular processes. For example, many intracellular proteins have enzymatic activity such as protein kinase activity, protein phosphatase activity, protease activity, nucleotide cyclase activity, polymerase activity and the like. Intracellular proteins also serve as docking proteins that are involved in organizing complexes of proteins, or targeting proteins to various subcellular localizations, and are involved in maintaining the structural integrity of organelles.

An increasingly appreciated concept in characterizing intracellular proteins is the presence in the proteins of one or more motifs for which defined functions have been attributed. In addition to the highly conserved sequences found in the enzymatic domain of proteins, highly conserved sequences have been identified in proteins that are involved in protein-protein interaction. For example, Src-homology-2 (SH2) domains bind tyrosine-phosphorylated targets in a sequence dependent manner. PTB domains, which are distinct from SH2 domains, also bind tyrosine phosphorylated targets. SH3 domains bind to proline-rich targets. In addition, PH domains, tetratricopeptide repeats and WD domains to name only a few, have been shown to mediate protein-protein interactions. Some of these may also be involved in binding to phospholipids or other second messengers. As will be appreciated by one of ordinary skill in the art, these motifs can be identified on the basis of primary sequence; thus, an analysis of the sequence of proteins may provide insight into both the enzymatic potential of the molecule and/or molecules with which the protein may associate.

In a preferred embodiment, the CA sequences are transmembrane proteins. Transmembrane proteins are molecules that span the phospholipid bilayer of a cell. They may have an intracellular domain, an extracellular domain, or both. The intracellular domains of such proteins may have a number of functions including those already described for intracellular proteins. For example, the intracellular domain may have enzymatic activity and/or may serve as a binding site for additional proteins. Frequently the intracellular domain of transmembrane proteins serves both roles. For example certain receptor tyrosine kinases have both protein kinase activity and SH2 domains. In addition, autophosphorylation of tyrosines on the receptor molecule itself, creates binding sites for additional SH2 domain containing proteins.

Transmembrane proteins may contain from one to many transmembrane domains. For example, receptor tyrosine kinases, certain cytokine receptors, receptor guanylyl cyclases and receptor serine/threonine protein kinases contain a single transmembrane domain. However, various other proteins including channels and adenylyl cyclases contain numerous transmembrane domains. Many important cell surface receptors are classified as "seven transmembrane domain" proteins, as they contain 7 membrane spanning regions. Important transmembrane protein receptors include, but are not limited to insulin receptor, insulin-like growth factor receptor, human growth hormone receptor, glucose transporters, transferrin receptor, epidermal growth factor receptor, low density lipoprotein receptor, epidermal growth factor receptor, leptin receptor, interleukin receptors, e.g. IL-1 receptor, IL-2 receptor, etc.

Characteristics of transmembrane domains include approximately 20 consecutive hydrophobic amino acids that may be followed by charged amino acids. Therefore, upon analysis of the amino acid sequence of a particular protein, the localization and number of transmembrane domains within the protein may be predicted.

The extraceullar domains of transmembrane proteins are diverse, however, conserved motifs are found repeatedly among various extracellular domains. Conserved structure and/or functions have been ascribed to different extracellular motifs. For example, cytokine receptors are characterized by a cluster of cysteines and a WSXWS (SEQ ID NO: 2059) (W=tryptophan, S=serine, X=any amino acid) motif. Immunoglobulin-like domains are highly conserved. Mucin-like domains may be involved in cell adhesion and leucine-rich repeats participate in protein-protein interactions.

Many extracellular domains are involved in binding to other molecules. In one aspect, extracellular domains are receptors. Factors that bind the receptor domain include circulating ligands, which may be peptides, proteins, or small molecules such as adenosine and the like. For example, growth factors such as EGF, FGF and PDGF are circulating growth factors that bind to their cognate receptors to initiate a variety of cellular responses. Other factors include cytokines, mitogenic factors, neurotrophic factors and the like. Extracellular domains also bind to cell-associated molecules. In this respect, they mediate cell-cell interactions. Cell-associated ligands can be tethered to the cell for example via a glycosylphosphatidylinositol (GPI) anchor, or may themselves be transmembrane proteins. Extracellular domains also associate with the extracellular matrix and contribute to the maintenance of the cell structure.

CA proteins that are transmembrane are particularly preferred in the present invention as they are good targets for immunotherapeutics, as are described herein. In addition, as outlined below, transmembrane proteins can be also useful in imaging modalities.

It will also be appreciated by those in the art that a transmembrane protein can be made soluble by removing transmembrane sequences, for example through recombinant methods. Furthermore, transmembrane proteins that have been made soluble can be made to be secreted through recombinant means by adding an appropriate signal sequence.

In a preferred embodiment, the CA proteins are secreted proteins; the secretion of which can be either constitutive or regulated. These proteins have a signal peptide or signal sequence that targets the molecule to the secretory pathway. Secreted proteins are involved in numerous physiological events; by virtue of their circulating nature, they serve to transmit signals to various other cell types. The secreted protein may function in an autocrine manner (acting on the cell that secreted the factor), a paracrine manner (acting on cells in close proximity to the cell that secreted the factor) or an endocrine manner (acting on cells at a distance). Thus secreted molecules find use in modulating or altering numerous aspects of physiology. CA proteins that are secreted proteins are particularly preferred in the present invention as they serve as good targets for diagnostic markers, for example for blood tests.

An CA sequence is initially identified by substantial nucleic acid and/or amino acid sequence homology to the CA sequences outlined herein. Such homology can be based upon the overall nucleic acid or amino acid sequence, and is generally determined as outlined below, using either homology programs or hybridization conditions.

As used herein, a nucleic acid is a "CA nucleic acid" if the overall homology of the nucleic acid sequence to one of the nucleic acids of Table 1 06-001 to 06-343 is preferably greater than about 75%, more preferably greater than about 80%, even more preferably greater than about 85% and most preferably greater than 90%. In some embodiments the homology will be as high as about 93 to 95 or 98%. In a preferred embodiment, the sequences which are used to determine sequence identity or similarity are selected from those of the nucleic acids of Table 1 06-001 to 06-343. In another embodiment, the sequences are naturally occurring allelic variants of the sequences of the nucleic acids of Table 1 06-001 to 06-343. In another embodiment, the sequences are sequence variants as further described herein.

Homology in this context means sequence similarity or identity, with identity being preferred. A preferred comparison for homology purposes is to compare the sequence containing sequencing errors to the correct sequence. This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., Methods in Enzymology, 266: 460-480 (1996); http://blast.wustl]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the nucleic acids of Table 1 06-001 to 06-343. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleotides than those of the nucleic acids of Table 1 06-001 to 06-343, it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

In one embodiment, the nucleic acid homology is determined through hybridization studies. Thus, for example, nucleic acids which hybridize under high stringency to the nucleic acids identified in the figures, or their complements, are considered CA sequences. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

In addition, the CA nucleic acid sequences of the invention are fragments of larger genes, i.e. they are nucleic acid segments. Alternatively, the CA nucleic acid sequences can serve as indicators of oncogene position, for example, the CA sequence may be an enhancer that activates a protooncogene. "Genes" in this context includes coding regions, non-coding regions, and mixtures of coding and non-coding regions. Accordingly, as will be appreciated by those in the art, using the sequences provided herein, additional sequences of the CA genes can be obtained, using techniques well known in the art for cloning either longer sequences or the full length sequences; see Maniatis et al., and Ausubel, et al., supra, hereby expressly incorporated by reference. In general, this is done using PCR, for example, kinetic PCR.

Once the CA nucleic acid is identified, it can be cloned and, if necessary, its constituent parts recombined to form the entire CA nucleic acid. Once isolated from its natural source, e.g., contained within a plasmid or other vector or excised therefrom as a linear nucleic acid segment, the recombinant CA nucleic acid can be further used as a probe to identify and isolate other CA nucleic acids, for example additional coding regions. It can also be used as a "precursor" nucleic acid to make modified or variant CA nucleic acids and proteins.

The CA nucleic acids of the present invention are used in several ways. In a first embodiment, nucleic acid probes to the CA nucleic acids are made and attached to biochips to be used in screening and diagnostic methods, as outlined below, or for administration, for example for gene therapy and/or antisense applications. Alternatively, the CA nucleic acids that include coding regions of CA proteins can be put into expression vectors for the expression of CA proteins, again either for screening purposes or for administration to a patient.

In a preferred embodiment, nucleic acid probes to CA nucleic acids (both the nucleic acid sequences outlined in the figures and/or the complements thereof) are made. The nucleic acid probes attached to the biochip are designed to be substantially complementary to the CA nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally whole genes are not used. In some embodiments, much longer nucleic acids can be used, up to hundreds of bases.

In a preferred embodiment, more than one probe per sequence is used, with either overlapping probes or probes to different sections of the target being used. That is, two, three, four or more probes, with three being preferred, are used to build in a redundancy for a particular target. The probes can be overlapping (i.e. have some sequence in common), or separate.

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, resins, silica or silica-based materials including silicon and modified silicon, carbon, metals, inorganic glasses, etc. In general, the substrates allow optical detection and do not appreciably fluoresce.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference). In addition, in some cases, additional linkers, such as alkyl groups (including substituted and heteroalkyl groups) may be used.

In this embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affymetrix GeneChip technology.

In addition to the solid-phase technology represented by biochip arrays, gene expression can also be quantified using liquid-phase arrays. One such system is kinetic polymerase chain reaction (PCR). Kinetic PCR allows for the simultaneous amplification and quantification of specific nucleic acid sequences. The specificity is derived from synthetic oligonucleotide primers designed to preferentially adhere to single-stranded nucleic acid sequences bracketing the target site. This pair of oligonucleotide primers form specific, non-covalently bound complexes on each strand of the target sequence. These complexes facilitate in vitro transcription of double-stranded DNA in opposite orientations. Temperature cycling of the reaction mixture creates a continuous cycle of primer binding, transcription, and re-melting of the nucleic acid to individual strands. The result is an exponential increase of the target dsDNA product. This product can be quantified in real time either through the use of an intercalating dye or a sequence specific probe. SYBR® Greene I, is an example of an intercalating dye, that preferentially binds to dsDNA resulting in a concomitant increase in the fluorescent signal. Sequence specific probes, such as used with TaqMan® technology, consist of a fluorochrome and a quenching molecule covalently bound to opposite ends of an oligonucleotide. The probe is designed to selectively bind the target DNA sequence between the two primers. When the DNA strands are synthesized during the PCR reaction, the fluorochrome is cleaved from the probe by the exonuclease activity of the polymerase resulting in signal dequenching. The probe signaling method can be more specific than the intercalating dye method, but in each case, signal strength is proportional to the dsDNA product produced. Each type of quantification method can be used in multi-well liquid phase arrays with each well representing primers and/or probes specific to nucleic acid sequences of interest. When used with messenger RNA preparations of tissues or cell lines, and an array of probe/primer reactions can simultaneously quantify the expression of multiple gene products of interest. See Germer, S., et al., Genome Res. 10:258-266 (2000); Heid, C. A., et al., Genome Res. 6, 986-994 (1996).

In a preferred embodiment, CA nucleic acids encoding CA proteins are used to make a variety of expression vectors to express CA proteins which can then be used in screening assays, as described below. The expression vectors may be either self-replicating extrachromosomal vectors or vectors which integrate into a host genome. Generally, these expression vectors include transcriptional and translational regulatory nucleic acid operably linked to the nucleic acid encoding the CA protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice. The transcriptional and translational regulatory nucleic acid will generally be appropriate to the host cell used to express the CA protein; for example, transcriptional and translational regulatory nucleic acid sequences from *Bacillus* are preferably used to express the CA protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The CA proteins of the present invention are produced by culturing a host cell transformed with an expression vector containing nucleic acid encoding an CA protein, under the appropriate conditions to induce or cause expression of the CA protein. The conditions appropriate for CA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect, plant and animal cells, including mammalian cells. Of particular interest are *Drosophila melanogaster* cells, *Saccharomyces cerevisiae* and other yeasts, *E. coli, Bacillus subtilis*, Sf9 cells, C129 cells, 293 cells, *Neurospora*, BHK, CHO, COS, HeLa cells, THP1 cell line (a macrophage cell line) and human cells and cell lines.

In a preferred embodiment, the CA proteins are expressed in mammalian cells. Mammalian expression systems are also known in the art, and include retroviral systems. A preferred expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, CA proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the CA protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

In one embodiment, CA proteins are produced in insect cells. Expression vectors for the transformation of insect cells, and in particular, baculovirus-based expression vectors, are well known in the art.

In a preferred embodiment, CA protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

The CA protein may also be made as a fusion protein, using techniques well known in the art. Thus, for example, for the creation of monoclonal antibodies. If the desired epitope is small, the CA protein may be fused to a carrier protein to form an immunogen. Alternatively, the CA protein may be made as a fusion protein to increase expression, or for other reasons. For example, when the CA protein is an CA peptide, the nucleic acid encoding the peptide may be linked to other nucleic acid for expression purposes.

In one embodiment, the CA nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b)

immune labels, which may be antibodies or antigens; and c) colored or fluorescent dyes. The labels may be incorporated into the CA nucleic acids, proteins and antibodies at any position. For example, the label should be capable of producing, either directly or indirectly, a detectable signal. The detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982).

Accordingly, the present invention also provides CA protein sequences. An CA protein of the present invention may be identified in several ways. "Protein" in this sense includes proteins, polypeptides, and peptides. As will be appreciated by those in the art, the nucleic acid sequences of the invention can be used to generate protein sequences. There are a variety of ways to do this, including cloning the entire gene and verifying its frame and amino acid sequence, or by comparing it to known sequences to search for homology to provide a frame, assuming the CA protein has homology to some protein in the database being used. Generally, the nucleic acid sequences are input into a program that will search all three frames for homology. This is done in a preferred embodiment using the following NCBI Advanced BLAST parameters. The program is blastx or blastn. The database is nr. The input data is as "Sequence in FASTA format". The organism list is "none". The "expect" is 10; the filter is default. The "descriptions" is 500, the "alignments" is 500, and the "alignment view" is pairwise. The "query Genetic Codes" is standard (1). The matrix is BLOSUM62; gap existence cost is 11, per residue gap cost is 1; and the lambda ratio is 0.85 default. This results in the generation of a putative protein sequence.

Also included within one embodiment of CA proteins are amino acid variants of the naturally occurring sequences, as determined herein. Preferably, the variants are preferably greater than about 75% homologous to the wild-type sequence, more preferably greater than about 80%, even more preferably greater than about 85% and most preferably greater than about 90%. In some embodiments the homology will be as high as about 93 to 95 or 98%. As for nucleic acids, homology in this context means sequence similarity or identity, with identity being preferred. This homology will be determined using standard techniques known in the art as are outlined above for the nucleic acid homologies.

CA proteins of the present invention may be shorter or longer than the wild type amino acid sequences. Thus, in a preferred embodiment, included within the definition of CA proteins are portions or fragments of the wild type sequences herein. In addition, as outlined above, the CA nucleic acids of the invention may be used to obtain additional coding regions, and thus additional protein sequence, using techniques known in the art.

In a preferred embodiment, the CA proteins are derivative or variant CA proteins as compared to the wild-type sequence. That is, as outlined more fully below, the derivative CA peptide will contain at least one amino acid substitution, deletion or insertion, with amino acid substitutions being particularly preferred. The amino acid substitution, insertion or deletion may occur at any residue within the CA peptide.

Also included in an embodiment of CA proteins of the present invention are amino acid sequence variants. These variants fall into one or more of three classes: substitutional, insertional or deletional variants. These variants ordinarily are prepared by site specific mutagenesis of nucleotides in the DNA encoding the CA protein, using cassette or PCR mutagenesis or other techniques well known in the art, to produce DNA encoding the variant, and thereafter expressing the DNA in recombinant cell culture as outlined above. However, variant CA protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the CA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed CA variants screened for the optimal combination of desired activity. Techniques for making substitution mutations at predetermined sites in DNA having a known sequence are well known, for example, M13 primer mutagenesis and LAR mutagenesis. Screening of the mutants is done using assays of CA protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the CA protein are desired, substitutions are generally made in accordance with the following chart:

| Chart I | |
|---|---|
| Original Residue | Exemplary Substitutions |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the CA proteins as needed. Alternatively, the variant may be designed such that the biological activity of the CA protein is altered. For example, glycosylation sites may be altered or removed, dominant negative mutations created, etc.

Covalent modifications of CA polypeptides are included within the scope of this invention, for example for use in screening. One type of covalent modification includes reacting targeted amino acid residues of an CA polypeptide with an organic derivatizing agent that is capable of reacting with selected side chains or the N- or C-terminal residues of an CA polypeptide. Derivatization with bifunctional agents is useful, for instance, for crosslinking CA polypeptides to a water-insoluble support matrix or surface for use in the method for purifying anti-CA antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the a-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of the CA polypeptide included within the scope of this invention comprises altering the native glycosylation pattern of the polypeptide. "Altering the native glycosylation pattern" is intended for purposes herein to mean deleting one or more carbohydrate moieties found in native sequence CA polypeptide, and/or adding one or more glycosylation sites that are not present in the native sequence CA polypeptide.

Addition of glycosylation sites to CA polypeptides may be accomplished by altering the amino acid sequence thereof. The alteration may be made, for example, by the addition of, or substitution by, one or more serine or threonine residues to the native sequence CA polypeptide (for O-linked glycosylation sites). The CA amino acid sequence may optionally be altered through changes at the DNA level, particularly by mutating the DNA encoding the CA polypeptide at preselected bases such that codons are generated that will translate into the desired amino acids.

Another means of increasing the number of carbohydrate moieties on the CA polypeptide is by chemical or enzymatic coupling of glycosides to the polypeptide. Such methods are described in the art, e.g., in WO 87/05330 published Sep. 11, 1987, and in Aplin and Wriston, L A Crit. Rev. Biochem., pp. 259-306 (1981).

Removal of carbohydrate moieties present on the CA polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of CA comprises linking the CA polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

CA polypeptides of the present invention may also be modified in a way to form chimeric molecules comprising an CA polypeptide fused to another, heterologous polypeptide or amino acid sequence. In one embodiment, such a chimeric molecule comprises a fusion of an CA polypeptide with a tag polypeptide which provides an epitope to which an anti-tag antibody can selectively bind. The epitope tag is generally placed at the amino- or carboxyl-terminus of the CA polypeptide, although internal fusions may also be tolerated in some instances. The presence of such epitope-tagged forms of an CA polypeptide can be detected using an antibody against the tag polypeptide. Also, provision of the epitope tag enables the CA polypeptide to be readily purified by affinity purification using an anti-tag antibody or another type of affinity matrix that binds to the epitope tag. In an alternative embodiment, the chimeric molecule may comprise a fusion of an CA polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87:6393-6397 (1990)].

Also included with the definition of CA protein in one embodiment are other CA proteins of the CA family, and CA proteins from other organisms, which are cloned and expressed as outlined below. Thus, probe or degenerate polymerase chain reaction (PCR) primer sequences may be used to find other related CA proteins from humans or other organisms. As will be appreciated by those in the art, particularly useful probe and/or PCR primer sequences include the unique areas of the CA nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art.

In addition, as is outlined herein, CA proteins can be made that are longer than those encoded by the nucleic acids of the figures, for example, by the elucidation of additional sequences, the addition of epitope or purification tags, the addition of other fusion sequences, etc.

CA proteins may also be identified as being encoded by CA nucleic acids. Thus, CA proteins are encoded by nucleic acids that will hybridize to the sequences of the sequence listings, or their complements, as outlined herein.

In a preferred embodiment, the invention provides CA antibodies. In a preferred embodiment, when the CA protein is to be used to generate antibodies, for example for immunotherapy, the CA protein should share at least one epitope or determinant with the full length protein. By "epitope" or "determinant" herein is meant a portion of a protein which will generate and/or bind an antibody or T-cell receptor in the context of MHC. Thus, in most instances, antibodies made to a smaller CA protein will be able to bind to the full length protein. In a preferred embodiment, the epitope is unique; that is, antibodies generated to a unique epitope show little or no cross-reactivity.

In one embodiment, the term "antibody" includes antibody fragments, as are known in the art, including Fab, $Fab_2$, single chain antibodies (Fv for example), chimeric antibodies, etc., either produced by the modification of whole antibodies or those synthesized de novo using recombinant DNA technologies.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by a nucleic acid of Table 1 06-001 to 06-343, or fragment thereof or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispecific antibodies. Bispecific antibodies are monoclonal, preferably human or humanized, antibodies that have binding specificities for at least two different antigens. In the present case, one of the binding specificities is for a protein encoded by a nucleic acid of Table 1 06-001 to 06-343, or a fragment thereof, the other one is for any other antigen, and preferably for a cell-surface protein or receptor or receptor subunit, preferably one that is tumor specific.

In a preferred embodiment, the antibodies to CA are capable of reducing or eliminating the biological function of CA, as is described below. That is, the addition of anti-CA antibodies (either polyclonal or preferably monoclonal) to CA (or cells containing CA) may reduce or eliminate the CA activity. Generally, at least a 25% decrease in activity is preferred, with at least about 50% being particularly preferred and about a 95-100% decrease being especially preferred.

In a preferred embodiment the antibodies to the CA proteins are humanized antibodies. Humanized forms of non-human (e.g., murine) antibodies are chimeric molecules of immunoglobulins, immunoglobulin chains or fragments thereof (such as Fv, Fab, Fab', $F(ab')_2$ or other antigen binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework residues (FR) regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies [Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

By immunotherapy is meant treatment of a carcinoma with an antibody raised against an CA protein. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen.

In a preferred embodiment, oncogenes which encode secreted growth factors may be inhibited by raising antibodies against CA proteins that are secreted proteins as described above. Without being bound by theory, antibodies used for treatment, bind and prevent the secreted protein from binding to its receptor, thereby inactivating the secreted CA protein.

In another preferred embodiment, the CA protein to which antibodies are raised is a transmembrane protein. Without being bound by theory, antibodies used for treatment, bind the extracellular domain of the CA protein and prevent it from binding to other proteins, such as circulating ligands or cell-associated molecules. The antibody may cause down-regulation of the transmembrane CA protein. As will be appreciated by one of ordinary skill in the art, the antibody may be a competitive, non-competitive or uncompetitive inhibitor of protein binding to the extracellular domain of the CA protein. The antibody is also an antagonist of the CA protein. Further, the antibody prevents activation of the transmembrane CA protein. In one aspect, when the antibody prevents the binding of other molecules to the CA protein, the antibody prevents growth of the cell. The antibody may also sensitize the cell to cytotoxic agents, including, but not limited to TNF-α, TNF-β, IL-1, INF-γ and IL-2, or chemotherapeutic agents including 5FU, vinblastine, actinomycin D, cisplatin, methotrexate, and the like. In some instances the antibody belongs to a sub-type that activates serum complement when complexed with the transmembrane protein thereby mediating cytotoxicity. Thus, carcinomas may be treated by administering to a patient antibodies directed against the transmembrane CA protein.

In another preferred embodiment, the antibody is conjugated to a therapeutic moiety. In one aspect the therapeutic moiety is a small molecule that modulates the activity of the CA protein. In another aspect the therapeutic moiety modulates the activity of molecules associated with or in close proximity to the CA protein. The therapeutic moiety may inhibit enzymatic activity such as protease or protein kinase activity associated with carcinoma.

In a preferred embodiment, the therapeutic moiety may also be a cytotoxic agent. In this method, targeting the cytotoxic agent to tumor tissue or cells, results in a reduction in the number of afflicted cells, thereby reducing symptoms associated with carcinomas, including lymphoma. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against CA proteins, or binding of a radionuclide to a chelating agent that has been covalently attached to the antibody. Targeting the therapeutic moiety to transmembrane CA proteins not only serves to increase the local concentration of therapeutic moiety in the carcinoma of interest, i.e., lymphoma, but also serves to reduce deleterious side effects that may be associated with the therapeutic moiety.

In another preferred embodiment, the CA protein against which the antibodies are raised is an intracellular protein. In this case, the antibody may be conjugated to a protein which facilitates entry into the cell. In one case, the antibody enters the cell by endocytosis. In another embodiment, a nucleic acid encoding the antibody is administered to the individual or cell. Moreover, wherein the CA protein can be targeted within a cell, i.e., the nucleus, an antibody thereto contains a signal for that target localization, i.e., a nuclear localization signal.

The CA antibodies of the invention specifically bind to CA proteins. By "specifically bind" herein is meant that the antibodies bind to the protein with a binding constant in the range of at least $10^{-4}$-$10^{-6}$ M$^{-1}$, with a preferred range being $10^{-7}$-$10^{-9}$ M$^{-1}$.

In a preferred embodiment, the CA protein is purified or isolated after expression. CA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the CA protein may be purified using a standard anti-CA antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the CA protein. In some instances no purification will be necessary.

Once expressed and purified if necessary, the CA proteins and nucleic acids are useful in a number of applications.

In one aspect, the expression levels of genes are determined for different cellular states in the carcinoma phenotype; that is, the expression levels of genes in normal tissue and in carcinoma tissue (and in some cases, for varying severities of lymphoma that relate to prognosis, as outlined below) are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or carcinoma tissue.

"Differential expression," or grammatical equivalents as used herein, refers to both qualitative as well as quantitative differences in the genes temporal and/or cellular expression patterns within and among the cells. Thus, a differentially expressed gene can qualitatively have its expression altered, including an activation or inactivation, in, for example, normal versus carcinoma tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip® expression arrays, Lockhart, Nature Biotechnology, 14:1675-1680 (1996), hereby expressly incorporated by reference. Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the CA protein and standard immunoassays (ELISAs, etc.) or other techniques, including mass spectroscopy assays, 2D gel electrophoresis assays, etc. Thus, the proteins corresponding to CA genes, i.e. those identified as being important in a particular carcinoma phenotype, i.e., lymphoma, can be evaluated in a diagnostic test specific for that carcinoma.

In a preferred embodiment, gene expression monitoring is done and a number of genes, i.e. an expression profile, is monitored simultaneously, although multiple protein expression monitoring can be done as well. Similarly, these assays may be done on an individual basis as well.

In this embodiment, the CA nucleic acid probes may be attached to biochips as outlined herein for the detection and quantification of CA sequences in a particular cell. The assays are done as is known in the art. As will be appreciated by those in the art, any number of different CA sequences may be used as probes, with single sequence assays being used in some cases, and a plurality of the sequences described herein being used in other embodiments. In addition, while solid-phase assays are described, any number of solution based assays may be done as well.

In a preferred embodiment, both solid and solution based assays may be used to detect CA sequences that are up-regulated or down-regulated in carcinomas as compared to normal tissue. In instances where the CA sequence has been altered but shows the same expression profile or an altered expression profile, the protein will be detected as outlined herein.

In a preferred embodiment nucleic acids encoding the CA protein are detected. Although DNA or RNA encoding the CA protein may be detected, of particular interest are methods wherein the mRNA encoding a CA protein is detected. The presence of mRNA in a sample is an indication that the CA gene has been transcribed to form the mRNA, and suggests that the protein is expressed. Probes to detect the mRNA can be any nucleotide/deoxynucleotide probe that is complementary to and base pairs with the mRNA and includes but is not limited to oligonucleotides, cDNA or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a CA protein is detected by binding the digoxygenin with an anti-digoxygenin secondary antibody and developed with nitro blue tetrazolium and 5-bromo-4-chloro-3-indoyl phosphate.

In a preferred embodiment, any of the three classes of proteins as described herein (secreted, transmembrane or intracellular proteins) are used in diagnostic assays. The CA proteins, antibodies, nucleic acids, modified proteins and cells containing CA sequences are used in diagnostic assays. This can be done on an individual gene or corresponding polypeptide level, or as sets of assays.

As described and defined herein, CA proteins find use as markers of carcinomas, including lymphomas such as, but not limited to, Hodgkin's and non-Hodgkin lymphoma. Detection of these proteins in putative carcinoma tissue or patients allows for a determination or diagnosis of the type of carcinoma. Numerous methods known to those of ordinary skill in the art find use in detecting carcinomas. In one embodiment, antibodies are used to detect CA proteins. A preferred method separates proteins from a sample or patient by electrophoresis on a gel (typically a denaturing and reducing protein gel, but may be any other type of gel including isoelectric focusing gels and the like). Following separation of proteins, the CA protein is detected by immunoblotting with antibodies raised against the CA protein. Methods of immunoblotting are well known to those of ordinary skill in the art.

In another preferred method, antibodies to the CA protein find use in in situ imaging techniques. In this method cells are contacted with from one to many antibodies to the CA protein(s). Following washing to remove non-specific antibody binding, the presence of the antibody or antibodies is detected. In one embodiment the antibody is detected by incubating with a secondary antibody that contains a detectable label. In another method the primary antibody to the CA protein(s) contains a detectable label. In another preferred embodiment each one of multiple primary antibodies contains a distinct and detectable label. This method finds particular use in simultaneous screening for a plurality of CA proteins. As will be appreciated by one of ordinary skill in the art, numerous other histological imaging techniques are useful in the invention.

In a preferred embodiment the label is detected in a fluorometer which has the ability to detect and distinguish emissions of different wavelengths. In addition, a fluorescence activated cell sorter (FACS) can be used in the method.

In another preferred embodiment, antibodies find use in diagnosing carcinomas from blood samples. As previously described, certain CA proteins are secreted/circulating molecules. Blood samples, therefore, are useful as samples to be probed or tested for the presence of secreted CA proteins. Antibodies can be used to detect the CA proteins by any of the previously described immunoassay techniques including ELISA, immunoblotting (Western blotting), immunoprecipitation, BIACORE technology and the like, as will be appreciated by one of ordinary skill in the art.

In a preferred embodiment, in situ hybridization of labeled CA nucleic acid probes to tissue arrays is done. For example, arrays of tissue samples, including CA tissue and/or normal tissue, are made. In situ hybridization as is known in the art can then be done.

It is understood that when comparing the expression fingerprints between an individual and a standard, the skilled artisan can make a diagnosis as well as a prognosis. It is further understood that the genes which indicate the diagnosis may differ from those which indicate the prognosis.

In a preferred embodiment, the CA proteins, antibodies, nucleic acids, modified proteins and cells containing CA sequences are used in prognosis assays. As above, gene expression profiles can be generated that correlate to carcinoma, especially lymphoma, severity, in terms of long term prognosis. Again, this may be done on either a protein or gene level, with the use of genes being preferred. As above, the CA probes are attached to biochips for the detection and quantification of CA sequences in a tissue or patient. The assays proceed as outlined for diagnosis.

In a preferred embodiment, any of the CA sequences as described herein are used in drug screening assays. The CA proteins, antibodies, nucleic acids, modified proteins and cells containing CA sequences are used in drug screening assays or by evaluating the effect of drug candidates on a "gene expression profile" or expression profile of polypeptides. In one embodiment, the expression profiles are used, preferably in conjunction with high throughput screening techniques to allow monitoring for expression profile genes after treatment with a candidate agent, Zlokarnik, et al., Science 279, 84-8 (1998), Heid, et al., Genome Res., 6:986-994 (1996).

In a preferred embodiment, the CA proteins, antibodies, nucleic acids, modified proteins and cells containing the native or modified CA proteins are used in screening assays. That is, the present invention provides novel methods for screening for compositions which modulate the carcinoma phenotype. As above, this can be done by screening for modulators of gene expression or for modulators of protein activity. Similarly, this may be done on an individual gene or protein level or by evaluating the effect of drug candidates on a "gene expression profile". In a preferred embodiment, the expression profiles are used, preferably in conjunction with high throughput screening techniques to allow monitoring for expression profile genes after treatment with a candidate agent, see Zlokarnik, supra.

Having identified the CA genes herein, a variety of assays to evaluate the effects of agents on gene expression may be executed. In a preferred embodiment, assays may be run on an individual gene or protein level. That is, having identified a particular gene as aberrantly regulated in carcinoma, candidate bioactive agents may be screened to modulate the genes response. "Modulation" thus includes both an increase and a decrease in gene expression or activity. The preferred amount of modulation will depend on the original change of the gene expression in normal versus tumor tissue, with changes of at least 10%, preferably 50%, more preferably 100-300%, and in some embodiments 300-1000% or greater. Thus, if a gene exhibits a 4 fold increase in tumor compared to normal tissue, a decrease of about four fold is desired; a 10 fold decrease in tumor compared to normal tissue gives a 10 fold increase in expression for a candidate agent is desired, etc. Alternatively, where the CA sequence has been altered but shows the same expression profile or an altered expression profile, the protein will be detected as outlined herein.

As will be appreciated by those in the art, this may be done by evaluation at either the gene or the protein level; that is, the amount of gene expression may be monitored using nucleic acid probes and the quantification of gene expression levels, or, alternatively, the level of the gene product itself can be monitored, for example through the use of antibodies to the CA protein and standard immunoassays. Alternatively, binding and bioactivity assays with the protein may be done as outlined below.

In a preferred embodiment, gene expression monitoring is done and a number of genes, i.e. an expression profile, is monitored simultaneously, although multiple protein expression monitoring can be done as well.

In this embodiment, the CA nucleic acid probes are attached to biochips as outlined herein for the detection and quantification of CA sequences in a particular cell. The assays are further described below.

Generally, in a preferred embodiment, a candidate bioactive agent is added to the cells prior to analysis. Moreover, screens are provided to identify a candidate bioactive agent which modulates a particular type of carcinoma, modulates CA proteins, binds to a CA protein, or interferes between the binding of a CA protein and an antibody.

The term "candidate bioactive agent" or "drug candidate" or grammatical equivalents as used herein describes any molecule, e.g., protein, oligopeptide, small organic or inorganic molecule, polysaccharide, polynucleotide, etc., to be tested for bioactive agents that are capable of directly or indirectly altering either the carcinoma phenotype, binding to and/or modulating the bioactivity of an CA protein, or the expression of a CA sequence, including both nucleic acid sequences and protein sequences. In a particularly preferred embodiment, the candidate agent suppresses a CA phenotype, for example to a normal tissue fingerprint. Similarly, the candidate agent preferably suppresses a severe CA phenotype. Generally a plurality of assay mixtures are run in parallel with different agent concentrations to obtain a differential response to the various concentrations. Typically, one of these concentrations serves as a negative control, i.e., at zero concentration or below the level of detection.

In one aspect, a candidate agent will neutralize the effect of an CA protein. By "neutralize" is meant that activity of a protein is either inhibited or counter acted against so as to have substantially no effect on a cell.

Candidate agents encompass numerous chemical classes, though typically they are organic or inorganic molecules, preferably small organic compounds having a molecular weight of more than 100 and less than about 2,500 daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids, as defined above.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

In assays for altering the expression profile of one or more CA genes, after the candidate agent has been added and the cells allowed to incubate for some period of time, the sample containing the target sequences to be analyzed is added to the biochip. If required, the target sequence is prepared using known techniques. For example, the sample may be treated to lyse the cells, using known lysis buffers, electroporation, etc., with purification and/or amplification such as PCR occurring as needed, as will be appreciated by those in the art. For example, an in vitro transcription with labels covalently attached to the nucleosides is done. Generally, the nucleic acids are labeled with a label as defined herein, with biotin-FITC or PE, cy3 and cy5 being particularly preferred.

In a preferred embodiment, the target sequence is labeled with, for example, a fluorescent, chemiluminescent, chemical, or radioactive signal, to provide a means of detecting the target sequence's specific binding to a probe. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin.

For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. In this embodiment, in general, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target. In addition, either solid phase or solution based (i.e., kinetic PCR) assays may be used.

Once the assay is run, the data is analyzed to determine the expression levels, and changes in expression levels as between states, of individual genes, forming a gene expression profile.

In a preferred embodiment, as for the diagnosis and prognosis applications, having identified the differentially expressed gene(s) or mutated gene(s) important in any one state, screens can be run to alter the expression of the genes individually. That is, screening for modulation of regulation of expression of a single gene can be done. Thus, for example, particularly in the case of target genes whose presence or absence is unique between two states, screening is done for modulators of the target gene expression.

In addition, screens can be done for novel genes that are induced in response to a candidate agent. After identifying a candidate agent based upon its ability to suppress a CA expression pattern leading to a normal expression pattern, or modulate a single CA gene expression profile so as to mimic the expression of the gene from normal tissue, a screen as described above can be performed to identify genes that are specifically modulated in response to the agent. Comparing expression profiles between normal tissue and agent treated CA tissue reveals genes that are not expressed in normal tissue or CA tissue, but are expressed in agent treated tissue. These agent specific sequences can be identified and used by any of the methods described herein for CA genes or proteins. In particular these sequences and the proteins they encode find use in marking or identifying agent treated cells. In addition, antibodies can be raised against the agent induced proteins and used to target novel therapeutics to the treated CA tissue sample.

Thus, in one embodiment, a candidate agent is administered to a population of CA cells, that thus has an associated CA expression profile. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e. a peptide) may be put into a viral construct such as a retroviral construct and added to the cell, such that expression of the peptide agent is accomplished; see PCT US97/01019, hereby expressly incorporated by reference.

Once the candidate agent has been administered to the cells, the cells can be washed if desired and are allowed to incubate under preferably physiological conditions for some period of time. The cells are then harvested and a new gene expression profile is generated, as outlined herein.

Thus, for example, CA tissue may be screened for agents that reduce or suppress the CA phenotype. A change in at least one gene of the expression profile indicates that the agent has an effect on CA activity. By defining such a signature for the CA phenotype, screens for new drugs that alter the phenotype can be devised. With this approach, the drug target need not be known and need not be represented in the original expression screening platform, nor does the level of transcript for the target protein need to change.

In a preferred embodiment, as outlined above, screens may be done on individual genes and gene products (proteins). That is, having identified a particular differentially expressed gene as important in a particular state, screening of modulators of either the expression of the gene or the gene product itself can be done. The gene products of differentially expressed genes are sometimes referred to herein as "CA proteins" or an "CAP". The CAP may be a fragment, or alternatively, be the full length protein to the fragment encoded by the nucleic acids of Table 1 06-001 to 06-343. Preferably, the CAP is a fragment. In another embodiment, the sequences are sequence variants as further described herein.

Preferably, the CAP is a fragment of approximately 14 to 24 amino acids long. More preferably the fragment is a soluble fragment. Preferably, the fragment includes a non-transmembrane region. In a preferred embodiment, the fragment has an N-terminal Cys to aid in solubility. In one embodiment, the c-terminus of the fragment is kept as a free acid and the n-terminus is a free amine to aid in coupling, i.e., to cysteine.

In one embodiment the CA proteins are conjugated to an immunogenic agent as discussed herein. In one embodiment the CA protein is conjugated to BSA.

In a preferred embodiment, screening is done to alter the biological function of the expression product of the CA gene. Again, having identified the importance of a gene in a particular state, screening for agents that bind and/or modulate the biological activity of the gene product can be run as is more fully outlined below.

In a preferred embodiment, screens are designed to first find candidate agents that can bind to CA proteins, and then these agents may be used in assays that evaluate the ability of the candidate agent to modulate the CAP activity and the carcinoma phenotype. Thus, as will be appreciated by those in the art, there are a number of different assays which may be run; binding assays and activity assays.

In a preferred embodiment, binding assays are done. In general, purified or isolated gene product is used; that is, the gene products of one or more CA nucleic acids are made. In general, this is done as is known in the art. For example, antibodies are generated to the protein gene products, and standard immunoassays are run to determine the amount of protein present. Alternatively, cells comprising the CA proteins can be used in the assays.

Thus, in a preferred embodiment, the methods comprise combining a CA protein and a candidate bioactive agent, and determining the binding of the candidate agent to the CA protein. Preferred embodiments utilize the human or mouse CA protein, although other mammalian proteins may also be used, for example for the development of animal models of human disease. In some embodiments, as outlined herein, variant or derivative CA proteins may be used.

Generally, in a preferred embodiment of the methods herein, the CA protein or the candidate agent is non-diffusably bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In a preferred embodiment, the CA protein is bound to the support, and a candidate bioactive agent is added to the assay. Alternatively, the candidate agent is bound to the support and the CA protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the CA protein may be done in a number of ways. In a preferred embodiment, the candidate bioactive agent is labeled, and binding determined directly. For example, this may be done by attaching all or a portion of the CA protein to a solid support, adding a labeled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. CA protein), such as an antibody, peptide, binding partner, ligand, etc. Under certain circumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the CA protein and thus is capable of binding to, and potentially modulating, the activity of the CA protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the CA protein with a higher affinity. Thus, if the candidate bioactive agent is labeled, the presence of the label on the support, coupled with a lack of competitor binding, may indicate that the candidate agent is capable of binding to the CA protein.

In a preferred embodiment, the methods comprise differential screening to identity bioactive agents that are capable of modulating the activity of the CA proteins. In this embodiment, the methods comprise combining a CA protein and a competitor in a first sample. A second sample comprises a candidate bioactive agent, a CA protein and a competitor. The binding of the competitor is determined for both samples, and a change, or difference in binding between the two samples indicates the presence of an agent capable of binding to the CA protein and potentially modulating its activity. That is, if the binding of the competitor is different in the second sample relative to the first sample, the agent is capable of binding to the CA protein.

Alternatively, a preferred embodiment utilizes differential screening to identify drug candidates that bind to the native CA protein, but cannot bind to modified CA proteins. The structure of the CA protein may be modeled, and used in rational drug design to synthesize agents that interact with that site. Drug candidates that affect CA bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of CA proteins may also be done. In a preferred embodiment, methods for screening for a bioactive agent capable of modulating the activity of CA proteins comprise the steps of adding a candidate bioactive agent to a sample of CA proteins, as above, and determining an alteration in the biological activity of CA proteins. "Modulating the activity of an CA protein" includes an increase in activity, a decrease in activity, or a change in the type or kind of activity present. Thus, in this embodiment, the candidate agent should both bind to CA proteins (although this may not be necessary), and alter its biological or biochemical activity as defined herein. The methods include both in vitro screening methods, as are generally outlined above, and in vivo screening of cells for alterations in the presence, distribution, activity or amount of CA proteins.

Thus, in this embodiment, the methods comprise combining a CA sample and a candidate bioactive agent, and evaluating the effect on CA activity. By "CA activity" or grammatical equivalents herein is meant one of the CA protein's biological activities, including, but not limited to, its role in tumorigenesis, including cell division, preferably in lymphatic tissue, cell proliferation, tumor growth and transformation of cells. In one embodiment, CA activity includes activation of or by a protein encoded by a nucleic acid of Table 1 06-001 to 06-343. An inhibitor of CA activity is the inhibition of any one or more CA activities.

In a preferred embodiment, the activity of the CA protein is increased; in another preferred embodiment, the activity of the CA protein is decreased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of a CA protein. The methods comprise adding a candidate bioactive agent, as defined above, to a cell comprising CA proteins. Preferred cell types include almost any cell. The cells contain a recombinant nucleic acid that encodes a CA protein. In a preferred embodiment, a library of candidate agents are tested on a plurality of cells.

In one aspect, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

In this way, bioactive agents are identified. Compounds with pharmacological activity are able to enhance or interfere with the activity of the CA protein.

In one embodiment, a method of inhibiting carcinoma cancer cell division, is provided. The method comprises administration of a carcinoma cancer inhibitor.

In a preferred embodiment, a method of inhibiting lymphoma carcinoma cell division is provided comprising administration of a lymphoma carcinoma inhibitor.

In another embodiment, a method of inhibiting tumor growth is provided. The method comprises administration of a carcinoma cancer inhibitor. In a particularly preferred embodiment, a method of inhibiting tumor growth in lymphatic tissue is provided comprising administration of a lymphoma inhibitor.

In a further embodiment, methods of treating cells or individuals with cancer are provided. The method comprises administration of a carcinoma cancer inhibitor. Preferably, the carcinoma is a lymphoma carcinoma.

In one embodiment, a carcinoma cancer inhibitor is an antibody as discussed above. In another embodiment, the carcinoma cancer inhibitor is an antisense molecule. Antisense molecules as used herein include antisense or sense oligonucleotides comprising a singe-stranded nucleic acid sequence (either RNA or DNA) capable of binding to target mRNA (sense) or DNA (antisense) sequences for carcinoma cancer molecules. Antisense or sense oligonucleotides, according to the present invention, comprise a fragment generally at least about 14 nucleotides, preferably from about 14 to 30 nucleotides. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

Antisense molecules may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. It is understood that the use of antisense molecules or knock out and knock in models may also be used in screening assays as discussed above, in addition to methods of treatment.

The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1-100% wgt/vol. The agents may be administered alone or in combination with other treatments, i.e., radiation.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Without being bound by theory, it appears that the various CA sequences are important in carcinomas. Accordingly, disorders based on mutant or variant CA genes may be determined. In one embodiment, the invention provides methods for identifying cells containing variant CA genes comprising determining all or part of the sequence of at least one endogenous CA genes in a cell. As will be appreciated by those in the art, this may be done using any number of sequencing techniques. In a preferred embodiment, the invention provides methods of identifying the CA genotype of an individual comprising determining all or part of the sequence of at least one CA gene of the individual. This is generally done in at least one tissue of the individual, and may include the evaluation of a number of tissues or different samples of the same tissue. The method may include comparing the sequence of the sequenced CA gene to a known CA gene, i.e., a wild-type gene. As will be appreciated by those in the art, alterations in the sequence of some oncogenes can be an indication of either the presence of the disease, or propensity to develop the disease, or prognosis evaluations.

The sequence of all or part of the CA gene can then be compared to the sequence of a known CA gene to determine if any differences exist. This can be done using any number of known homology programs, such as Bestfit, etc. In a preferred embodiment, the presence of a difference in the sequence between the CA gene of the patient and the known CA gene is indicative of a disease state or a propensity for a disease state, as outlined herein.

In a preferred embodiment, the CA genes are used as probes to determine the number of copies of the CA gene in the genome. For example, some cancers exhibit chromosomal deletions or insertions, resulting in an alteration in the copy number of a gene.

In another preferred embodiment CA genes are used as probes to determine the chromosomal location of the CA genes. Information such as chromosomal location finds use in providing a diagnosis or prognosis in particular when chromosomal abnormalities such as translocations, and the like are identified in CA gene loci.

Thus, in one embodiment, methods of modulating CA in cells or organisms are provided. In one embodiment, the methods comprise administering to a cell an anti-CA antibody that reduces or eliminates the biological activity of an endogenous CA protein. Alternatively, the methods comprise administering to a cell or organism a recombinant nucleic acid encoding a CA protein. As will be appreciated by those in the art, this may be accomplished in any number of ways. In a preferred embodiment, for example when the CA sequence is down-regulated in carcinoma, the activity of the CA gene is increased by increasing the amount of CA in the cell, for example by overexpressing the endogenous CA or by administering a gene encoding the CA sequence, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety. Alternatively, for example when the CA sequence is up-regulated in carcinoma, the activity of the endogenous CA gene is decreased, for example by the administration of a CA antisense nucleic acid.

In one embodiment, the CA proteins of the present invention may be used to generate polyclonal and monoclonal antibodies to CA proteins, which are useful as described herein. Similarly, the CA proteins can be coupled, using standard technology, to affinity chromatography columns. These columns may then be used to purify CA antibodies. In a preferred embodiment, the antibodies are generated to epitopes unique to a CA protein; that is, the antibodies show little or no cross-reactivity to other proteins. These antibodies find use in a number of applications. For example, the CA antibodies may be coupled to standard affinity chromatography columns and used to purify CA proteins. The antibodies may also be used as blocking polypeptides, as outlined above, since they will specifically bind to the CA protein.

In one embodiment, a therapeutically effective dose of a CA or modulator thereof is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for CA degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the CA proteins and modulators of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the CA proteins and modulators may be directly applied as a solution or spray.

The pharmaceutical compositions of the present invention comprise a CA protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

In a preferred embodiment, CA proteins and modulators are administered as therapeutic agents, and can be formulated as outlined above. Similarly, CA genes (including both the full-length sequence, partial sequences, or regulatory sequences of the CA coding regions) can be administered in gene therapy applications, as is known in the art. These CA genes can include antisense applications, either as gene therapy (i.e. for incorporation into the genome) or as antisense compositions, as will be appreciated by those in the art.

In a preferred embodiment, CA genes are administered as DNA vaccines, either single genes or combinations of CA genes. Naked DNA vaccines are generally known in the art. Brower, Nature Biotechnology, 16:1304-1305 (1998).

In one embodiment, CA genes of the present invention are used as DNA vaccines. Methods for the use of genes as DNA vaccines are well known to one of ordinary skill in the art, and include placing a CA gene or portion of a CA gene under the control of a promoter for expression in a patient with carcinoma. The CA gene used for DNA vaccines can encode full-length CA proteins, but more preferably encodes portions of the CA proteins including peptides derived from the CA protein. In a preferred embodiment a patient is immunized with a DNA vaccine comprising a plurality of nucleotide sequences derived from a CA gene. Similarly, it is possible to immunize a patient with a plurality of CA genes or portions thereof as defined herein. Without being bound by theory, expression of the polypeptide encoded by the DNA vaccine, cytotoxic T-cells, helper T-cells and antibodies are induced which recognize and destroy or eliminate cells expressing CA proteins.

In a preferred embodiment, the DNA vaccines include a gene encoding an adjuvant molecule with the DNA vaccine. Such adjuvant molecules include cytokines that increase the immunogenic response to the CA polypeptide encoded by the DNA vaccine. Additional or alternative adjuvants are known to those of ordinary skill in the art and find use in the invention.

In another preferred embodiment CA genes find use in generating animal models of carcinomas, particularly lymphoma carcinomas. As is appreciated by one of ordinary skill in the art, when the CA gene identified is repressed or diminished in CA tissue, gene therapy technology wherein antisense RNA directed to the CA gene will also diminish or repress expression of the gene. An animal generated as such serves as an animal model of CA that finds use in screening bioactive drug candidates. Similarly, gene knockout technology, for example as a result of homologous recombination with an appropriate gene targeting vector, will result in the absence of the CA protein. When desired, tissue-specific expression or knockout of the CA protein may be necessary.

It is also possible that the CA protein is overexpressed in carcinoma. As such, transgenic animals can be generated that overexpress the CA protein. Depending on the desired expression level, promoters of various strengths can be employed to express the transgene. Also, the number of copies of the integrated transgene can be determined and compared for a determination of the expression level of the transgene. Animals generated by such methods find use as animal models of CA and are additionally useful in screening for bioactive molecules to treat carcinoma.

The CA nucleic acid sequences of the invention are depicted in Table 1 06-001 to 06-343. The sequences in each Table include genomic sequence, mRNA and protein sequences for both mouse and human. N/A indicates a gene that has been identified, but for which there has not been a name ascribed.

The sequences are found on the accompanying CD-ROM, the contents of which are expressly incorporated herein by reference. The file name is Table 1.txt. The file was created on Feb. 28, 2002 and saved on the CD-ROM on Mar. 1, 2002. The file contains 53,297 Kbytes.

LENGTHY TABLES

The patent contains a lengthy table section. A copy of the table is available in electronic form from the USPTO web site (http://seqdata.uspto.gov/?pageRequest=docDetail&DocID=US07892730B2). An electronic copy of the table will also be available from the USPTO upon request and payment of the fee set forth in 37 CFR 1.19(b)(3).

The names of the mouse and human genes are outlined below.

| | | |
|---|---|---|
| 06-001 | mCG10049 | hCG41676 |
| 06-002 | mCG10078 | hCG19413 |
| 06-003 | mCG10132 | hCG21567 |
| 06-004 | mCG10208 | hCG21073 |
| 06-005 | mCG10215 | hCG37475 |
| 06-006 | mCG10283 | hCG201153 |
| 06-007 | mCG10301 | hCG25637 |
| 06-008 | mCG10339 | hCG36720 |
| 06-009 | mCG10368 | hCG1777139 |
| 06-010 | mCG10474 | hCG1784975 |
| 06-011 | mCG10543 | hCG1776024 |
| 06-012 | mCG10583 | hCG1780788 |
| 06-013 | mCG1062 | hCG28127 |
| 06-014 | mCG10645 | hCG15849 |
| 06-015 | mCG10734 | hCG15249 |
| 06-016 | mCG10776 | hCG28722 |

-continued

| | | |
|---|---|---|
| 06-017 | mCG11034 | hCG26773 |
| 06-018 | mCG11078 | hCG1644496 |
| 06-019 | mCG11119 | hCG27363 |
| 06-020 | mCG11136 | hCG1782215 |
| 06-021 | mCG11291 | hCG1787835 |
| 06-022 | mCG11441 | hCG401177 |
| 06-023 | mCG11471 | hCG40117 |
| 06-024 | mCG11506 | hCG28011 |
| 06-025 | mCG11566 | hCG21793 |
| 06-026 | mCG11814 | hCG1775160 |
| 06-027 | mCG11829 | hCG37570 |
| 06-028 | mCG11914 | hCG1640505 |
| 06-029 | mCG11924 | hCG16317 |
| 06-030 | mCG11959 | hCG24311 |
| 06-031 | mCG1196 | hCG26669 |
| 06-032 | mCG12024 | hCG39093 |
| 06-033 | mCG12068 | hCG1787637 |
| 06-034 | mCG12133 | hCG23625 |
| 06-035 | mCG12182 | hCG40211 |
| 06-036 | mCG12368 | hCG1744883 |
| 06-037 | mCG12523 | hCG23847 |
| 06-038 | mCG12572 | hCG1778483 |
| 06-039 | mCG12663 | hCG37533 |
| 06-040 | mCG12673 | hCG1810774 |
| 06-041 | mCG12706 | hCG1643869 |
| 06-042 | mCG12722 | hCG33130 |
| 06-043 | mCG12724 | hCG33132 |
| 06-044 | mCG12746 | hCG30819 |
| 06-045 | mCG12792 | hCG24510 |
| 06-046 | mCG12872 | hCG23021 |
| 06-047 | mCG12945 | hCG1739154 |
| 06-048 | mCG13023 | hCG20125 |
| 06-049 | mCG13044 | hCG32359 |
| 06-050 | mCG13084 | hCG1735292 |
| 06-051 | mCG13312 | hCG14731 |
| 06-052 | mCG1338 | hCG32977 |
| 06-053 | mCG13395 | hCG22712 |
| 06-054 | mCG13466 | hCG38705 |
| 06-055 | mCG13520 | hCG15674 |
| 06-056 | mCG13636 | hCG36954 |
| 06-057 | mCG13896 | hCG40471 |
| 06-058 | mCG14020 | hCG1732038 |
| 06-059 | mCG14116 | hCG39199 |
| 06-060 | mCG14172 | hCG15529 |
| 06-061 | mCG1422 | hCG24418 |
| 06-062 | mCG14290 | hCG23314 |
| 06-063 | mCG14414 | hCG1641631 |
| 06-064 | mCG14521 | hCG23105 |
| 06-065 | mCG14555 | hCG23727 |
| 06-066 | mCG14611 | hCG38337 |
| 06-067 | mCG14624 | hCG32448 |
| 06-068 | mCG14659 | hCG23908 |
| 06-069 | mCG1468 | hCG32770 |
| 06-070 | mCG14749 | hCG16187 |
| 06-071 | mCG14817 | hCG17311 |
| 06-072 | mCG14883 | hCG1736594 |
| 06-073 | mCG14932 | hCG24749 |
| 06-074 | mCG14989 | hCG1646502 |
| 06-075 | mCG15039 | hCG28572 |
| 06-076 | mCG15044 | hCG27278 |
| 06-077 | mCG15048 | hCG28567 |
| 06-078 | mCG15184 | hCG1783275 |
| 06-079 | mCG15331 | hCG1640186 |
| 06-080 | mCG15379 | hCG1643838 |
| 06-081 | mCG15397 | hCG39530 |
| 06-082 | mCG15498 | hCG15009 |
| 06-083 | mCG15520 | hCG36837 |
| 06-084 | mCG15521 | hCG37331 |
| 06-085 | mCG15594 | hCG15786 |
| 06-086 | mCG15699 | hCG27588 |
| 06-087 | mCG15703 | hCG23995 |
| 06-088 | mCG15868 | hCG19397 |
| 06-089 | mCG15870 | hCG18268 |
| 06-090 | mCG1589 | hCG28214 |
| 06-091 | mCG1596 | hCG28803 |
| 06-092 | mCG15964 | hCG1762872 |
| 06-093 | mCG16052 | hCG15409 |
| 06-094 | mCG16071 | hCG23219 |
| 06-095 | mCG16088 | hCG33697 |
| 06-096 | mCG16239 | hCG21559 |
| 06-097 | mCG16291 | hCG1737652 |
| 06-098 | mCG16365 | hCG1640204 |
| 06-099 | mCG16394 | hCG20537 |
| 06-100 | mCG16401 | hCG20994 |
| 06-101 | mCG1647 | hCG25929 |
| 06-102 | mCG1659 | hCG32809 |
| 06-103 | mCG16601 | hCG17315 |
| 06-104 | mCG16720 | hCG18035 |
| 06-105 | mCG16843 | hCG37968 |
| 06-106 | mCG16845 | hCG37971 |
| 06-107 | mCG16880 | hCG22479 |
| 06-108 | mCG16923 | hCG25643 |
| 06-109 | mCG16959 | hCG25303 |
| 06-110 | mCG16994 | hCG36856 |
| 06-111 | mCG17013 | hCG24994 |
| 06-112 | mCG17035 | hCG1778746 |
| 06-113 | mCG17138 | hCG33187 |
| 06-114 | mCG17164 | hCG40741 |
| 06-115 | mCG17208 | hCG40378 |
| 06-116 | mCG17242 | hCG25680 |
| 06-117 | mCG17259 | hCG19476 |
| 06-118 | mCG17323 | hCG32158 |
| 06-119 | mCG17383 | hCG28354 |
| 06-120 | mCG17557 | hCG99255 |
| 06-121 | mCG17867 | hCG33515 |
| 06-122 | mCG17870 | hCG32959 |
| 06-123 | mCG17886 | hCG20908 |
| 06-124 | mCG17943 | hCG17932 |
| 06-125 | mCG17984 | hCG33404 |
| 06-126 | mCG18016 | hCG17121 |
| 06-127 | mCG18026 | hCG17346 |
| 06-128 | mCG18081 | hCG38701 |
| 06-129 | mCG18084 | hCG39597 |
| 06-130 | mCG18240 | hCG18999 |
| 06-131 | mCG1828 | hCG1640193 |
| 06-132 | mCG18281 | hCG16651 |
| 06-133 | mCG18404 | hCG20204 |
| 06-134 | mCG18525 | hCG15773 |
| 06-135 | mCG18554 | hCG18551 |
| 06-136 | mCG18573 | hCG18549 |
| 06-137 | mCG18577 | hCG28278 |
| 06-138 | mCG18584 | hCG20056 |
| 06-139 | mCG18590 | hCG21253 |
| 06-140 | mCG18632 | hCG19781 |
| 06-141 | mCG1867 | hCG41365 |
| 06-142 | mCG18746 | hCG1780827 |
| 06-143 | mCG18928 | hCG41574 |
| 06-144 | mCG19018 | hCG27894 |
| 06-145 | mCG19046 | hCG40314 |
| 06-146 | mCG19072 | hCG15138 |
| 06-147 | mCG19106 | hCG16291 |
| 06-148 | mCG19156 | hCG27607 |
| 06-149 | mCG19208 | hCG20766 |
| 06-150 | mCG19209 | hCG22243 |
| 06-151 | mCG19250 | hCG27772 |
| 06-152 | mCG19287 | hCG1748307 |
| 06-153 | mCG19337 | hCG28784 |
| 06-154 | mCG19401 | hCG38450 |
| 06-155 | mCG1941 | hCG40854 |
| 06-156 | mCG1961 | hCG40844 |
| 06-157 | mCG19789 | hCG24313 |
| 06-158 | mCG1982 | hCG24071 |
| 06-159 | mCG19885 | hCG26017 |
| 06-160 | mCG19929 | hCG40063 |
| 06-161 | mCG19993 | hCG25375 |
| 06-162 | mCG20206 | hCG27935 |
| 06-163 | mCG20340 | hCG18066 |
| 06-164 | mCG20392 | hCG41562 |
| 06-165 | mCG20408 | hCG15769 |
| 06-166 | mCG20501 | hCG16575 |
| 06-167 | mCG20543 | hCG17361 |
| 06-168 | mCG20544 | hCG22647 |
| 06-169 | mCG20549 | hCG17357 |
| 06-170 | mCG20599 | hCG40952 |
| 06-171 | mCG20647 | hCG37125 |
| 06-172 | mCG20650 | hCG38101 |
| 06-173 | mCG21092 | hCG16326 |
| 06-174 | mCG21183 | hCG32701 |

-continued

| | | |
|---|---|---|
| 06-175 | mCG21200 | hCG17049 |
| 06-176 | mCG21319 | hCG39866 |
| 06-177 | mCG2140 | hCG1723924 |
| 06-178 | mCG21411 | hCG15095 |
| 06-179 | mCG21419 | hCG15331 |
| 06-180 | mCG21446 | hCG14759 |
| 06-181 | mCG21498 | hCG38237 |
| 06-182 | mCG21659 | hCG18576 |
| 06-183 | mCG21733 | hCG40245 |
| 06-184 | mCG21872 | hCG17143 |
| 06-185 | mCG21902 | hCG30014 |
| 06-186 | mCG22056 | hCG40203 |
| 06-187 | mCG22132 | hCG15373 |
| 06-188 | mCG2215 | hCG401221 |
| 06-189 | mCG22161 | hCG1781402 |
| 06-190 | mCG22171 | hCG37949 |
| 06-191 | mCG22175 | hCG1735628 |
| 06-192 | mCG22205 | hCG16145 |
| 06-193 | mCG22245 | hCG15467 |
| 06-194 | mCG22259 | hCG27692 |
| 06-195 | mCG22352 | hCG19724 |
| 06-196 | mCG22397 | hCG21624 |
| 06-197 | mCG22413 | hCG21734 |
| 06-198 | mCG22464 | hCG17117 |
| 06-199 | mCG22467 | hCG17195 |
| 06-200 | mCG22474 | hCG17936 |
| 06-201 | mCG22518 | hCG38672 |
| 06-202 | mCG22537 | hCG1747156 |
| 06-203 | mCG2260 | hCG23472 |
| 06-204 | mCG22656 | hCG20930 |
| 06-205 | mCG22686 | hCG37091 |
| 06-206 | mCG22753 | hCG20786 |
| 06-207 | mCG23380 | hCG27276 |
| 06-208 | mCG23443 | hCG1737521 |
| 06-209 | mCG23445 | hCG16206 |
| 06-210 | mCG2395 | hCG33029 |
| 06-211 | mCG2435 | hCG16501 |
| 06-212 | mCG2468 | hCG16728 |
| 06-213 | mCG2479 | hCG1780031 |
| 06-214 | mCG2484 | hCG1788599 |
| 06-215 | mCG2509 | hCG17286 |
| 06-216 | mCG2574 | hCG1784894 |
| 06-217 | mCG2609 | hCG14997 |
| 06-218 | mCG2622 | hCG1747365 |
| 06-219 | mCG2706 | hCG28763 |
| 06-220 | mCG2708 | hCG28766 |
| 06-221 | mCG2727 | hCG17889 |
| 06-222 | mCG2740 | hCG27644 |
| 06-223 | mCG2943 | hCG40040 |
| 06-224 | mCG3043 | hCG1738334 |
| 06-225 | mCG3264 | hCG29513 |
| 06-226 | mCG3413 | hCG29916 |
| 06-227 | mCG3601 | hCG37990 |
| 06-228 | mCG3698 | hCG20145 |
| 06-229 | mCG3757 | hCG21349 |
| 06-230 | mCG3767 | hCG32368 |
| 06-231 | mCG3774 | hCG21354 |
| 06-232 | mCG3775 | hCG21354 |
| 06-233 | mCG3793 | hCG27352 |
| 06-234 | mCG3824 | hCG27823 |
| 06-235 | mCG3889 | hCG27192 |
| 06-236 | mCG3931 | hCG23145 |
| 06-237 | mCG4010 | hCG1739389 |
| 06-238 | mCG4192 | hCG41911 |
| 06-239 | mCG4251 | hCG1640192 |
| 06-240 | mCG4296 | hCG40093 |
| 06-241 | mCG4317 | hCG28302 |
| 06-242 | mCG4378 | hCG40788 |
| 06-243 | mCG4428 | hCG30155 |
| 06-244 | mCG4463 | hCG21099 |
| 06-245 | mCG4468 | hCG19805 |
| 06-246 | mCG4490 | hCG39740 |
| 06-247 | mCG4492 | hCG39730 |
| 06-248 | mCG4493 | hCG1766501 |
| 06-249 | mCG4638 | hCG27795 |
| 06-250 | mCG4768 | hCG22679 |
| 06-251 | mCG4799 | hCG33122 |
| 06-252 | mCG4860 | hCG22132 |
| 06-253 | mCG4940 | hCG1785738 |
| 06-254 | mCG49939 | hCG22769 |
| 06-255 | mCG5034 | hCG23376 |
| 06-256 | mCG5067 | hCG19082 |
| 06-257 | mCG51010 | hCG21464 |
| 06-258 | mCG51020 | hCG1643989 |
| 06-259 | mCG5113 | hCG1782397 |
| 06-260 | mCG51582 | hCG39434 |
| 06-261 | mCG51664 | hCG28994 |
| 06-262 | mCG5362 | hCG16933 |
| 06-263 | mCG54271 | hCG18129 |
| 06-264 | mCG5429 | hCG38378 |
| 06-265 | mCG5448 | hCG38103 |
| 06-266 | mCG5518 | hCG22355 |
| 06-267 | mCG5530 | hCG22353 |
| 06-268 | mCG5531 | hCG20493 |
| 06-269 | mCG5548 | hCG1779020 |
| 06-270 | mCG5662 | hCG14831 |
| 06-271 | mCG57125 | hCG1742422 |
| 06-272 | mCG5728 | hCG1811271 |
| 06-273 | mCG5738 | hCG37394 |
| 06-274 | mCG5779 | hCG21040 |
| 06-275 | mCG5868 | hCG28297 |
| 06-276 | mCG6000 | hCG1777660 |
| 06-277 | mCG6027 | hCG38622 |
| 06-278 | mCG6056 | hCG37193 |
| 06-279 | mCG6178 | hCG33356 |
| 06-280 | mCG6322 | hCG32986 |
| 06-281 | mCG6388 | hCG38644 |
| 06-282 | mCG6403 | hCG38453 |
| 06-283 | mCG6481 | hGG40757 |
| 06-284 | mCG6500 | hCG14773 |
| 06-285 | mCG6549 | hCG37127 |
| 06-286 | mCG6627 | hCG27461 |
| 06-287 | mCG6631 | hCG29839 |
| 06-288 | mCG66316 | hCG29191 |
| 06-289 | mCG6636 | hCG33210 |
| 06-290 | mCG6875 | hCG32956 |
| 06-291 | mCG6919 | hCG1644194 |
| 06-292 | mCG6945 | hCG14907 |
| 06-293 | mCG6974 | hCG17395 |
| 06-294 | mCG6981 | hCG1735348 |
| 06-295 | mCG7008 | hCG25055 |
| 06-296 | mCG7143 | hCG32521 |
| 06-297 | mCG7189 | hCG1640838 |
| 06-298 | mCG7211 | hCG1781938 |
| 06-299 | mCG7212 | hCG37223 |
| 06-300 | mCG7256 | hCG39345 |
| 06-301 | mCG7264 | hCG39344 |
| 06-302 | mCG7348 | hCG28560 |
| 06-303 | mCG7369 | hCG22856 |
| 06-304 | mCG7522 | hCG32930 |
| 06-305 | mCG7669 | hCG30694 |
| 06-306 | mCG7689 | hCG32392 |
| 06-307 | mCG7785 | hCG24868 |
| 06-308 | mCG7804 | hCG39065 |
| 06-309 | mCG7826 | hCG1735557 |
| 06-310 | mCG7831 | hCG37578 |
| 06-311 | mCG7923 | hGG22125 |
| 06-312 | mCG7927 | hCG20927 |
| 06-313 | mCG7964 | hCG27325 |
| 06-314 | mCG8211 | hCG24168 |
| 06-315 | mCG8306 | hCG18967 |
| 06-316 | mCG8426 | hCG27711 |
| 06-317 | mCG8466 | hCG29605 |
| 06-318 | mCG8527 | hCG34336 |
| 06-319 | mCG8564 | hCG27679 |
| 06-320 | mCG8581 | hCG14605 |
| 06-321 | mCG8584 | hCG15017 |
| 06-322 | mCG8821 | hCG31443 |
| 06-323 | mCG8835 | hCG17175 |
| 06-324 | mCG8893 | hCG19941 |
| 06-325 | mCG8963 | hCG1639824 |
| 06-326 | mCG8993 | hCG34092 |
| 06-327 | mCG9022 | hCG32769 |
| 06-328 | mCG9049 | hCG25130 |
| 06-329 | mCG9061 | hCG37877 |
| 06-330 | mCG9066 | hCG37872 |
| 06-331 | mCG9077 | hCG23504 |
| 06-332 | mCG9223 | hCG15927 |

-continued

| | | |
|---|---|---|
| 06-333 | mCG9253 | hCG22665 |
| 06-334 | mCG9266 | hCG14925 |
| 06-335 | mCG9336 | hCG28203 |
| 06-336 | mCG9393 | hCG16330 |
| 06-337 | mCG9397 | hCG24200 |
| 06-338 | mCG9437 | hCG16805 |
| 06-339 | mCG9440 | hCG401128 |
| 06-340 | mCG9536 | hCG23831 |
| 06-341 | mCG9597 | hCG37835 |
| 06-342 | mCG9808 | hCG30268 |
| 06-343 | mCG9960 | hCG1642754 |

TABLE 2

IDENTIFICATION OF SEQUENCES

| SEQ ID NOS. | SEQUENCES |
|---|---|
| | CANCER GENE: mCG10049/hCG41676 |
| 1. | MOUSE GENOMIC SEQUENCE (mCG10049) |
| 2. | MOUSE mRNA SEQUENCE (mCT10558) |
| 3. | MOUSE PROTEIN SEQUENCE (mCP3178) |
| 4. | HUMAN GENOMIC SEQUENCE (hCG41676) |
| 5. | HUMAN mRNA SEQUENCE (hCT32948) |
| 6. | HUMAN PROTEIN SEQUENCE (hCP51539) |
| | CANCER GENE: mCG10078/hCG19413 |
| 7. | MOUSE GENOMIC SEQUENCE (mCG10078) |
| 8. | MOUSE mRNA SEQUENCE (mCT9894) |
| 9. | MOUSE PROTEIN SEQUENCE (mCP3703) |
| 10. | HUMAN GENOMIC SEQUENCE (hCG19413) |
| 11. | HUMAN mRNA SEQUENCE (hCT10484) |
| 12. | HUMAN PROTEIN SEQUENCE (hCP37142) |
| | CANCER GENE: mCG10132/hCG21567 |
| 13. | MOUSE GENOMIC SEQUENCE (mCG10132) |
| 14. | MOUSE mRNA SEQUENCE (mCT10267) |
| 15. | MOUSE PROTEIN SEQUENCE (mCP19301) |
| 16. | HUMAN GENOMIC SEQUENCE (hCG21567) |
| 17. | HUMAN mRNA SEQUENCE (hCT12659) |
| 18. | HUMAN PROTEIN SEQUENCE (hCP39072) |
| | CANCER GENE: mCG10208/hCG21073 |
| 19. | MOUSE GENOMIC SEQUENCE (mCG10208) |
| 20. | MOUSE mRNA SEQUENCE (mCT10193) |
| 21. | MOUSE PROTEIN SEQUENCE (mCP19207) |
| 22. | HUMAN GENOMIC SEQUENCE (hCG21073) |
| 23. | HUMAN mRNA SEQUENCE (hCT12159) |
| 24. | HUMAN PROTEIN SEQUENCE (hCP38653) |
| | CANCER GENE: mCG10215/hCG37475 |
| 25. | MOUSE GENOMIC SEQUENCE (mCG10215) |
| 26. | MOUSE mRNA SEQUENCE (mCT10069) |
| 27. | MOUSE PROTEIN SEQUENCE (mCP4103) |
| 28. | HUMAN GENOMIC SEQUENCE (hCG37475) |
| 29. | HUMAN mRNA SEQUENCE (hCT28708) |
| 30. | HUMAN PROTEIN SEQUENCE (hCP48631) |
| | CANCER GENE: mCG10283/hCG201153 |
| 31. | MOUSE GENOMIC SEQUENCE (mCG10283) |
| 32. | MOUSE mRNA SEQUENCE (mCT10883) |
| 33. | MOUSE PROTEIN SEQUENCE (mCP15399) |
| 34. | HUMAN GENOMIC SEQUENCE (hCG201153) |
| 35. | HUMAN mRNA SEQUENCE (hCT201155) |
| 36. | HUMAN PROTEIN SEQUENCE (hCP201495) |
| | CANCER GENE: mCG10301/hCG25637 |
| 37. | MOUSE GENOMIC SEQUENCE (mCG10301) |
| 38. | MOUSE mRNA SEQUENCE (mCT10901) |
| 39. | MOUSE PROTEIN SEQUENCE (mCP15440) |
| 40. | HUMAN GENOMIC SEQUENCE (hCG25637) |
| 41. | HUMAN mRNA SEQUENCE (hCT6762) |
| 42. | HUMAN PROTEIN SEQUENCE (hCP42334) |

TABLE 2-continued

IDENTIFICATION OF SEQUENCES

| SEQ ID NOS. | SEQUENCES |
|---|---|
| | CANCER GENE: mCG10339/hCG36720 |
| 43. | MOUSE GENOMIC SEQUENCE (mCG10339) |
| 44. | MOUSE mRNA SEQUENCE (mCT10526) |
| 45. | MOUSE PROTEIN SEQUENCE (mCP5145) |
| 46. | HUMAN GENOMIC SEQUENCE (hCG36720) |
| 47. | HUMAN mRNA SEQUENCE (hCT23561) |
| 48. | HUMAN PROTEIN SEQUENCE (hCP47035) |
| | CANCER GENE: mCG10368/hCG1777139 |
| 49. | MOUSE GENOMIC SEQUENCE (mCG10368) |
| 50. | MOUSE mRNA SEQUENCE (mCT10980) |
| 51. | MOUSE PROTEIN SEQUENCE (mCP 11203) |
| 52. | HUMAN GENOMIC SEQUENCE (hCG1777139) |
| 53. | HUMAN mRNA SEQUENCE (hCT1815886) |
| 54. | HUMAN PROTEIN SEQUENCE (hCP1719532) |
| | CANCER GENE: mCG10474/hCG1784975 |
| 55. | MOUSE GENOMIC SEQUENCE (mCG10474) |
| 56. | MOUSE mRNA SEQUENCE (mCT11063) |
| 57. | MOUSE PROTEIN SEQUENCE (mCP18249) |
| 58. | HUMAN GENOMIC SEQUENCE (hCG1784975) |
| 59. | HUMAN mRNA SEQUENCE (hCT1823965) |
| 60. | HUMAN PROTEIN SEQUENCE (hCP1743817) |
| | CANCER GENE: mCG10543/hCG1776024 |
| 61. | MOUSE GENOMIC SEQUENCE (mCG10543) |
| 62. | MOUSE mRNA SEQUENCE (mCT10637) |
| 63. | MOUSE PROTEIN SEQUENCE (mCP5099) |
| 64. | HUMAN GENOMIC SEQUENCE (hCG1776024) |
| 65. | HUMAN mRNA SEQUENCE (hCT1814713) |
| 66. | HUMAN PROTEIN SEQUENCE (hCP1734062) |
| | CANCER GENE: mCG10583/hCG1780788 |
| 67. | MOUSE GENOMIC SEQUENCE (mCG10583) |
| 68. | MOUSE mRNA SEQUENCE (mCT10746) |
| 69. | MOUSE PROTEIN SEQUENCE (mCP14741) |
| 70. | HUMAN GENOMIC SEQUENCE (hCG1780788) |
| 71. | HUMAN mRNA SEQUENCE (hCT1819630) |
| 72. | HUMAN PROTEIN SEQUENCE (hCP1700014) |
| | CANCER GENE: mCG1062/hCG28127 |
| 73. | MOUSE GENOMIC SEQUENCE (mCG1062) |
| 74. | MOUSE mRNA SEQUENCE (mCT8657) |
| 75. | MOUSE PROTEIN SEQUENCE (mCP7520) |
| 76. | HUMAN GENOMIC SEQUENCE (hCG28127) |
| 77. | HUMAN mRNA SEQUENCE (hCT19273) |
| 78. | HUMAN PROTEIN SEQUENCE (hCP44846) |
| | CANCER GENE: mCG10645/hCG15849 |
| 79. | MOUSE GENOMIC SEQUENCE (mCG10645) |
| 80. | MOUSE mRNA SEQUENCE (mCT10788) |
| 81. | MOUSE PROTEIN SEQUENCE (mCP17009) |
| 82. | HUMAN GENOMIC SEQUENCE (hCG15849) |
| 83. | HUMAN mRNA SEQUENCE (hCT1951536) |
| 84. | HUMAN PROTEIN SEQUENCE (hCP1752924) |
| | CANCER GENE: mCG10734/hCG15249 |
| 85. | MOUSE GENOMIC SEQUENCE (mCG10734) |
| 86. | MOUSE mRNA SEQUENCE (mCT11434) |
| 87. | MOUSE PROTEIN SEQUENCE (mCP17429) |
| 88. | HUMAN GENOMIC SEQUENCE (hCG15249) |
| 89. | HUMAN mRNA SEQUENCE (hCT6270) |
| 90. | HUMAN PROTEIN SEQUENCE (hCP34885) |
| | CANCER GENE: mCG10776/hCG28722 |
| 91. | MOUSE GENOMIC SEQUENCE (mCG10776) |
| 92. | MOUSE mRNA SEQUENCE (mCT11377) |
| 93. | MOUSE PROTEIN SEQUENCE (mCP13457) |
| 94. | HUMAN GENOMIC SEQUENCE (hCG28722) |
| 95. | HUMAN mRNA SEQUENCE (hCT19877) |
| 96. | HUMAN PROTEIN SEQUENCE (hCP44105) |

TABLE 2-continued

IDENTIFICATION OF SEQUENCES

| SEQ ID NOS. | SEQUENCES |
|---|---|
| | CANCER GENE: mCG11034/hCG26773 |
| 97. | MOUSE GENOMIC SEQUENCE (mCG11034) |
| 98. | MOUSE mRNA SEQUENCE (mCT11271) |
| 99. | MOUSE PROTEIN SEQUENCE (mCP11422) |
| 100. | HUMAN GENOMIC SEQUENCE (hCG26773) |
| 101. | HUMAN mRNA SEQUENCE (hCT17905) |
| 102. | HUMAN PROTEIN SEQUENCE (hCP43570) |
| | CANCER GENE: mCG11078/hCG1644496 |
| 103. | MOUSE GENOMIC SEQUENCE (mCG11078) |
| 104. | MOUSE PROTEIN SEQUENCE (mCP14937) |
| 105. | MOUSE mRNA SEQUENCE (mCT11355) |
| 106. | HUMAN GENOMIC SEQUENCE (hCG1644496) |
| 107. | HUMAN mRNA SEQUENCE (hCT1644623) |
| 108. | HUMAN PROTEIN SEQUENCE (hCP1612572) |
| | CANCER GENE: mCG11119/hCG27363 |
| 109. | MOUSE GENOMIC SEQUENCE (mCG11119) |
| 110. | MOUSE mRNA SEQUENCE (mCT11558) |
| 111. | MOUSE PROTEIN SEQUENCE (mCP5417) |
| 112. | HUMAN GENOMIC SEQUENCE (hCG27363) |
| 113. | HUMAN mRNA SEQUENCE (hCT18502) |
| 114. | HUMAN PROTEIN SEQUENCE (hCP42949) |
| | CANCER GENE: mCG11136/hCG1782215 |
| 115. | MOUSE GENOMIC SEQUENCE (mCG11136) |
| 116. | MOUSE mRNA SEQUENCE (mCT11575) |
| 117. | MOUSE PROTEIN SEQUENCE (mCP5488) |
| 118. | HUMAN GENOMIC SEQUENCE (hCG1782215) |
| 119. | HUMAN mRNA SEQUENCE (hCT1821116) |
| 120. | HUMAN PROTEIN SEQUENCE (hCP1734687) |
| | CANCER GENE: mCG11291/hCG1787835 |
| 121. | MOUSE GENOMIC SEQUENCE (mCG11291) |
| 122. | MOUSE mRNA SEQUENCE (mCT11578) |
| 123. | MOUSE PROTEIN SEQUENCE (mCP1456) |
| 124. | HUMAN GENOMIC SEQUENCE (hCG1787835) |
| 125. | HUMAN mRNA SEQUENCE (hCT1826903) |
| 126. | HUMAN PROTEIN SEQUENCE (hCP1729572) |
| | CANCER GENE: mCG11441/hCG401177 |
| 127. | MOUSE GENOMIC SEQUENCE (mCG11441) |
| 128. | MOUSE mRNA SEQUENCE (mCT12183) |
| 129. | MOUSE PROTEIN SEQUENCE (mCP4248) |
| 130. | HUMAN GENOMIC SEQUENCE (hCG401177) |
| 131. | HUMAN mRNA SEQUENCE (hCT401179) |
| 132. | HUMAN PROTEIN SEQUENCE (hCP801112) |
| | CANCER GENE: mCG11471/hCG40117 |
| 133. | MOUSE GENOMIC SEQUENCE (mCG11471) |
| 134. | MOUSE mRNA SEQUENCE (mCT11937) |
| 135. | MOUSE PROTEIN SEQUENCE (mCP14289) |
| 136. | HUMAN GENOMIC SEQUENCE (hCG40117) |
| 137. | HUMAN mRNA SEQUENCE (hCT1825100) |
| 138. | HUMAN PROTEIN SEQUENCE (hCP1735822) |
| | CANCER GENE: mCG11506/hCG28011 |
| 139. | MOUSE GENOMIC SEQUENCE (mCG11506) |
| 140. | MOUSE mRNA SEQUENCE (mCT11734) |
| 141. | MOUSE PROTEIN SEQUENCE (mCP13976) |
| 142. | HUMAN GENOMIC SEQUENCE (hCG28011) |
| 143. | HUMAN mRNA SEQUENCE (hCT19157) |
| 144. | HUMAN PROTEIN SEQUENCE (hCP43537) |
| | CANCER GENE: mCG11566/hCG21793 |
| 145. | MOUSE GENOMIC SEQUENCE (mCG11566) |
| 146. | MOUSE mRNA SEQUENCE (mCT12445) |
| 147. | MOUSE PROTEIN SEQUENCE (mCP5151) |
| 148. | HUMAN GENOMIC SEQUENCE (hCG21793) |
| 149. | HUMAN mRNA SEQUENCE (hCT12886) |
| 150. | HUMAN PROTEIN SEQUENCE (hCP39644) |
| | CANCER GENE: mCG11814/hCG1775160 |
| 151. | MOUSE GENOMIC SEQUENCE (mCG11814) |
| 152. | MOUSE mRNA SEQUENCE (mCT12311) |
| 153. | MOUSE PROTEIN SEQUENCE (mCP2528) |
| 154. | HUMAN GENOMIC SEQUENCE (hCG1775160) |
| 155. | HUMAN mRNA SEQUENCE (hCT1813820) |
| 156. | HUMAN PROTEIN SEQUENCE (hCP1704942) |
| | CANCER GENE: mCG11829/hCG37570 |
| 157. | MOUSE GENOMIC SEQUENCE (mCG11829) |
| 158. | MOUSE mRNA SEQUENCE (mCT12233) |
| 159. | MOUSE PROTEIN SEQUENCE (mCP17336) |
| 160. | HUMAN GENOMIC SEQUENCE (hCG37570) |
| 161. | HUMAN mRNA SEQUENCE (hCT28803) |
| 162. | HUMAN PROTEIN SEQUENCE (hCP48746) |
| | CANCER GENE: mCG11914/hCG1640505 |
| 163. | MOUSE GENOMIC SEQUENCE (mCG11914) |
| 164. | MOUSE mRNA SEQUENCE (mCT12622) |
| 165. | MOUSE PROTEIN SEQUENCE (mCP17406) |
| 166. | HUMAN GENOMIC SEQUENCE (hCG1640505) |
| 167. | HUMAN mRNA SEQUENCE (hCT1640632) |
| 168. | HUMAN PROTEIN SEQUENCE (hCP1619848) |
| | CANCER GENE: mCG11924/hCG16317 |
| 169. | MOUSE GENOMIC SEQUENCE (mCG11924) |
| 170. | MOUSE mRNA SEQUENCE (mCT14543) |
| 171. | MOUSE PROTEIN SEQUENCE (mCP16061) |
| 172. | HUMAN GENOMIC SEQUENCE (hCG16317) |
| 173. | HUMAN mRNA SEQUENCE (hCT7353) |
| 174. | HUMAN PROTEIN SEQUENCE (hCP33574) |
| | CANCER GENE: mCG11959/hCG24311 |
| 175. | MOUSE GENOMIC SEQUENCE (mCG11959) |
| 176. | MOUSE mRNA SEQUENCE (mCT14675) |
| 177. | MOUSE PROTEIN SEQUENCE (mCP1817) |
| 178. | HUMAN GENOMIC SEQUENCE (hCG24311) |
| 179. | HUMAN mRNA SEQUENCE (hCT15425) |
| 180. | HUMAN PROTEIN SEQUENCE (hCP41558) |
| | CANCER GENE: mCG1196/hCG26669 |
| 181. | MOUSE GENOMIC SEQUENCE (mCG1196) |
| 182. | MOUSE mRNA SEQUENCE (mCT8240) |
| 183. | MOUSE PROTEIN SEQUENCE (mCP10249) |
| 184. | HUMAN GENOMIC SEQUENCE (hCG26669) |
| 185. | HUMAN mRNA SEQUENCE (hCT17801) |
| 186. | HUMAN PROTEIN SEQUENCE (hCP46069) |
| | CANCER GENE: mCG12024/hCG39093 |
| 187. | MOUSE GENOMIC SEQUENCE (mCG12024) |
| 188. | MOUSE mRNA SEQUENCE (mCT12525) |
| 189. | MOUSE PROTEIN SEQUENCE (mCP7959) |
| 190. | HUMAN GENOMIC SEQUENCE (hCG39093) |
| 191. | HUMAN mRNA SEQUENCE (hCT30340) |
| 192. | HUMAN PROTEIN SEQUENCE (hCP50417) |
| | CANCER GENE: mCG12068/hCG1787637 |
| 193. | MOUSE GENOMIC SEQUENCE (mCG12068) |
| 194. | MOUSE mRNA SEQUENCE (mCT12684) |
| 195. | MOUSE PROTEIN SEQUENCE (mCP6907) |
| 196. | HUMAN GENOMIC SEQUENCE (hCG1787637) |
| 197. | HUMAN mRNA SEQUENCE (hCT1826701) |
| 198. | HUMAN PROTEIN SEQUENCE (hCP1705462) |
| | CANCER GENE: mCG12133/hCG23625 |
| 199. | MOUSE GENOMIC SEQUENCE (mCG12133) |
| 200. | MOUSE mRNA SEQUENCE (mCT16612) |
| 201. | MOUSE PROTEIN SEQUENCE (mCP7634) |
| 202. | HUMAN GENOMIC SEQUENCE (hCG23625) |
| 203. | HUMAN mRNA SEQUENCE (hCT14732) |
| 204. | HUMAN PROTEIN SEQUENCE (hCP40974) |

TABLE 2-continued

IDENTIFICATION OF SEQUENCES

| SEQ ID NOS. | SEQUENCES |
|---|---|
| | CANCER GENE: mCG12182/hCG40211 |
| 205. | MOUSE GENOMIC SEQUENCE (mCG12182) |
| 206. | MOUSE mRNA SEQUENCE (mCT16772) |
| 207. | MOUSE PROTEIN SEQUENCE (mCP5424) |
| 208. | HUMAN GENOMIC SEQUENCE (hCG40211) |
| 209. | HUMAN mRNA SEQUENCE (hCT31465) |
| 210. | HUMAN PROTEIN SEQUENCE (hCP49961) |
| | CANCER GENE: mCG12368/hCG1744883 |
| 211. | MOUSE GENOMIC SEQUENCE (mCG12368) |
| 212. | MOUSE mRNA SEQUENCE (mCT16089) |
| 213. | MOUSE PROTEIN SEQUENCE (mCP18849) |
| 214. | HUMAN GENOMIC SEQUENCE (hCG1744883) |
| 215. | HUMAN mRNA SEQUENCE (hCT1783124) |
| 216. | HUMAN PROTEIN SEQUENCE (hCP1717267) |
| | CANCER GENE: mCG12523/hCG23847 |
| 217. | MOUSE GENOMIC SEQUENCE (mCG12523) |
| 218. | MOUSE mRNA SEQUENCE (mCT13425) |
| 219. | MOUSE PROTEIN SEQUENCE (mCP10914) |
| 220. | HUMAN GENOMIC SEQUENCE (hCG23847) |
| 221. | HUMAN mRNA SEQUENCE (hCT14959) |
| 222. | HUMAN PROTEIN SEQUENCE (hCP41235) |
| | CANCER GENE: mCG12572/hCG1778483 |
| 223. | MOUSE GENOMIC SEQUENCE (mCG12572) |
| 224. | MOUSE mRNA SEQUENCE (mCT13299) |
| 225. | MOUSE PROTEIN SEQUENCE (mCP8821) |
| 226. | HUMAN GENOMIC SEQUENCE (hCG1778483) |
| 227. | HUMAN mRNA SEQUENCE (hCT1817254) |
| 228. | HUMAN PROTEIN SEQUENCE (hCP1742619) |
| | CANCER GENE: mCG12663/hCG37533 |
| 229. | MOUSE GENOMIC SEQUENCE (mCG12663) |
| 230. | MOUSE mRNA SEQUENCE (mCT13571) |
| 231. | MOUSE PROTEIN SEQUENCE (mCP23112) |
| 232. | HUMAN GENOMIC SEQUENCE (hCG37533) |
| 233. | HUMAN mRNA SEQUENCE (hCT28766) |
| 234. | HUMAN PROTEIN SEQUENCE (hCP48812) |
| | CANCER GENE: mCG12673/hCG1810774 |
| 235. | MOUSE GENOMIC SEQUENCE (mCG12673) |
| 236. | MOUSE mRNA SEQUENCE (mCT13354) |
| 237. | MOUSE PROTEIN SEQUENCE (mCP14021) |
| 238. | HUMAN GENOMIC SEQUENCE (hCG1810774) |
| 239. | HUMAN mRNA SEQUENCE (hCT1950049) |
| 240. | HUMAN PROTEIN SEQUENCE (hCP1767062) |
| | CANCER GENE: mCG12706/hCG1643869 |
| 241. | MOUSE GENOMIC SEQUENCE (mCG12706) |
| 242. | MOUSE mRNA SEQUENCE (mCT13403) |
| 243. | MOUSE PROTEIN SEQUENCE (mCP5983) |
| 244. | HUMAN GENOMIC SEQUENCE (hCG1643869) |
| 245. | HUMAN mRNA SEQUENCE (hCT1643996) |
| 246. | HUMAN PROTEIN SEQUENCE (hCP1635124) |
| | CANCER GENE: mCG12722/hCG33130 |
| 247. | MOUSE GENOMIC SEQUENCE (mCG12722) |
| 248. | MOUSE mRNA SEQUENCE (mCT13363) |
| 249. | MOUSE PROTEIN SEQUENCE (mCP18789) |
| 250. | HUMAN GENOMIC SEQUENCE (hCG33130) |
| 251. | HUMAN mRNA SEQUENCE (hCT24323) |
| 252. | HUMAN PROTEIN SEQUENCE (hCP46493) |
| | CANCER GENE: mCG12724/hCG33132 |
| 253. | MOUSE GENOMIC SEQUENCE (mCG12724) |
| 254. | MOUSE mRNA SEQUENCE (mCT13365) |
| 255. | MOUSE PROTEIN SEQUENCE (mCP18786) |
| 256. | HUMAN GENOMIC SEQUENCE (hCG33132) |
| 257. | HUMAN mRNA SEQUENCE (hCT24325) |
| 258. | HUMAN PROTEIN SEQUENCE (hCP46495) |
| | CANCER GENE: mCG12746/hCG30819 |
| 259. | MOUSE GENOMIC SEQUENCE (mCG12746) |
| 260. | MOUSE mRNA SEQUENCE (mCT13463) |
| 261. | MOUSE PROTEIN SEQUENCE (mCP18800) |
| 262. | HUMAN GENOMIC SEQUENCE (hCG30819) |
| 263. | HUMAN mRNA SEQUENCE (hCT21993) |
| 264. | HUMAN PROTEIN SEQUENCE (hCP44970) |
| | CANCER GENE: mCG12792/hCG24510 |
| 265. | MOUSE GENOMIC SEQUENCE (mCG12792) |
| 266. | MOUSE mRNA SEQUENCE (mCT13497) |
| 267. | MOUSE PROTEIN SEQUENCE (mCP8770) |
| 268. | HUMAN GENOMIC SEQUENCE (hCG24510) |
| 269. | HUMAN mRNA SEQUENCE (hCT15627) |
| 270. | HUMAN PROTEIN SEQUENCE (hCP41693) |
| | CANCER GENE: mCG12872/hCG23021 |
| 271. | MOUSE GENOMIC SEQUENCE (mCG12872) |
| 272. | MOUSE mRNA SEQUENCE (mCT13522) |
| 273. | MOUSE PROTEIN SEQUENCE (mCP21017) |
| 274. | HUMAN GENOMIC SEQUENCE (hCG23021) |
| 275. | HUMAN mRNA SEQUENCE (hCT14123) |
| 276. | HUMAN PROTEIN SEQUENCE (hCP40456) |
| | CANCER GENE: mCG12945/hCG1739154 |
| 277. | MOUSE GENOMIC SEQUENCE (mCG12945) |
| 278. | MOUSE mRNA SEQUENCE (mCT13581) |
| 279. | MOUSE PROTEIN SEQUENCE (mCP16226) |
| 280. | HUMAN GENOMIC SEQUENCE (hCG1739154) |
| 281. | HUMAN mRNA SEQUENCE (hCT1777235) |
| 282. | HUMAN PROTEIN SEQUENCE (hCP1732635) |
| | CANCER GENE: mCG13023/hCG20125 |
| 283. | MOUSE GENOMIC SEQUENCE (mCG13023) |
| 284. | MOUSE mRNA SEQUENCE (mCT13768) |
| 285. | MOUSE PROTEIN SEQUENCE (mCP22537) |
| 286. | HUMAN GENOMIC SEQUENCE (hCG20125) |
| 287. | HUMAN mRNA SEQUENCE (hCT11196) |
| 288. | HUMAN PROTEIN SEQUENCE (hCP37863) |
| | CANCER GENE: mCG13044/hCG32359 |
| 289. | MOUSE GENOMIC SEQUENCE (mCG13044) |
| 290. | MOUSE mRNA SEQUENCE (mCT11876) |
| 291. | MOUSE PROTEIN SEQUENCE (mCP2702) |
| 292. | HUMAN GENOMIC SEQUENCE (hCG32359) |
| 293. | HUMAN mRNA SEQUENCE (hCT1950129) |
| 294. | HUMAN PROTEIN SEQUENCE (hCP1751147) |
| | CANCER GENE: mCG13084/hCG1735292 |
| 295. | MOUSE GENOMIC SEQUENCE (mCG13084) |
| 296. | MOUSE mRNA SEQUENCE (mCT12008) |
| 297. | MOUSE PROTEIN SEQUENCE (mCP11724) |
| 298. | HUMAN GENOMIC SEQUENCE (hCG1735292) |
| 299. | HUMAN mRNA SEQUENCE (hCT1773283) |
| 300. | HUMAN PROTEIN SEQUENCE (hCP1745220) |
| | CANCER GENE: mCG13312/hCG14731 |
| 301. | MOUSE GENOMIC SEQUENCE (mCG13312) |
| 302. | MOUSE mRNA SEQUENCE (mCT11850) |
| 303. | MOUSE PROTEIN SEQUENCE (mCP17747) |
| 304. | HUMAN GENOMIC SEQUENCE (hCG14731) |
| 305. | HUMAN mRNA SEQUENCE (hCT5752) |
| 306. | HUMAN PROTEIN SEQUENCE (hCP33220) |
| | CANCER GENE: mCG1338/hCG32977 |
| 307. | MOUSE GENOMIC SEQUENCE (mCG1338) |
| 308. | MOUSE mRNA SEQUENCE (mCT8784) |
| 309. | MOUSE PROTEIN SEQUENCE (mCP13373) |
| 310. | HUMAN GENOMIC SEQUENCE (hCG32977) |
| 311. | HUMAN mRNA SEQUENCE (hCT24169) |
| 312. | HUMAN PROTEIN SEQUENCE (hCP46322) |

TABLE 2-continued

IDENTIFICATION OF SEQUENCES

| SEQ ID NOS. | SEQUENCES |
|---|---|
| | CANCER GENE: mCG13395/hCG22712 |
| 313. | MOUSE GENOMIC SEQUENCE (mCG13395) |
| 314. | MOUSE mRNA SEQUENCE (mCT11881) |
| 315. | MOUSE PROTEIN SEQUENCE (mCP7649) |
| 316. | HUMAN GENOMIC SEQUENCE (hCG22712) |
| 317. | HUMAN mRNA SEQUENCE (hCT13810) |
| 318. | HUMAN PROTEIN SEQUENCE (hCP40157) |
| | CANCER GENE: mCG13466/hCG38705 |
| 319. | MOUSE GENOMIC SEQUENCE (mCG13466) |
| 320. | MOUSE mRNA SEQUENCE (mCT11497) |
| 321. | MOUSE PROTEIN SEQUENCE (mCP16741) |
| 322. | HUMAN GENOMIC SEQUENCE (hCG38705) |
| 323. | HUMAN mRNA SEQUENCE (hCT29949) |
| 324. | HUMAN PROTEIN SEQUENCE (hCP48563) |
| | CANCER GENE: mCG13520/hCG15674 |
| 325. | MOUSE GENOMIC SEQUENCE (mCG13520) |
| 326. | MOUSE mRNA SEQUENCE (mCT14620) |
| 327. | MOUSE PROTEIN SEQUENCE (mCP3864) |
| 328. | HUMAN GENOMIC SEQUENCE (hCG15674) |
| 329. | HUMAN mRNA SEQUENCE (hCT6699) |
| 330. | HUMAN PROTEIN SEQUENCE (hCP34668) |
| | CANCER GENE: mCG13636/hCG36954 |
| 331. | MOUSE GENOMIC SEQUENCE (mCG13636) |
| 332. | MOUSE mRNA SEQUENCE (mCT16287) |
| 333. | MOUSE PROTEIN SEQUENCE (mCP12701) |
| 334. | HUMAN GENOMIC SEQUENCE (hCG36954) |
| 335. | HUMAN mRNA SEQUENCE (hCT1827782) |
| 336. | HUMAN PROTEIN SEQUENCE (hCP1698519) |
| | CANCER GENE: mCG13896/hCG40471 |
| 337. | MOUSE GENOMIC SEQUENCE (mCG13896) |
| 338. | MOUSE mRNA SEQUENCE (mCT18237) |
| 339. | MOUSE PROTEIN SEQUENCE (mCP18847) |
| 340. | HUMAN GENOMIC SEQUENCE (hCG40471) |
| 341. | HUMAN mRNA SEQUENCE (hCT1958638) |
| 342. | HUMAN PROTEIN SEQUENCE (hCP1766706) |
| | CANCER GENE: mCG14020/hCG1732038 |
| 343. | MOUSE GENOMIC SEQUENCE (mCG14020) |
| 344. | MOUSE mRNA SEQUENCE (mCT19128) |
| 345. | MOUSE PROTEIN SEQUENCE (mCP10814) |
| 346. | HUMAN GENOMIC SEQUENCE (hCG1732038) |
| 347. | HUMAN mRNA SEQUENCE (hCT1769897) |
| 348. | HUMAN PROTEIN SEQUENCE (hCP1741666) |
| | CANCER GENE: mCG14116/hCG39199 |
| 349. | MOUSE GENOMIC SEQUENCE (mCG14116) |
| 350. | MOUSE mRNA SEQUENCE (mCT19570) |
| 351. | MOUSE PROTEIN SEQUENCE (mCP16557) |
| 352. | HUMAN GENOMIC SEQUENCE (hCG39199) |
| 353. | HUMAN mRNA SEQUENCE (hCT30448) |
| 354. | HUMAN PROTEIN SEQUENCE (hCP49026) |
| | CANCER GENE: mCG14172/hCG15529 |
| 355. | MOUSE GENOMIC SEQUENCE (mCG14172) |
| 356. | MOUSE mRNA SEQUENCE (mCT12571) |
| 357. | MOUSE PROTEIN SEQUENCE (mCP16881) |
| 358. | HUMAN GENOMIC SEQUENCE (hCG15529) |
| 359. | HUMAN mRNA SEQUENCE (hCT6554) |
| 360. | HUMAN PROTEIN SEQUENCE (hCP33393) |
| | CANCER GENE: mCG1422/hCG24418 |
| 361. | MOUSE GENOMIC SEQUENCE (mCG1422) |
| 362. | MOUSE mRNA SEQUENCE (mCT8441) |
| 363. | MOUSE PROTEIN SEQUENCE (mCP14824) |
| 364. | HUMAN GENOMIC SEQUENCE (hCG24418) |
| 365. | HUMAN mRNA SEQUENCE (hCT15535) |
| 366. | HUMAN PROTEIN SEQUENCE (hCP41649) |

TABLE 2-continued

IDENTIFICATION OF SEQUENCES

| SEQ ID NOS. | SEQUENCES |
|---|---|
| | CANCER GENE: mCG14290/hCG23314 |
| 367. | MOUSE GENOMIC SEQUENCE (mCG14290) |
| 368. | MOUSE mRNA SEQUENCE (mCT15414) |
| 369. | MOUSE PROTEIN SEQUENCE (mCP12312) |
| 370. | HUMAN GENOMIC SEQUENCE (hCG23314) |
| 371. | HUMAN mRNA SEQUENCE (hCT14420) |
| 372. | HUMAN PROTEIN SEQUENCE (hCP42485) |
| | CANCER GENE: mCG14414/hCG1641631 |
| 373. | MOUSE GENOMIC SEQUENCE (mCG14414) |
| 374. | MOUSE mRNA SEQUENCE (mCT16804) |
| 375. | MOUSE PROTEIN SEQUENCE (mCP17423) |
| 376. | HUMAN GENOMIC SEQUENCE (hCG1641631) |
| 377. | HUMAN mRNA SEQUENCE (hCT1641758) |
| 378. | HUMAN PROTEIN SEQUENCE (hCP1624000) |
| | CANCER GENE: mCG14521/hCG23105 |
| 379. | MOUSE GENOMIC SEQUENCE (mCG14521) |
| 380. | MOUSE mRNA SEQUENCE (mCT18340) |
| 381. | MOUSE PROTEIN SEQUENCE (mCP7400) |
| 382. | HUMAN GENOMIC SEQUENCE (hCG23105) |
| 383. | HUMAN mRNA SEQUENCE (hCT14209) |
| 384. | HUMAN PROTEIN SEQUENCE (hCP40550) |
| | CANCER GENE: mCG14555/hCG23727 |
| 385. | MOUSE GENOMIC SEQUENCE (mCG14555) |
| 386. | MOUSE mRNA SEQUENCE (mCT18260) |
| 387. | MOUSE PROTEIN SEQUENCE (mCP2400) |
| 388. | HUMAN GENOMIC SEQUENCE (hCG23727) |
| 389. | HUMAN mRNA SEQUENCE (hCT14839) |
| 390. | HUMAN PROTEIN SEQUENCE (hCP41563) |
| | CANCER GENE: mCG14611/hCG38337 |
| 391. | MOUSE GENOMIC SEQUENCE (mCG14611) |
| 392. | MOUSE mRNA SEQUENCE (mCT19379) |
| 393. | MOUSE PROTEIN SEQUENCE (mCP5898) |
| 394. | HUMAN GENOMIC SEQUENCE (hCG38337) |
| 395. | HUMAN mRNA SEQUENCE (hCT29578) |
| 396. | HUMAN PROTEIN SEQUENCE (hCP48239) |
| | CANCER GENE: mCG14624/hCG32448 |
| 397. | MOUSE GENOMIC SEQUENCE (mCG14624) |
| 398. | MOUSE mRNA SEQUENCE (mCT19082) |
| 399. | MOUSE PROTEIN SEQUENCE (mCP7195) |
| 400. | HUMAN GENOMIC SEQUENCE (hCG32448) |
| 401. | HUMAN mRNA SEQUENCE (hCT1958762) |
| 402. | HUMAN PROTEIN SEQUENCE (hCP1762529) |
| | CANCER GENE: mCG14659/hCG23908 |
| 403. | MOUSE GENOMIC SEQUENCE (mCG14659) |
| 404. | MOUSE mRNA SEQUENCE (mCT19290) |
| 405. | MOUSE PROTEIN SEQUENCE (mCP22629) |
| 406. | HUMAN GENOMIC SEQUENCE (hCG23908) |
| 407. | HUMAN mRNA SEQUENCE (hCT15021) |
| 408. | HUMAN PROTEIN SEQUENCE (hCP41309) |
| | CANCER GENE: mCG1468/hCG32770 |
| 409. | MOUSE GENOMIC SEQUENCE (mCG1468) |
| 410. | MOUSE mRNA SEQUENCE (mCT8256) |
| 411. | MOUSE PROTEIN SEQUENCE (mCP14101) |
| 412. | HUMAN GENOMIC SEQUENCE (hCG32770) |
| 413. | HUMAN mRNA SEQUENCE (hCT23961) |
| 414. | HUMAN PROTEIN SEQUENCE (hCP46106) |
| | CANCER GENE: mCG14749/hCG16187 |
| 415. | MOUSE GENOMIC SEQUENCE (mCG14749) |
| 416. | MOUSE mRNA SEQUENCE (mCT19814) |
| 417. | MOUSE PROTEIN SEQUENCE (mCP21367) |
| 418. | HUMAN GENOMIC SEQUENCE (hCG16187) |
| 419. | HUMAN mRNA SEQUENCE (hCT7219) |
| 420. | HUMAN PROTEIN SEQUENCE (hCP33910) |

TABLE 2-continued

IDENTIFICATION OF SEQUENCES

| SEQ ID NOS. | SEQUENCES |
|---|---|
| | CANCER GENE: mCG14817/hCG17311 |
| 421. | MOUSE GENOMIC SEQUENCE (mCG14817) |
| 422. | MOUSE mRNA SEQUENCE (mCT20556) |
| 423. | MOUSE PROTEIN SEQUENCE (mCP3529) |
| 424. | HUMAN GENOMIC SEQUENCE (hCG17311) |
| 425. | HUMAN mRNA SEQUENCE (hCT8361) |
| 426. | HUMAN PROTEIN SEQUENCE (hCP34118) |
| | CANCER GENE: mCG14883/hCG1736594 |
| 427. | MOUSE GENOMIC SEQUENCE (mCG14883) |
| 428. | MOUSE mRNA SEQUENCE (mCT20678) |
| 429. | MOUSE PROTEIN SEQUENCE (mCP13935) |
| 430. | HUMAN GENOMIC SEQUENCE (hCG1736594) |
| 431. | HUMAN mRNA SEQUENCE (hCT1774609) |
| 432. | HUMAN PROTEIN SEQUENCE (hCP1717577) |
| | CANCER GENE: mCG14932/hCG24749 |
| 433. | MOUSE GENOMIC SEQUENCE (mCG14932) |
| 434. | MOUSE mRNA SEQUENCE (mCT21048) |
| 435. | MOUSE PROTEIN SEQUENCE (mCP14256) |
| 436. | HUMAN GENOMIC SEQUENCE (hCG24749) |
| 437. | HUMAN mRNA SEQUENCE (hCT15869) |
| 438. | HUMAN PROTEIN SEQUENCE (hCP41876) |
| | CANCER GENE: mCG14989/hCG1646502 |
| 439. | MOUSE GENOMIC SEQUENCE (mCG14989) |
| 440. | MOUSE mRNA SEQUENCE (mCT21342) |
| 441. | MOUSE PROTEIN SEQUENCE (mCP16457) |
| 442. | HUMAN GENOMIC SEQUENCE (hCG1646502) |
| 443. | HUMAN mRNA SEQUENCE (hCT1646629) |
| 444. | HUMAN PROTEIN SEQUENCE (hCP1641181) |
| | CANCER GENE: mCG15039/hCG28572 |
| 445. | MOUSE GENOMIC SEQUENCE (mCG15039) |
| 446. | MOUSE mRNA SEQUENCE (mCT12903) |
| 447. | MOUSE PROTEIN SEQUENCE (mCP18813) |
| 448. | HUMAN GENOMIC SEQUENCE (hCG28572) |
| 449. | HUMAN mRNA SEQUENCE (hCT19726) |
| 450. | HUMAN PROTEIN SEQUENCE (hCP44008) |
| | CANCER GENE: mCG15044/hCG27278 |
| 451. | MOUSE GENOMIC SEQUENCE (mCG15044) |
| 452. | MOUSE mRNA SEQUENCE (mCT12890) |
| 453. | MOUSE PROTEIN SEQUENCE (mCP18960) |
| 454. | HUMAN GENOMIC SEQUENCE (hCG27278) |
| 455. | HUMAN mRNA SEQUENCE (hCT18416) |
| 456. | HUMAN PROTEIN SEQUENCE (hCP43286) |
| | CANCER GENE: mCG15048/hCG28567 |
| 457. | MOUSE GENOMIC SEQUENCE (mCG15048) |
| 458. | MOUSE mRNA SEQUENCE (mCT12877) |
| 459. | MOUSE PROTEIN SEQUENCE (mCP18885) |
| 460. | HUMAN GENOMIC SEQUENCE (hCG28567) |
| 461. | HUMAN mRNA SEQUENCE (hCT1814688) |
| 462. | HUMAN PROTEIN SEQUENCE (hCP1741102) |
| | CANCER GENE: mCG15184/hCG1783275 |
| 463. | MOUSE GENOMIC SEQUENCE (mCG15184) |
| 464. | MOUSE mRNA SEQUENCE (mCT14470) |
| 465. | MOUSE PROTEIN SEQUENCE (mCP17972) |
| 466. | HUMAN GENOMIC SEQUENCE (hCG1783275) |
| 467. | HUMAN mRNA SEQUENCE (hCT1822211) |
| 468. | HUMAN PROTEIN SEQUENCE (hCP1709817) |
| | CANCER GENE: mCG15331/hCG1640186 |
| 469. | MOUSE GENOMIC SEQUENCE (mCG15331) |
| 470. | MOUSE mRNA SEQUENCE (mCT15478) |
| 471. | MOUSE PROTEIN SEQUENCE (mCP20056) |
| 472. | HUMAN GENOMIC SEQUENCE (hCG1640186) |
| 473. | HUMAN mRNA SEQUENCE (hCT1640313) |
| 474. | HUMAN PROTEIN SEQUENCE (hCP1643394) |
| | CANCER GENE: mCG15379/hCG1643838 |
| 475. | MOUSE GENOMIC SEQUENCE (mCG15379) |
| 476. | MOUSE mRNA SEQUENCE (mCT10709) |
| 477. | MOUSE PROTEIN SEQUENCE (mCP23575) |
| 478. | HUMAN GENOMIC SEQUENCE (hCG1643838) |
| 479. | HUMAN mRNA SEQUENCE (hCT1643965) |
| 480. | HUMAN PROTEIN SEQUENCE (hCP1604810) |
| | CANCER GENE: mCG15397/hCG39530 |
| 481. | MOUSE GENOMIC SEQUENCE (mCG15397) |
| 482. | MOUSE mRNA SEQUENCE (mCT15954) |
| 483. | MOUSE PROTEIN SEQUENCE (mCP5676) |
| 484. | HUMAN GENOMIC SEQUENCE (hCG39530) |
| 485. | HUMAN mRNA SEQUENCE (hCT30781) |
| 486. | HUMAN PROTEIN SEQUENCE (hCP49320) |
| | CANCER GENE: mCG15498/hCG15009 |
| 487. | MOUSE GENOMIC SEQUENCE (mCG15498) |
| 488. | MOUSE mRNA SEQUENCE (mCT17826) |
| 489. | MOUSE PROTEIN SEQUENCE (mCP18112) |
| 490. | HUMAN GENOMIC SEQUENCE (hCG15009) |
| 491. | HUMAN mRNA SEQUENCE (hCT6030) |
| 492. | HUMAN PROTEIN SEQUENCE (hCP35899) |
| | CANCER GENE: mCG15520/hCG36837 |
| 493. | MOUSE GENOMIC SEQUENCE (mCG15520) |
| 494. | MOUSE mRNA SEQUENCE (mCT17722) |
| 495. | MOUSE PROTEIN SEQUENCE (mCP20948) |
| 496. | HUMAN GENOMIC SEQUENCE (hCG36837) |
| 497. | HUMAN mRNA SEQUENCE (hCT1950131) |
| 498. | HUMAN PROTEIN SEQUENCE (hCP1763610) |
| | CANCER GENE: mCG15521/hCG37331 |
| 499. | MOUSE GENOMIC SEQUENCE (mCG15521) |
| 500. | MOUSE mRNA SEQUENCE (mCT17719) |
| 501. | MOUSE PROTEIN SEQUENCE (mCP20949) |
| 502. | HUMAN GENOMIC SEQUENCE (hCG37331) |
| 503. | HUMAN mRNA SEQUENCE (hCT28564) |
| 504. | HUMAN PROTEIN SEQUENCE (hCP47335) |
| | CANCER GENE: mCG15594/hCG15786 |
| 505. | MOUSE GENOMIC SEQUENCE (mCG15594) |
| 506. | MOUSE mRNA SEQUENCE (mCT18732) |
| 507. | MOUSE PROTEIN SEQUENCE (mCP23704) |
| 508. | HUMAN GENOMIC SEQUENCE (hCG15786) |
| 509. | HUMAN mRNA SEQUENCE (hCT6815) |
| 510. | HUMAN PROTEIN SEQUENCE (hCP34293) |
| | CANCER GENE: mCG15699/hCG27588 |
| 511. | MOUSE GENOMIC SEQUENCE (mCG15699) |
| 512. | MOUSE mRNA SEQUENCE (mCT18581) |
| 513. | MOUSE PROTEIN SEQUENCE (mCP7304) |
| 514. | HUMAN GENOMIC SEQUENCE (hCG27588) |
| 515. | HUMAN mRNA SEQUENCE (hCT18729) |
| 516. | HUMAN PROTEIN SEQUENCE (hCP43155) |
| | CANCER GENE: mCG15703/hCG23995 |
| 517. | MOUSE GENOMIC SEQUENCE (mCG15703) |
| 518. | MOUSE mRNA SEQUENCE (mCT19437) |
| 519. | MOUSE PROTEIN SEQUENCE (mCP2310) |
| 520. | HUMAN GENOMIC SEQUENCE (hCG23995) |
| 521. | HUMAN mRNA SEQUENCE (hCT15109) |
| 522. | HUMAN PROTEIN SEQUENCE (hCP41355) |
| | CANCER GENE: mCG15868/hCG19397 |
| 523. | MOUSE GENOMIC SEQUENCE (mCG15868) |
| 524. | MOUSE mRNA SEQUENCE (mCT12593) |
| 525. | MOUSE PROTEIN SEQUENCE (mCP15102) |
| 526. | HUMAN GENOMIC SEQUENCE (hCG19397) |
| 527. | HUMAN mRNA SEQUENCE (hCT10466) |
| 528. | HUMAN PROTEIN SEQUENCE (hCP37122) |

TABLE 2-continued

IDENTIFICATION OF SEQUENCES

| SEQ ID NOS. | SEQUENCES |
|---|---|
| | CANCER GENE: mCG15870/hCG18268 |
| 529. | MOUSE GENOMIC SEQUENCE (mCG15870) |
| 530. | MOUSE mRNA SEQUENCE (mCT12595) |
| 531. | MOUSE PROTEIN SEQUENCE (mCP15106) |
| 532. | HUMAN GENOMIC SEQUENCE (hCG18268) |
| 533. | HUMAN mRNA SEQUENCE (hCT9326) |
| 534. | HUMAN PROTEIN SEQUENCE (hCP36124) |
| | CANCER GENE: mCG1589/hCG28214 |
| 535. | MOUSE GENOMIC SEQUENCE (mCG1589) |
| 536. | MOUSE mRNA SEQUENCE (mCT8415) |
| 537. | MOUSE PROTEIN SEQUENCE (mCP13496) |
| 538. | HUMAN GENOMIC SEQUENCE (hCG28214) |
| 539. | HUMAN mRNA SEQUENCE (hCT19362) |
| 540. | HUMAN PROTEIN SEQUENCE (hCP44085) |
| | CANCER GENE: mCG1596/hCG28803 |
| 541. | MOUSE GENOMIC SEQUENCE (mCG1596) |
| 542. | MOUSE mRNA SEQUENCE (mCT8422) |
| 543. | MOUSE PROTEIN SEQUENCE (mCP13477) |
| 544. | HUMAN GENOMIC SEQUENCE (hCG28803) |
| 545. | HUMAN mRNA SEQUENCE (hCT19958) |
| 546. | HUMAN PROTEIN SEQUENCE (hCP44159) |
| | CANCER GENE: mCG15964/hCG1762872 |
| 547. | MOUSE GENOMIC SEQUENCE (mCG15964) |
| 548. | MOUSE mRNA SEQUENCE (mCT14238) |
| 549. | MOUSE PROTEIN SEQUENCE (mCP21067) |
| 550. | HUMAN GENOMIC SEQUENCE (hCG1762872) |
| 551. | HUMAN mRNA SEQUENCE (hCT1801372) |
| 552. | HUMAN PROTEIN SEQUENCE (hCP1720579) |
| | CANCER GENE: mCG16052/hCG15409 |
| 553. | MOUSE GENOMIC SEQUENCE (mCG16052) |
| 554. | MOUSE mRNA SEQUENCE (mCT15245) |
| 555. | MOUSE PROTEIN SEQUENCE (mCP8454) |
| 556. | HUMAN GENOMIC SEQUENCE (hCG15409) |
| 557. | HUMAN mRNA SEQUENCE (hCT6431) |
| 558. | HUMAN PROTEIN SEQUENCE (hCP35788) |
| | CANCER GENE: mCG16071/hCG23219 |
| 559. | MOUSE GENOMIC SEQUENCE (mCG16071) |
| 560. | MOUSE mRNA SEQUENCE (mCT15608) |
| 561. | MOUSE PROTEIN SEQUENCE (mCP22427) |
| 562. | HUMAN GENOMIC SEQUENCE (hCG23219) |
| 563. | HUMAN mRNA SEQUENCE (hCT14324) |
| 564. | HUMAN PROTEIN SEQUENCE (hCP40628) |
| | CANCER GENE: mCG16088/hCG33697 |
| 565. | MOUSE GENOMIC SEQUENCE (mCG16088) |
| 566. | MOUSE mRNA SEQUENCE (mCT15460) |
| 567. | MOUSE PROTEIN SEQUENCE (mCP22413) |
| 568. | HUMAN GENOMIC SEQUENCE (hCG33697) |
| 569. | HUMAN mRNA SEQUENCE (hCT1686732) |
| 570. | HUMAN PROTEIN SEQUENCE (hCP1689982) |
| | CANCER GENE: mCG16239/hCG21559 |
| 571. | MOUSE GENOMIC SEQUENCE (mCG16239) |
| 572. | MOUSE mRNA SEQUENCE (mCT16666) |
| 573. | MOUSE PROTEIN SEQUENCE (mCP12669) |
| 574. | HUMAN GENOMIC SEQUENCE (hCG21559) |
| 575. | HUMAN mRNA SEQUENCE (hCT12651) |
| 576. | HUMAN PROTEIN SEQUENCE (hCP39092) |
| | CANCER GENE: mCG16291/hCG1737652 |
| 577. | MOUSE GENOMIC SEQUENCE (mCG16291) |
| 578. | MOUSE mRNA SEQUENCE (mCT17032) |
| 579. | MOUSE PROTEIN SEQUENCE (mCP21575) |
| 580. | HUMAN GENOMIC SEQUENCE (hCG1737652) |
| 581. | HUMAN mRNA SEQUENCE (hCT1775695) |
| 582. | HUMAN PROTEIN SEQUENCE (hCP1712193) |
| | CANCER GENE: mCG16365/hCG1640204 |
| 583. | MOUSE GENOMIC SEQUENCE (mCG16365) |
| 584. | MOUSE mRNA SEQUENCE (mCT17616) |
| 585. | MOUSE PROTEIN SEQUENCE (mCP8330) |
| 586. | HUMAN GENOMIC SEQUENCE (hCG1640204) |
| 587. | HUMAN mRNA SEQUENCE (hCT1640331) |
| 588. | HUMAN PROTEIN SEQUENCE (hCP1627012) |
| | CANCER GENE: mCG16394/hCG20537 |
| 589. | MOUSE GENOMIC SEQUENCE (mCG16394) |
| 590. | MOUSE mRNA SEQUENCE (mCT17518) |
| 591. | MOUSE PROTEIN SEQUENCE (mCP4839) |
| 592. | HUMAN GENOMIC SEQUENCE (hCG20537) |
| 593. | HUMAN mRNA SEQUENCE (hCT11616) |
| 594. | HUMAN PROTEIN SEQUENCE (hCP38217) |
| | CANCER GENE: mCG16401/hCG20994 |
| 595. | MOUSE GENOMIC SEQUENCE (mCG16401) |
| 596. | MOUSE mRNA SEQUENCE (mCT17724) |
| 597. | MOUSE PROTEIN SEQUENCE (mCP3126) |
| 598. | HUMAN GENOMIC SEQUENCE (hCG20994) |
| 599. | HUMAN mRNA SEQUENCE (hCT12078) |
| 600. | HUMAN PROTEIN SEQUENCE (hCP38844) |
| | CANCER GENE: mCG1647/hCG25929 |
| 601. | MOUSE GENOMIC SEQUENCE (mCG1647) |
| 602. | MOUSE mRNA SEQUENCE (mCT7922) |
| 603. | MOUSE PROTEIN SEQUENCE (mCP21806) |
| 604. | HUMAN GENOMIC SEQUENCE (hCG25929) |
| 605. | HUMAN mRNA SEQUENCE (hCT17057) |
| 606. | HUMAN PROTEIN SEQUENCE (hCP42506) |
| | CANCER GENE: mCG1659/hCG32809 |
| 607. | MOUSE GENOMIC SEQUENCE (mCG1659) |
| 608. | MOUSE mRNA SEQUENCE (mCT8196) |
| 609. | MOUSE PROTEIN SEQUENCE (mCP21822) |
| 610. | HUMAN GENOMIC SEQUENCE (hCG32809) |
| 611. | HUMAN mRNA SEQUENCE (hCT24001) |
| 612. | HUMAN PROTEIN SEQUENCE (hCP46172) |
| | CANCER GENE: mCG16601/hCG17315 |
| 613. | MOUSE GENOMIC SEQUENCE (mCG16601) |
| 614. | MOUSE mRNA SEQUENCE (mCT19044) |
| 615. | MOUSE PROTEIN SEQUENCE (mCP8830) |
| 616. | HUMAN GENOMIC SEQUENCE (hCG17315) |
| 617. | HUMAN mRNA SEQUENCE (hCT8365) |
| 618. | HUMAN PROTEIN SEQUENCE (hCP34268) |
| | CANCER GENE: mCG16720/hCG18035 |
| 619. | MOUSE GENOMIC SEQUENCE (mCG16720) |
| 620. | MOUSE mRNA SEQUENCE (mCT12987) |
| 621. | MOUSE PROTEIN SEQUENCE (mCP8906) |
| 622. | HUMAN GENOMIC SEQUENCE (hCG18035) |
| 623. | HUMAN mRNA SEQUENCE (hCT9090) |
| 624. | HUMAN PROTEIN SEQUENCE (hCP36078) |
| | CANCER GENE: mCG16843/hCG37968 |
| 625. | MOUSE GENOMIC SEQUENCE (mCG16843) |
| 626. | MOUSE mRNA SEQUENCE (mCT14357) |
| 627. | MOUSE PROTEIN SEQUENCE (mCP9711) |
| 628. | HUMAN GENOMIC SEQUENCE (hCG37968) |
| 629. | HUMAN mRNA SEQUENCE (hCT29205) |
| 630. | HUMAN PROTEIN SEQUENCE (hCP47985) |
| | CANCER GENE: mCG16845/hCG37971 |
| 631. | MOUSE GENOMIC SEQUENCE (mCG16845) |
| 632. | MOUSE mRNA SEQUENCE (mCT14351) |
| 633. | MOUSE PROTEIN SEQUENCE (mCP9550) |
| 634. | HUMAN GENOMIC SEQUENCE (hCG37971) |
| 635. | HUMAN mRNA SEQUENCE (hCT29208) |
| 636. | HUMAN PROTEIN SEQUENCE (hCP47989) |

TABLE 2-continued

IDENTIFICATION OF SEQUENCES

| SEQ ID NOS. | SEQUENCES |
|---|---|
| | CANCER GENE: mCG16880/hCG22479 |
| 637. | MOUSE GENOMIC SEQUENCE (mCG16880) |
| 638. | MOUSE mRNA SEQUENCE (mCT14257) |
| 639. | MOUSE PROTEIN SEQUENCE (mCP16563) |
| 640. | HUMAN GENOMIC SEQUENCE (hCG22479) |
| 641. | HUMAN mRNA SEQUENCE (hCT13576) |
| 642. | HUMAN PROTEIN SEQUENCE (hCP39968) |
| | CANCER GENE: mCG16923/hCG25643 |
| 643. | MOUSE GENOMIC SEQUENCE (mCG16923) |
| 644. | MOUSE mRNA SEQUENCE (mCT14870) |
| 645. | MOUSE PROTEIN SEQUENCE (mCP15343) |
| 646. | HUMAN GENOMIC SEQUENCE (hCG25643) |
| 647. | HUMAN mRNA SEQUENCE (hCT16768) |
| 648. | HUMAN PROTEIN SEQUENCE (hCP42329) |
| | CANCER GENE: mCG16959/hCG25303 |
| 649. | MOUSE GENOMIC SEQUENCE (mCG16959) |
| 650. | MOUSE mRNA SEQUENCE (mCT14701) |
| 651. | MOUSE PROTEIN SEQUENCE (mCP12909) |
| 652. | HUMAN GENOMIC SEQUENCE (hCG25303) |
| 653. | HUMAN mRNA SEQUENCE (hCT16428) |
| 654. | HUMAN PROTEIN SEQUENCE (hCP42229) |
| | CANCER GENE: mCG16994/hCG36856 |
| 655. | MOUSE GENOMIC SEQUENCE (mCG16994) |
| 656. | MOUSE mRNA SEQUENCE (mCT15290) |
| 657. | MOUSE PROTEIN SEQUENCE (mCP12482) |
| 658. | HUMAN GENOMIC SEQUENCE (hCG36856) |
| 659. | HUMAN mRNA SEQUENCE (hCT28086) |
| 660. | HUMAN PROTEIN SEQUENCE (hCP47065) |
| | CANCER GENE: mCG17013/hCG24994 |
| 661. | MOUSE GENOMIC SEQUENCE (mCG17013) |
| 662. | MOUSE mRNA SEQUENCE (mCT15957) |
| 663. | MOUSE PROTEIN SEQUENCE (mCP4389) |
| 664. | HUMAN GENOMIC SEQUENCE (hCG24994) |
| 665. | HUMAN mRNA SEQUENCE (hCT16115) |
| 666. | HUMAN PROTEIN SEQUENCE (hCP42010) |
| | CANCER GENE: mCG17035/hCG1778746 |
| 667. | MOUSE GENOMIC SEQUENCE (mCG17035) |
| 668. | MOUSE mRNA SEQUENCE (mCT15983) |
| 669. | MOUSE PROTEIN SEQUENCE (mCP4460) |
| 670. | HUMAN GENOMIC SEQUENCE (hCG1778746) |
| 671. | HUMAN mRNA SEQUENCE (hCT1817524) |
| 672. | HUMAN PROTEIN SEQUENCE (hCP1725406) |
| | CANCER GENE: mCG17138/hCG33187 |
| 673. | MOUSE GENOMIC SEQUENCE (mCG17138) |
| 674. | MOUSE mRNA SEQUENCE (mCT16443) |
| 675. | MOUSE PROTEIN SEQUENCE (mCP12938) |
| 676. | HUMAN GENOMIC SEQUENCE (hCG33187) |
| 677. | HUMAN mRNA SEQUENCE (hCT24380) |
| 678. | HUMAN PROTEIN SEQUENCE (hCP46555) |
| | CANCER GENE: mCG17164/hCG40741 |
| 679. | MOUSE GENOMIC SEQUENCE (mCG17164) |
| 680. | MOUSE mRNA SEQUENCE (mCT16512) |
| 681. | MOUSE PROTEIN SEQUENCE (mCP1077) |
| 682. | HUMAN GENOMIC SEQUENCE (hCG40741) |
| 683. | HUMAN mRNA SEQUENCE (hCT32001) |
| 684. | HUMAN PROTEIN SEQUENCE (hCP50502) |
| | CANCER GENE: mCG17208/hCG40378 |
| 685. | MOUSE GENOMIC SEQUENCE (mCG17208) |
| 686. | MOUSE mRNA SEQUENCE (mCT16566) |
| 687. | MOUSE PROTEIN SEQUENCE (mCP5428) |
| 688. | HUMAN GENOMIC SEQUENCE (hCG40378) |
| 689. | HUMAN mRNA SEQUENCE (hCT1820899) |
| 690. | HUMAN PROTEIN SEQUENCE (hCP1735072) |
| | CANCER GENE: mCG17242/hCG25680 |
| 691. | MOUSE GENOMIC SEQUENCE (mCG17242) |
| 692. | MOUSE mRNA SEQUENCE (mCT12837) |
| 693. | MOUSE PROTEIN SEQUENCE (mCP17611) |
| 694. | HUMAN GENOMIC SEQUENCE (hCG25680) |
| 695. | HUMAN mRNA SEQUENCE (hCT16805) |
| 696. | HUMAN PROTEIN SEQUENCE (hCP42378) |
| | CANCER GENE: mCG17259/hCG19476 |
| 697. | MOUSE GENOMIC SEQUENCE (mCG17259) |
| 698. | MOUSE mRNA SEQUENCE (mCT16960) |
| 699. | MOUSE PROTEIN SEQUENCE (mCP13878) |
| 700. | HUMAN GENOMIC SEQUENCE (hCG19476) OK |
| 701. | HUMAN mRNA SEQUENCE (hCT10546) |
| 702. | HUMAN PROTEIN SEQUENCE (hCP37525) |
| | CANCER GENE: mCG17323/hCG32158 |
| 703. | MOUSE GENOMIC SEQUENCE (mCG17323) |
| 704. | MOUSE mRNA SEQUENCE (mCT17574) |
| 705. | MOUSE PROTEIN SEQUENCE (mCP9792) |
| 706. | HUMAN GENOMIC SEQUENCE (hCG32158) |
| 707. | HUMAN mRNA SEQUENCE (hCT23346) |
| 708. | HUMAN PROTEIN SEQUENCE (hCP46392) |
| | CANCER GENE: mCG17383/hCG28354 |
| 709. | MOUSE GENOMIC SEQUENCE (mCG17383) |
| 710. | MOUSE mRNA SEQUENCE (mCT18403) |
| 711. | MOUSE PROTEIN SEQUENCE (mCP18722) |
| 712. | HUMAN GENOMIC SEQUENCE (hCG28354) |
| 713. | HUMAN mRNA SEQUENCE (hCT19506) |
| 714. | HUMAN PROTEIN SEQUENCE (hCP43838) |
| | CANCER GENE: mCG17557/hCG99255 |
| 715. | MOUSE GENOMIC SEQUENCE (mCG17557) |
| 716. | MOUSE mRNA SEQUENCE (mCT14213) |
| 717. | MOUSE PROTEIN SEQUENCE (mCP17279) |
| 718. | HUMAN GENOMIC SEQUENCE (hCG99255) |
| 719. | HUMAN mRNA SEQUENCE (hCT1950804) |
| 720. | HUMAN PROTEIN SEQUENCE (hCP1764431) |
| | CANCER GENE: mCG17867/hCG33515 |
| 721. | MOUSE GENOMIC SEQUENCE (mCG17867) |
| 722. | MOUSE mRNA SEQUENCE (mCT16792) |
| 723. | MOUSE PROTEIN SEQUENCE (mCP6346) |
| 724. | HUMAN GENOMIC SEQUENCE (hCG33515) |
| 725. | HUMAN mRNA SEQUENCE (hCT24713) |
| 726. | HUMAN PROTEIN SEQUENCE (hCP46767) |
| | CANCER GENE: mCG17870/hCG32959 |
| 727. | MOUSE GENOMIC SEQUENCE (mCG17870) |
| 728. | MOUSE mRNA SEQUENCE (mCT16795) |
| 729. | MOUSE PROTEIN SEQUENCE (mCP6341) |
| 730. | HUMAN GENOMIC SEQUENCE (hCG32959) |
| 731. | HUMAN mRNA SEQUENCE (hCT24151) |
| 732. | HUMAN PROTEIN SEQUENCE (hCP46769) |
| | CANCER GENE: mCG17886/hCG20908 |
| 733. | MOUSE GENOMIC SEQUENCE (mCG17886) |
| 734. | MOUSE mRNA SEQUENCE (mCT16809) |
| 735. | MOUSE PROTEIN SEQUENCE (mCP15214) |
| 736. | HUMAN GENOMIC SEQUENCE (hCG20908) |
| 737. | HUMAN mRNA SEQUENCE (hCT11990) |
| 738. | HUMAN PROTEIN SEQUENCE (hCP40309) |
| | CANCER GENE: mCG17943/hCG17932 |
| 739. | MOUSE GENOMIC SEQUENCE (mCG17943) |
| 740. | MOUSE mRNA SEQUENCE (mCT17820) |
| 741. | MOUSE PROTEIN SEQUENCE (mCP12846) |
| 742. | HUMAN GENOMIC SEQUENCE (hCG17932) |
| 743. | HUMAN mRNA SEQUENCE (hCT8986) |
| 744. | HUMAN PROTEIN SEQUENCE (hCP36538) |

TABLE 2-continued

IDENTIFICATION OF SEQUENCES

| SEQ ID NOS. | SEQUENCES |
|---|---|
| | CANCER GENE: mCG17984/hCG33404 |
| 745. | MOUSE GENOMIC SEQUENCE (mCG17984) |
| 746. | MOUSE mRNA SEQUENCE (mCT18062) |
| 747. | MOUSE PROTEIN SEQUENCE (mCP22360) |
| 748. | HUMAN GENOMIC SEQUENCE (hCG33404) |
| 749. | HUMAN mRNA SEQUENCE (hCT24598) |
| 750. | HUMAN PROTEIN SEQUENCE (hCP46712) |
| | CANCER GENE: mCG18016/hCG17121 |
| 751. | MOUSE GENOMIC SEQUENCE (mCG18016) |
| 752. | MOUSE mRNA SEQUENCE (mCT18967) |
| 753. | MOUSE PROTEIN SEQUENCE (mCP8856) |
| 754. | HUMAN GENOMIC SEQUENCE (hCG17121) |
| 755. | HUMAN mRNA SEQUENCE (hCT8169) |
| 756. | HUMAN PROTEIN SEQUENCE (hCP36778) |
| | CANCER GENE: mCG18026/hCG17346 |
| 757. | MOUSE GENOMIC SEQUENCE (mCG18026) |
| 758. | MOUSE mRNA SEQUENCE (mCT18976) |
| 759. | MOUSE PROTEIN SEQUENCE (mCP8941) |
| 760. | HUMAN GENOMIC SEQUENCE (hCG17346) |
| 761. | HUMAN mRNA SEQUENCE (hCT8396) |
| 762. | HUMAN PROTEIN SEQUENCE (hCP33988) |
| | CANCER GENE: mCG18081/hCG38701 |
| 763. | MOUSE GENOMIC SEQUENCE (mCG18081) |
| 764. | MOUSE mRNA SEQUENCE (mCT19515) |
| 765. | MOUSE PROTEIN SEQUENCE (mCP17668) |
| 766. | HUMAN GENOMIC SEQUENCE (hCG38701) |
| 767. | HUMAN mRNA SEQUENCE (hCT29945) |
| 768. | HUMAN PROTEIN SEQUENCE (hCP48559) |
| | CANCER GENE: mCG18084/hCG39597 |
| 769. | MOUSE GENOMIC SEQUENCE (mCG18084) |
| 770. | MOUSE mRNA SEQUENCE (mCT19672) |
| 771. | MOUSE PROTEIN SEQUENCE (mCP9465) |
| 772. | HUMAN GENOMIC SEQUENCE (hCG39597) |
| 773. | HUMAN mRNA SEQUENCE (hCT30849) |
| 774. | HUMAN PROTEIN SEQUENCE (hCP51029) |
| | CANCER GENE: mCG18240/hCG18999 |
| 775. | MOUSE GENOMIC SEQUENCE (mCG18240) |
| 776. | MOUSE mRNA SEQUENCE (mCT12803) |
| 777. | MOUSE PROTEIN SEQUENCE (mCP15553) |
| 778. | HUMAN GENOMIC SEQUENCE (hCG18999) |
| 779. | HUMAN mRNA SEQUENCE (hCT10064) |
| 780. | HUMAN PROTEIN SEQUENCE (hCP37164) |
| | CANCER GENE: mCG1828/hCG1640193 |
| 781. | MOUSE GENOMIC SEQUENCE (mCG1828) |
| 782. | MOUSE mRNA SEQUENCE (mCT7778) |
| 783. | MOUSE PROTEIN SEQUENCE (mCP20760) |
| 784. | HUMAN GENOMIC SEQUENCE (hCG1640193) |
| 785. | HUMAN mRNA SEQUENCE (hCT1640320) |
| 786. | HUMAN PROTEIN SEQUENCE (hCP1630135) |
| | CANCER GENE: mCG18281/hCG16651 |
| 787. | MOUSE GENOMIC SEQUENCE (mCG18281) |
| 788. | MOUSE mRNA SEQUENCE (mCT12157) |
| 789. | MOUSE PROTEIN SEQUENCE (mCP1250) |
| 790. | HUMAN GENOMIC SEQUENCE (hCG16651) |
| 791. | HUMAN mRNA SEQUENCE (hCT7691) |
| 792. | HUMAN PROTEIN SEQUENCE (hCP37038) |
| | CANCER GENE: mCG18404/hCG20204 |
| 793. | MOUSE GENOMIC SEQUENCE (mCG18404) |
| 794. | MOUSE mRNA SEQUENCE (mCT11039) |
| 795. | MOUSE PROTEIN SEQUENCE (mCP9566) |
| 796. | HUMAN GENOMIC SEQUENCE (hCG20204) |
| 797. | HUMAN mRNA SEQUENCE (hCT11279) |
| 798. | HUMAN PROTEIN SEQUENCE (hCP37942) |
| | CANCER GENE: mCG18525/hCG15773 |
| 799. | MOUSE GENOMIC SEQUENCE (mCG18525) |
| 800. | MOUSE mRNA SEQUENCE (mCT14781) |
| 801. | MOUSE PROTEIN SEQUENCE (mCP23199) |
| 802. | HUMAN GENOMIC SEQUENCE (hCG15773) |
| 803. | HUMAN mRNA SEQUENCE (hCT6802) |
| 804. | HUMAN PROTEIN SEQUENCE (hCP35354) |
| | CANCER GENE: mCG18554/hCG18551 |
| 805. | MOUSE GENOMIC SEQUENCE (mCG18554) |
| 806. | MOUSE mRNA SEQUENCE (mCT14744) |
| 807. | MOUSE PROTEIN SEQUENCE (mCP19483) |
| 808. | HUMAN GENOMIC SEQUENCE (hCG18551) |
| 809. | HUMAN mRNA SEQUENCE (hCT1950575) |
| 810. | HUMAN PROTEIN SEQUENCE (hCP1752475) |
| | CANCER GENE: mCG18573/hCG18549 |
| 811. | MOUSE GENOMIC SEQUENCE (mCG18573) |
| 812. | MOUSE mRNA SEQUENCE (mCT14853) |
| 813. | MOUSE PROTEIN SEQUENCE (mCP19435) |
| 814. | HUMAN GENOMIC SEQUENCE (hCG18549) |
| 815. | HUMAN mRNA SEQUENCE (hCT1950572) |
| 816. | HUMAN PROTEIN SEQUENCE (hCP1766593) |
| | CANCER GENE: mCG18577/hCG28278 |
| 817. | MOUSE GENOMIC SEQUENCE (mCG18577) |
| 818. | MOUSE mRNA SEQUENCE (mCT14857) |
| 819. | MOUSE PROTEIN SEQUENCE (mCP19656) |
| 820. | HUMAN GENOMIC SEQUENCE (hCG28278) |
| 821. | HUMAN mRNA SEQUENCE (hCT19426) |
| 822. | HUMAN PROTEIN SEQUENCE (hCP43771) |
| | CANCER GENE: mCG18584/hCG20056 |
| 823. | MOUSE GENOMIC SEQUENCE (mCG18584) |
| 824. | MOUSE mRNA SEQUENCE (mCT14726) |
| 825. | MOUSE PROTEIN SEQUENCE (mCP7085) |
| 826. | HUMAN GENOMIC SEQUENCE (hCG20056) |
| 827. | HUMAN mRNA SEQUENCE (hCT11129) |
| 828. | HUMAN PROTEIN SEQUENCE (hCP38832) |
| | CANCER GENE: mCG18590/hCG21253 |
| 829. | MOUSE GENOMIC SEQUENCE (mCG18590) |
| 830. | MOUSE mRNA SEQUENCE (mCT14732) |
| 831. | MOUSE PROTEIN SEQUENCE (mCP7070) |
| 832. | HUMAN GENOMIC SEQUENCE (hCG21253) |
| 833. | HUMAN mRNA SEQUENCE (hCT12340) |
| 834. | HUMAN PROTEIN SEQUENCE (hCP38816) |
| | CANCER GENE: mCG18632/hCG19781 |
| 835. | MOUSE GENOMIC SEQUENCE (mCG18632) |
| 836. | MOUSE mRNA SEQUENCE (mCT14990) |
| 837. | MOUSE PROTEIN SEQUENCE (mCP5574) |
| 838. | HUMAN GENOMIC SEQUENCE (hCG19781) |
| 839. | HUMAN mRNA SEQUENCE (hCT10853) |
| 840. | HUMAN PROTEIN SEQUENCE (hCP37496) |
| | CANCER GENE: mCG1867/hCG41365 |
| 841. | MOUSE GENOMIC SEQUENCE (mCG1867) |
| 842. | MOUSE mRNA SEQUENCE (mCT8103) |
| 843. | MOUSE PROTEIN SEQUENCE (mCP8903) |
| 844. | HUMAN GENOMIC SEQUENCE (hCG41365) |
| 845. | HUMAN mRNA SEQUENCE (hCT1952548) |
| 846. | HUMAN PROTEIN SEQUENCE (hCP1751079) |
| | CANCER GENE: mCG18746/hCG1780827 |
| 847. | MOUSE GENOMIC SEQUENCE (mCG18746) |
| 848. | MOUSE mRNA SEQUENCE (mCT15145) |
| 849. | MOUSE PROTEIN SEQUENCE (mCP19420) |
| 850. | HUMAN GENOMIC SEQUENCE (hCG1780827) |
| 851. | HUMAN mRNA SEQUENCE (hCT1819672) |
| 852. | HUMAN PROTEIN SEQUENCE (hCP1699110) |

TABLE 2-continued

IDENTIFICATION OF SEQUENCES

| SEQ ID NOS. | SEQUENCES |
|---|---|
| | CANCER GENE: mCG18928/hCG41574 |
| 853. | MOUSE GENOMIC SEQUENCE (mCG18928) |
| 854. | MOUSE mRNA SEQUENCE (mCT16310) |
| 855. | MOUSE PROTEIN SEQUENCE (mCP9514) |
| 856. | HUMAN GENOMIC SEQUENCE (hCG41574) |
| 857. | HUMAN mRNA SEQUENCE (hCT32846) |
| 858. | HUMAN PROTEIN SEQUENCE (hCP51438) |
| | CANCER GENE: mCG19018/hCG27894 |
| 859. | MOUSE GENOMIC SEQUENCE (mCG19018) |
| 860. | MOUSE mRNA SEQUENCE (mCT16908) |
| 861. | MOUSE PROTEIN SEQUENCE (mCP1516) |
| 862. | HUMAN GENOMIC SEQUENCE (hCG27894) |
| 863. | HUMAN mRNA SEQUENCE (hCT19037) |
| 864. | HUMAN PROTEIN SEQUENCE (hCP43456) |
| | CANCER GENE: mCG19046/hCG40314 |
| 865. | MOUSE GENOMIC SEQUENCE (mCG19046) |
| 866. | MOUSE mRNA SEQUENCE (mCT16990) |
| 867. | MOUSE PROTEIN SEQUENCE (mCP16883) |
| 868. | HUMAN GENOMIC SEQUENCE (hCG40314) |
| 869. | HUMAN mRNA SEQUENCE (hCT31569) |
| 870. | HUMAN PROTEIN SEQUENCE (hCP50078) |
| | CANCER GENE: mCG19072/hCG15138 |
| 871. | MOUSE GENOMIC SEQUENCE (mCG19072) |
| 872. | MOUSE mRNA SEQUENCE (mCT17004) |
| 873. | MOUSE PROTEIN SEQUENCE (mCP8457) |
| 874. | HUMAN GENOMIC SEQUENCE (hCG15138) |
| 875. | HUMAN mRNA SEQUENCE (hCT6159) |
| 876. | HUMAN PROTEIN SEQUENCE (hCP33301) |
| | CANCER GENE: mCG19106/hCG16291 |
| 877. | MOUSE GENOMIC SEQUENCE (mCG19106) |
| 878. | MOUSE mRNA SEQUENCE (mCT18122) |
| 879. | MOUSE PROTEIN SEQUENCE (mCP2823) |
| 880. | HUMAN GENOMIC SEQUENCE (hCG16291) |
| 881. | HUMAN mRNA SEQUENCE (hCT7327) |
| 882. | HUMAN PROTEIN SEQUENCE (hCP35582) |
| | CANCER GENE: mCG19156/hCG27607 |
| 883. | MOUSE GENOMIC SEQUENCE (mCG19156) |
| 884. | MOUSE mRNA SEQUENCE (mCT17748) |
| 885. | MOUSE PROTEIN SEQUENCE (mCP14606) |
| 886. | HUMAN GENOMIC SEQUENCE (hCG27607) |
| 887. | HUMAN mRNA SEQUENCE (hCT1952652) |
| 888. | HUMAN PROTEIN SEQUENCE (hCP1763679) |
| | CANCER GENE: mCG19208/hCG20766 |
| 889. | MOUSE GENOMIC SEQUENCE (mCG19208) |
| 890. | MOUSE mRNA SEQUENCE (mCT17801) |
| 891. | MOUSE PROTEIN SEQUENCE (mCP3161) |
| 892. | HUMAN GENOMIC SEQUENCE (hCG20766) |
| 893. | HUMAN mRNA SEQUENCE (hCT11846) |
| 894. | HUMAN PROTEIN SEQUENCE (hCP39739) |
| | CANCER GENE: mCG19209/hCG22243 |
| 895. | MOUSE GENOMIC SEQUENCE (mCG19209) |
| 896. | MOUSE mRNA SEQUENCE (mCT17802) |
| 897. | MOUSE PROTEIN SEQUENCE (mCP3189) |
| 898. | HUMAN GENOMIC SEQUENCE (hCG22243) |
| 899. | HUMAN mRNA SEQUENCE (hCT13336) |
| 900. | HUMAN PROTEIN SEQUENCE (hCP39738) |
| | CANCER GENE: mCG19250/hCG27772 |
| 901. | MOUSE GENOMIC SEQUENCE (mCG19250) |
| 902. | MOUSE mRNA SEQUENCE (mCT18452) |
| 903. | MOUSE PROTEIN SEQUENCE (mCP22058) |
| 904. | HUMAN GENOMIC SEQUENCE (hCG27772) |
| 905. | HUMAN mRNA SEQUENCE (hCT18914) |
| 906. | HUMAN PROTEIN SEQUENCE (hCP43333) |

TABLE 2-continued

IDENTIFICATION OF SEQUENCES

| SEQ ID NOS. | SEQUENCES |
|---|---|
| | CANCER GENE: mCG19287/hCG1748307 |
| 907. | MOUSE GENOMIC SEQUENCE (mCG19287) |
| 908. | MOUSE mRNA SEQUENCE (mCT18854) |
| 909. | MOUSE PROTEIN SEQUENCE (mCP22301) |
| 910. | HUMAN GENOMIC SEQUENCE (hCG1748307) |
| 911. | HUMAN mRNA SEQUENCE (hCT1786681) |
| 912. | HUMAN PROTEIN SEQUENCE (hCP1732005) |
| | CANCER GENE: mCG19337/hCG28784 |
| 913. | MOUSE GENOMIC SEQUENCE (mCG19337) |
| 914. | MOUSE mRNA SEQUENCE (mCT18618) |
| 915. | MOUSE PROTEIN SEQUENCE (mCP15257) |
| 916. | HUMAN GENOMIC SEQUENCE (hCG28784) |
| 917. | HUMAN mRNA SEQUENCE (hCT19939) |
| 918. | HUMAN PROTEIN SEQUENCE (hCP44152) |
| | CANCER GENE: mCG19401/hCG38450 |
| 919. | MOUSE GENOMIC SEQUENCE (mCG19401) |
| 920. | MOUSE mRNA SEQUENCE (mCT18996) |
| 921. | MOUSE PROTEIN SEQUENCE (mCP17117) |
| 922. | HUMAN GENOMIC SEQUENCE (hCG38450) |
| 923. | HUMAN mRNA SEQUENCE (hCT29693) |
| 924. | HUMAN PROTEIN SEQUENCE (hCP48354) |
| | CANCER GENE: mCG1941/hCG40854 |
| 925. | MOUSE GENOMIC SEQUENCE (mCG1941) |
| 926. | MOUSE mRNA SEQUENCE (mCT8323) |
| 927. | MOUSE PROTEIN SEQUENCE (mCP9809) |
| 928. | HUMAN GENOMIC SEQUENCE (hCG40854) |
| 929. | HUMAN mRNA SEQUENCE (hCT32121) |
| 930. | HUMAN PROTEIN SEQUENCE (hCP50646) |
| | CANCER GENE: mCG1961/hCG40844 |
| 931. | MOUSE GENOMIC SEQUENCE (mCG1961) |
| 932. | MOUSE mRNA SEQUENCE (mCT8343) |
| 933. | MOUSE PROTEIN SEQUENCE (mCP9806) |
| 934. | HUMAN GENOMIC SEQUENCE (hCG40844) |
| 935. | HUMAN mRNA SEQUENCE (hCT1686451) |
| 936. | HUMAN PROTEIN SEQUENCE (hCP1689977) |
| | CANCER GENE: mCG19789/hCG24313 |
| 937. | MOUSE GENOMIC SEQUENCE (mCG19789) |
| 938. | MOUSE mRNA SEQUENCE (mCT22538) |
| 939. | MOUSE PROTEIN SEQUENCE (mCP9116) |
| 940. | HUMAN GENOMIC SEQUENCE (hCG24313) |
| 941. | HUMAN mRNA SEQUENCE (hCT15427) |
| 942. | HUMAN PROTEIN SEQUENCE (hCP41584) |
| | CANCER GENE: mCG1982/hCG24071 |
| 943. | MOUSE GENOMIC SEQUENCE (mCG1982) |
| 944. | MOUSE mRNA SEQUENCE (mCT1158) |
| 945. | MOUSE PROTEIN SEQUENCE (mCP5141) |
| 946. | HUMAN GENOMIC SEQUENCE (hCG24071) |
| 947. | HUMAN mRNA SEQUENCE (hCT15185) |
| 948. | HUMAN PROTEIN SEQUENCE (hCP41406) |
| | CANCER GENE: mCG19885/hCG26017 |
| 949. | MOUSE GENOMIC SEQUENCE (mCG19885) |
| 950. | MOUSE mRNA SEQUENCE (mCT17661) |
| 951. | MOUSE PROTEIN SEQUENCE (mCP14589) |
| 952. | HUMAN GENOMIC SEQUENCE (hCG26017) |
| 953. | HUMAN mRNA SEQUENCE (hCTI7145) |
| 954. | HUMAN PROTEIN SEQUENCE (hCP42562) |
| | CANCER GENE: mCG19929/hCG40063 |
| 955. | MOUSE GENOMIC SEQUENCE (mCG19929) |
| 956. | MOUSE mRNA SEQUENCE (mCT17877) |
| 957. | MOUSE PROTEIN SEQUENCE (mCP23084) |
| 958. | HUMAN GENOMIC SEQUENCE (hCG40063) |
| 959. | HUMAN mRNA SEQUENCE (hCT1823066) |
| 960. | HUMAN PROTEIN SEQUENCE (hCP1707933) |

TABLE 2-continued

IDENTIFICATION OF SEQUENCES

| SEQ ID NOS. | SEQUENCES |
|---|---|
| | CANCER GENE: mCG19993/hCG25375 |
| 961. | MOUSE GENOMIC SEQUENCE (mCG19993) |
| 962. | MOUSE mRNA SEQUENCE (mCT18155) |
| 963. | MOUSE PROTEIN SEQUENCE (mCP14222) |
| 964. | HUMAN GENOMIC SEQUENCE (hCG25375) |
| 965. | HUMAN mRNA SEQUENCE (hCT16500) |
| 966. | HUMAN PROTEIN SEQUENCE (hCP42262) |
| | CANCER GENE: mCG20206/hCG27935 |
| 967. | MOUSE GENOMIC SEQUENCE (mCG20206) |
| 968. | MOUSE mRNA SEQUENCE (mCT19895) |
| 969. | MOUSE PROTEIN SEQUENCE (mCP23593) |
| 970. | HUMAN GENOMIC SEQUENCE (hCG27935) |
| 971. | HUMAN mRNA SEQUENCE (hCT19078) |
| 972. | HUMAN PROTEIN SEQUENCE (hCP43550) |
| | CANCER GENE: mCG20340/hCG18066 |
| 973. | MOUSE GENOMIC SEQUENCE (mCG20340) |
| 974. | MOUSE mRNA SEQUENCE (mCT20192) |
| 975. | MOUSE PROTEIN SEQUENCE (mCP17648) |
| 976. | HUMAN GENOMIC SEQUENCE (hCG18066) |
| 977. | HUMAN mRNA SEQUENCE (hCT9121) |
| 978. | HUMAN PROTEIN SEQUENCE (hCP35943) |
| | CANCER GENE: mCG20392/hCG41562 |
| 979. | MOUSE GENOMIC SEQUENCE (mCG20392) |
| 980. | MOUSE mRNA SEQUENCE (mCT20937) |
| 981. | MOUSE PROTEIN SEQUENCE (mCP13103) |
| 982. | HUMAN GENOMIC SEQUENCE (hCG41562) |
| 983. | HUMAN mRNA SEQUENCE (hCT32834) |
| 984. | HUMAN PROTEIN SEQUENCE (hCP51417) |
| | CANCER GENE: mCG20408/hCG15769 |
| 985. | MOUSE GENOMIC SEQUENCE (mCG20408) |
| 986. | MOUSE mRNA SEQUENCE (mCT21077) |
| 987. | MOUSE PROTEIN SEQUENCE (mCP23696) |
| 988. | HUMAN GENOMIC SEQUENCE (hCG15769) |
| 989. | HUMAN mRNA SEQUENCE (hCT6798) |
| 990. | HUMAN PROTEIN SEQUENCE (hCP34326) |
| | CANCER GENE: mCG20501/hCG16575 |
| 991. | MOUSE GENOMIC SEQUENCE (mCG20501) |
| 992. | MOUSE mRNA SEQUENCE (mCT22294) |
| 993. | MOUSE PROTEIN SEQUENCE (mCP23389) |
| 994. | HUMAN GENOMIC SEQUENCE (hCG16575) |
| 995. | HUMAN mRNA SEQUENCE (hCT7612) |
| 996. | HUMAN PROTEIN SEQUENCE (hCP34651) |
| | CANCER GENE: mCG20543/hCG17361 |
| 997. | MOUSE GENOMIC SEQUENCE (mCG20543) |
| 998. | MOUSE mRNA SEQUENCE (mCT21892) |
| 999. | MOUSE PROTEIN SEQUENCE (mCP10453) |
| 1000. | HUMAN GENOMIC SEQUENCE (hCG17361) |
| 1001. | HUMAN mRNA SEQUENCE (hCT8411) |
| 1002. | HUMAN PROTEIN SEQUENCE (hCP34192) |
| | CANCER GENE: mCG20544/hCG22647 |
| 1003. | MOUSE GENOMIC SEQUENCE (mCG20544) |
| 1004. | MOUSE mRNA SEQUENCE (mCT21893) |
| 1005. | MOUSE PROTEIN SEQUENCE (mCP10423) |
| 1006. | HUMAN GENOMIC SEQUENCE (hCG22647) |
| 1007. | HUMAN mRNA SEQUENCE (hCT13744) |
| 1008. | HUMAN PROTEIN SEQUENCE (hCP40084) |
| | CANCER GENE: mCG20549/hCG17357 |
| 1009. | MOUSE GENOMIC SEQUENCE (mCG20549) |
| 1010. | MOUSE mRNA SEQUENCE (mCT21898) |
| 1011. | MOUSE PROTEIN SEQUENCE (mCP10442) |
| 1012. | HUMAN GENOMIC SEQUENCE (hCG17357) |
| 1013. | HUMAN mRNA SEQUENCE (hCT8407) |
| 1014. | HUMAN PROTEIN SEQUENCE (hCP34188) |
| | CANCER GENE: mCG20599/hCG40952 |
| 1015. | MOUSE GENOMIC SEQUENCE (mCG20599) |
| 1016. | MOUSE mRNA SEQUENCE (mCT22020) |
| 1017. | MOUSE PROTEIN SEQUENCE (mCP9456) |
| 1018. | HUMAN GENOMIC SEQUENCE (hCG40952) |
| 1019. | HUMAN mRNA SEQUENCE (hCT32220) |
| 1020. | HUMAN PROTEIN SEQUENCE (hCP50752) |
| | CANCER GENE: mCG20647/hCG37125 |
| 1021. | MOUSE GENOMIC SEQUENCE (mCG20647) |
| 1022. | MOUSE mRNA SEQUENCE (mCT22233) |
| 1023. | MOUSE PROTEIN SEQUENCE (mCP5967) |
| 1024. | HUMAN GENOMIC SEQUENCE (hCG37125) |
| 1025. | HUMAN mRNA SEQUENCE (hCT28355) |
| 1026. | HUMAN PROTEIN SEQUENCE (hCP47821) |
| | CANCER GENE: mCG20650/hCG38101 |
| 1027. | MOUSE GENOMIC SEQUENCE (mCG20650) |
| 1028. | MOUSE mRNA SEQUENCE (mCT22578) |
| 1029. | MOUSE PROTEIN SEQUENCE (mCP5887) |
| 1030. | HUMAN GENOMIC SEQUENCE (hCG38101) |
| 1031. | HUMAN mRNA SEQUENCE (hCT29338) |
| 1032. | HUMAN PROTEIN SEQUENCE (hCP48033) |
| | CANCER GENE: mCG21092/hCG16326 |
| 1033. | MOUSE GENOMIC SEQUENCE (mCG21092) |
| 1034. | MOUSE mRNA SEQUENCE (mCT20021) |
| 1035. | MOUSE PROTEIN SEQUENCE (mCP14767) |
| 1036. | HUMAN GENOMIC SEQUENCE (hCG16326) |
| 1037. | HUMAN mRNA SEQUENCE (hCT7362) |
| 1038. | HUMAN PROTEIN SEQUENCE (hCP34078) |
| | CANCER GENE: mCG21183/hCG32701 |
| 1039. | MOUSE GENOMIC SEQUENCE (mCG21183) |
| 1040. | MOUSE mRNA SEQUENCE (mCT21009) |
| 1041. | MOUSE PROTEIN SEQUENCE (mCP22191) |
| 1042. | HUMAN GENOMIC SEQUENCE (hCG32701) |
| 1043. | HUMAN mRNA SEQUENCE (hCT23891) |
| 1044. | HUMAN PROTEIN SEQUENCE (hCP45986) |
| | CANCER GENE: mCG21200/hCG17049 |
| 1045. | MOUSE GENOMIC SEQUENCE (mCG21200) |
| 1046. | MOUSE mRNA SEQUENCE (mCT20361) |
| 1047. | MOUSE PROTEIN SEQUENCE (mCP16931) |
| 1048. | HUMAN GENOMIC SEQUENCE (hCG17049) |
| 1049. | HUMAN mRNA SEQUENCE (hCT8096) |
| 1050. | HUMAN PROTEIN SEQUENCE (hCP34372) |
| | CANCER GENE: mCG21319/hCG39866 |
| 1051. | MOUSE GENOMIC SEQUENCE (mCG21319) |
| 1052. | MOUSE mRNA SEQUENCE (mCT21706) |
| 1053. | MOUSE PROTEIN SEQUENCE (mCP9747) |
| 1054. | HUMAN GENOMIC SEQUENCE (hCG39866) |
| 1055. | HUMAN mRNA SEQUENCE (hCT31118) |
| 1056. | HUMAN PROTEIN SEQUENCE (hCP49649) |
| | CANCER GENE: mCG2140/hCG1723924 |
| 1057. | MOUSE GENOMIC SEQUENCE (mCG2140) |
| 1058. | MOUSE mRNA SEQUENCE (mCT8480) |
| 1059. | MOUSE PROTEIN SEQUENCE (mCP18923) |
| 1060. | HUMAN GENOMIC SEQUENCE (hCG1723924) |
| 1061. | HUMAN mRNA SEQUENCE (hCT1850193) |
| 1062. | HUMAN PROTEIN SEQUENCE (hCP1720717) |
| | CANCER GENE: mCG21411/hCG15095 |
| 1063. | MOUSE GENOMIC SEQUENCE (mCG21411) |
| 1064. | MOUSE mRNA SEQUENCE (mCT21965) |
| 1065. | MOUSE PROTEIN SEQUENCE (mCP20781) |
| 1066. | HUMAN GENOMIC SEQUENCE (hCG15095) |
| 1067. | HUMAN mRNA SEQUENCE (hCT6116) |
| 1068. | HUMAN PROTEIN SEQUENCE (hCP34831) |

TABLE 2-continued

IDENTIFICATION OF SEQUENCES

| SEQ ID NOS. | SEQUENCES |
|---|---|
| | CANCER GENE: mCG21419/hCG15331 |
| 1069. | MOUSE GENOMIC SEQUENCE (mCG21419) |
| 1070. | MOUSE mRNA SEQUENCE (mCT21971) |
| 1071. | MOUSE PROTEIN SEQUENCE (mCP20826) |
| 1072. | HUMAN GENOMIC SEQUENCE (hCG15331) |
| 1073. | HUMAN mRNA SEQUENCE (hCT6353) |
| 1074. | HUMAN PROTEIN SEQUENCE (hCP35780) |
| | CANCER GENE: mCG21446/hCG14759 |
| 1075. | MOUSE GENOMIC SEQUENCE (mCG21446) |
| 1076. | MOUSE mRNA SEQUENCE (mCT22143) |
| 1077. | MOUSE PROTEIN SEQUENCE (mCP16097) |
| 1078. | HUMAN GENOMIC SEQUENCE (hCG14759) |
| 1079. | HUMAN mRNA SEQUENCE (hCT5780) |
| 1080. | HUMAN PROTEIN SEQUENCE (hCP33254) |
| | CANCER GENE: mCG21498/hCG38237 |
| 1081. | MOUSE GENOMIC SEQUENCE (mCG21498) |
| 1082. | MOUSE mRNA SEQUENCE (mCT15384) |
| 1083. | MOUSE PROTEIN SEQUENCE (mCP11030) |
| 1084. | HUMAN GENOMIC SEQUENCE (hCG38237) |
| 1085. | HUMAN mRNA SEQUENCE (hCT29477) |
| 1086. | HUMAN PROTEIN SEQUENCE (hCP48130) |
| | CANCER GENE: mCG21659/hCG18576 |
| 1087. | MOUSE GENOMIC SEQUENCE (mCG21659) |
| 1088. | MOUSE mRNA SEQUENCE (mCT19951) |
| 1089. | MOUSE PROTEIN SEQUENCE (mCP15815) |
| 1090. | HUMAN GENOMIC SEQUENCE (hCG18576) |
| 1091. | HUMAN mRNA SEQUENCE (hCT9635) |
| 1092. | HUMAN PROTEIN SEQUENCE (hCP36377) |
| | CANCER GENE: mCG21733/hCG40245 |
| 1093. | MOUSE GENOMIC SEQUENCE (mCG21733) |
| 1094. | MOUSE mRNA SEQUENCE (mCT20681) |
| 1095. | MOUSE PROTEIN SEQUENCE (mCP19793) |
| 1096. | HUMAN GENOMIC SEQUENCE (hCG40245) |
| 1097. | HUMAN mRNA SEQUENCE (hCT31498) |
| 1098. | HUMAN PROTEIN SEQUENCE (hCP50028) |
| | CANCER GENE: mCG21872/hCG17143 |
| 1099. | MOUSE GENOMIC SEQUENCE (mCG21872) |
| 1100. | MOUSE mRNA SEQUENCE (mCT21839) |
| 1101. | MOUSE PROTEIN SEQUENCE (mCP18614) |
| 1102. | HUMAN GENOMIC SEQUENCE (hCG17143) |
| 1103. | HUMAN mRNA SEQUENCE (hCT8191) |
| 1104. | HUMAN PROTEIN SEQUENCE (hCP34482) |
| | CANCER GENE: mCG21902/hCG30014 |
| 1105. | MOUSE GENOMIC SEQUENCE (mCG21902) |
| 1106. | MOUSE mRNA SEQUENCE (mCT22359) |
| 1107. | MOUSE PROTEIN SEQUENCE (mCP23428) |
| 1108. | HUMAN GENOMIC SEQUENCE (hCG30014) |
| 1109. | HUMAN mRNA SEQUENCE (hCT21181) |
| 1110. | HUMAN PROTEIN SEQUENCE (hCP44697) |
| | CANCER GENE: mCG22056/hCG40203 |
| 1111. | MOUSE GENOMIC SEQUENCE (mCG22056) |
| 1112. | MOUSE mRNA SEQUENCE (mCT22792) |
| 1113. | MOUSE PROTEIN SEQUENCE (mCP13158) |
| 1114. | HUMAN GENOMIC SEQUENCE (hCG40203) |
| 1115. | HUMAN mRNA SEQUENCE (hCT31457) |
| 1116. | HUMAN PROTEIN SEQUENCE (hCP50001) |
| | CANCER GENE: mCG22132/hCG15373 |
| 1117. | MOUSE GENOMIC SEQUENCE (mCG22132) |
| 1118. | MOUSE mRNA SEQUENCE (mCT23888) |
| 1119. | MOUSE PROTEIN SEQUENCE (mCP7739) |
| 1120. | HUMAN GENOMIC SEQUENCE (hCG15373) |
| 1121. | HUMAN mRNA SEQUENCE (hCT6395) |
| 1122. | HUMAN PROTEIN SEQUENCE (hCP35254) |
| | CANCER GENE: mCG2215/hCG401221 |
| 1123. | MOUSE GENOMIC SEQUENCE (mCG2215) |
| 1124. | MOUSE mRNA SEQUENCE (mCT1626) |
| 1125. | MOUSE PROTEIN SEQUENCE (mCP17313) |
| 1126. | HUMAN GENOMIC SEQUENCE (hCG401221) |
| 1127. | HUMAN mRNA SEQUENCE (hCT401225) |
| 1128. | HUMAN PROTEIN SEQUENCE (hCP801144) |
| | CANCER GENE: mCG22161/hCG1781402 |
| 1129. | MOUSE GENOMIC SEQUENCE (mCG22161) |
| 1130. | MOUSE mRNA SEQUENCE (mCT20255) |
| 1131. | MOUSE PROTEIN SEQUENCE (mCP2942) |
| 1132. | HUMAN GENOMIC SEQUENCE (hCG1781402) |
| 1133. | HUMAN mRNA SEQUENCE (hCT1820269) |
| 1134. | HUMAN PROTEIN SEQUENCE (hCP1718580) |
| | CANCER GENE: mCG22171/hCG37949 |
| 1135. | MOUSE GENOMIC SEQUENCE (mCG22171) |
| 1136. | MOUSE mRNA SEQUENCE (mCT19935) |
| 1137. | MOUSE PROTEIN SEQUENCE (mCP21795) |
| 1138. | HUMAN GENOMIC SEQUENCE (hCG37949) |
| 1139. | HUMAN mRNA SEQUENCE (hCT29185) |
| 1140. | HUMAN PROTEIN SEQUENCE (hCP47881) |
| | CANCER GENE: mCG22175/hCG1735628 |
| 1141. | MOUSE GENOMIC SEQUENCE (mCG22175) |
| 1142. | MOUSE mRNA SEQUENCE (mCT20599) |
| 1143. | MOUSE PROTEIN SEQUENCE (mCP21804) |
| 1144. | HUMAN GENOMIC SEQUENCE (hCG1735628) |
| 1145. | HUMAN mRNA SEQUENCE (hCT1773627) |
| 1146. | HUMAN PROTEIN SEQUENCE (hCP1730899) |
| | CANCER GENE: mCG22205/hCG16145 |
| 1147. | MOUSE GENOMIC SEQUENCE (mCG22205) |
| 1148. | MOUSE mRNA SEQUENCE (mCT20638) |
| 1149. | MOUSE PROTEIN SEQUENCE (mCP2261) |
| 1150. | HUMAN GENOMIC SEQUENCE (hCG16145) |
| 1151. | HUMAN mRNA SEQUENCE (hCT5796) |
| 1152. | HUMAN PROTEIN SEQUENCE (hCP35596) |
| | CANCER GENE: mCG22245/hCG15467 |
| 1153. | MOUSE GENOMIC SEQUENCE (mCG22245) |
| 1154. | MOUSE mRNA SEQUENCE (mCT21201) |
| 1155. | MOUSE PROTEIN SEQUENCE (mCP17263) |
| 1156. | HUMAN GENOMIC SEQUENCE (hCG15467) |
| 1157. | HUMAN mRNA SEQUENCE (hCT1952272) |
| 1158. | HUMAN PROTEIN SEQUENCE (hCP1751324) |
| | CANCER GENE: mCG22259/hCG27692 |
| 1159. | MOUSE GENOMIC SEQUENCE (mCG22259) |
| 1160. | MOUSE mRNA SEQUENCE (mCT20705) |
| 1161. | MOUSE PROTEIN SEQUENCE (mCP14816) |
| 1162. | HUMAN GENOMIC SEQUENCE (hCG27692) |
| 1163. | HUMAN mRNA SEQUENCE (hCT18834) |
| 1164. | HUMAN PROTEIN SEQUENCE (hCP43255) |
| | CANCER GENE: mCG22352/hCG19724 |
| 1165. | MOUSE GENOMIC SEQUENCE (mCG22352) |
| 1166. | MOUSE mRNA SEQUENCE (mCT21719) |
| 1167. | MOUSE PROTEIN SEQUENCE (mCP3415) |
| 1168. | HUMAN GENOMIC SEQUENCE (hCG19724) |
| 1169. | HUMAN mRNA SEQUENCE (hCT10796) |
| 1170. | HUMAN PROTEIN SEQUENCE (hCP38730) |
| | CANCER GENE: mCG22397/hCG21624 |
| 1171. | MOUSE GENOMIC SEQUENCE (mCG22397) |
| 1172. | MOUSE mRNA SEQUENCE (mCT22492) |
| 1173. | MOUSE PROTEIN SEQUENCE (mCP10498) |
| 1174. | HUMAN GENOMIC SEQUENCE (hCG21624) |
| 1175. | HUMAN mRNA SEQUENCE (hCT1686293) |
| 1176. | HUMAN PROTEIN SEQUENCE (hCP1690086) |

TABLE 2-continued

IDENTIFICATION OF SEQUENCES

| SEQ ID NOS. | SEQUENCES |
|---|---|
| | CANCER GENE: mCG22413/hCG21734 |
| 1177. | MOUSE GENOMIC SEQUENCE (mCG22413) |
| 1178. | MOUSE mRNA SEQUENCE (mCT22509) |
| 1179. | MOUSE PROTEIN SEQUENCE (mCP10494) |
| 1180. | HUMAN GENOMIC SEQUENCE (hCG21734) |
| 1181. | HUMAN mRNA SEQUENCE (hCT12827) |
| 1182. | HUMAN PROTEIN SEQUENCE (hCP39228) |
| | CANCER GENE: mCG22464/hCG17117 |
| 1183. | MOUSE GENOMIC SEQUENCE (mCG22464) |
| 1184. | MOUSE mRNA SEQUENCE (mCT22319) |
| 1185. | MOUSE PROTEIN SEQUENCE (mCP11320) |
| 1186. | HUMAN GENOMIC SEQUENCE (hCG17117) |
| 1187. | HUMAN mRNA SEQUENCE (hCT1953974) |
| 1188. | HUMAN PROTEIN SEQUENCE (hCP1765761) |
| | CANCER GENE: mCG22467/hCG17195 |
| 1189. | MOUSE GENOMIC SEQUENCE (mCG22467) |
| 1190. | MOUSE mRNA SEQUENCE (mCT22321) |
| 1191. | MOUSE PROTEIN SEQUENCE (mCP11315) |
| 1192. | HUMAN GENOMIC SEQUENCE (hCG17195) |
| 1193. | HUMAN mRNA SEQUENCE (hCT1955454) |
| 1194. | HUMAN PROTEIN SEQUENCE (hCP1765759) |
| | CANCER GENE: mCG22474/hCG17936 |
| 1195. | MOUSE GENOMIC SEQUENCE (mCG22474) |
| 1196. | MOUSE mRNA SEQUENCE (mCT22330) |
| 1197. | MOUSE PROTEIN SEQUENCE (mCP11335) |
| 1198. | HUMAN GENOMIC SEQUENCE (hCG17936) |
| 1199. | HUMAN mRNA SEQUENCE (hCT8990) |
| 1200. | HUMAN PROTEIN SEQUENCE (hCP33893) |
| | CANCER GENE: mCG22518/hCG38672 |
| 1201. | MOUSE GENOMIC SEQUENCE (mCG22518) |
| 1202. | MOUSE mRNA SEQUENCE (mCT22818) |
| 1203. | MOUSE PROTEIN SEQUENCE (mCP15759) |
| 1204. | HUMAN GENOMIC SEQUENCE (hCG38672) |
| 1205. | HUMAN mRNA SEQUENCE (hCT29916) |
| 1206. | HUMAN PROTEIN SEQUENCE (hCP48498) |
| | CANCER GENE: mCG22537/hCG1747156 |
| 1207. | MOUSE GENOMIC SEQUENCE (mCG22537) |
| 1208. | MOUSE mRNA SEQUENCE (mCT22933) |
| 1209. | MOUSE PROTEIN SEQUENCE (mCP10415) |
| 1210. | HUMAN GENOMIC SEQUENCE (hCG1747156) |
| 1211. | HUMAN mRNA SEQUENCE (hCT1785481) |
| 1212. | HUMAN PROTEIN SEQUENCE (hCP1738978) |
| | CANCER GENE: mCG2260/hCG23472 |
| 1213. | MOUSE GENOMIC SEQUENCE (mCG2260) |
| 1214. | MOUSE mRNA SEQUENCE (mCT1669) |
| 1215. | MOUSE PROTEIN SEQUENCE (mCP13569) |
| 1216. | HUMAN GENOMIC SEQUENCE (hCG23472) |
| 1217. | HUMAN mRNA SEQUENCE (hCT1823706) |
| 1218. | HUMAN PROTEIN SEQUENCE (hCP1721278) |
| | CANCER GENE: mCG22656/hCG20930 |
| 1219. | MOUSE GENOMIC SEQUENCE (mCG22656) |
| 1220. | MOUSE mRNA SEQUENCE (mCT21511) |
| 1221. | MOUSE PROTEIN SEQUENCE (mCP10653) |
| 1222. | HUMAN GENOMIC SEQUENCE (hCG20930) |
| 1223. | HUMAN mRNA SEQUENCE (hCT12011) |
| 1224. | HUMAN PROTEIN SEQUENCE (hCP38543) |
| | CANCER GENE: mCG22686/hCG37091 |
| 1225. | MOUSE GENOMIC SEQUENCE (mCG22686) |
| 1226. | MOUSE mRNA SEQUENCE (mCT21599) |
| 1227. | MOUSE PROTEIN SEQUENCE (mCP21078) |
| 1228. | HUMAN GENOMIC SEQUENCE (hCG37091) |
| 1229. | HUMAN mRNA SEQUENCE (hCT28321) |
| 1230. | HUMAN PROTEIN SEQUENCE (hCP47795) |
| | CANCER GENE: mCG22753/hCG20786 |
| 1231. | MOUSE GENOMIC SEQUENCE (mCG22753) |
| 1232. | MOUSE mRNA SEQUENCE (mCT23686) |
| 1233. | MOUSE PROTEIN SEQUENCE (mCP4643) |
| 1234. | HUMAN GENOMIC SEQUENCE (hCG20786) |
| 1235. | HUMAN mRNA SEQUENCE (hCT11866) |
| 1236. | HUMAN PROTEIN SEQUENCE (hCP38416) |
| | CANCER GENE: mCG23380/hCG27276 |
| 1237. | MOUSE GENOMIC SEQUENCE (mCG23380) |
| 1238. | MOUSE mRNA SEQUENCE (mCT23205) |
| 1239. | MOUSE PROTEIN SEQUENCE (mCP1348) |
| 1240. | HUMAN GENOMIC SEQUENCE (hCG27276) |
| 1241. | HUMAN mRNA SEQUENCE (hCT18414) |
| 1242. | HUMAN PROTEIN SEQUENCE (hCP44262) |
| | CANCER GENE: mCG23443/hCG1737521 |
| 1243. | MOUSE GENOMIC SEQUENCE (mCG23443) |
| 1244. | MOUSE mRNA SEQUENCE (mCT23318) |
| 1245. | MOUSE PROTEIN SEQUENCE (mCP12949) |
| 1246. | HUMAN GENOMIC SEQUENCE (hCG1737521) |
| 1247. | HUMAN mRNA SEQUENCE (hCT1775561) |
| 1248. | HUMAN PROTEIN SEQUENCE (hCP1715933) |
| | CANCER GENE: mCG23445/hCG16206 |
| 1249. | MOUSE GENOMIC SEQUENCE (mCG23445) |
| 1250. | MOUSE mRNA SEQUENCE (mCT23312) |
| 1251. | MOUSE PROTEIN SEQUENCE (mCP22701) |
| 1252. | HUMAN GENOMIC SEQUENCE (hCG16206) |
| 1253. | HUMAN mRNA SEQUENCE (hCT7238) |
| 1254. | HUMAN PROTEIN SEQUENCE (hCP35274) |
| | CANCER GENE: mCG2395/hCG33029 |
| 1255. | MOUSE GENOMIC SEQUENCE (mCG2395) |
| 1256. | MOUSE mRNA SEQUENCE (mCT1612) |
| 1257. | MOUSE PROTEIN SEQUENCE (mCP22401) |
| 1258. | HUMAN GENOMIC SEQUENCE (hCG33029) |
| 1259. | HUMAN mRNA SEQUENCE (hCT24222) |
| 1260. | HUMAN PROTEIN SEQUENCE (hCP46383) |
| | CANCER GENE: mCG2435/hCG16501 |
| 1261. | MOUSE GENOMIC SEQUENCE (mCG2435) |
| 1262. | MOUSE mRNA SEQUENCE (mCT1434) |
| 1263. | MOUSE PROTEIN SEQUENCE (mCP23075) |
| 1264. | HUMAN GENOMIC SEQUENCE (hCG16501) |
| 1265. | HUMAN mRNA SEQUENCE (hCT7539) |
| 1266. | HUMAN PROTEIN SEQUENCE (hCP34596) |
| | CANCER GENE: mCG2468/hCG16728 |
| 1267. | MOUSE GENOMIC SEQUENCE (mCG2468) |
| 1268. | MOUSE mRNA SEQUENCE (mCT1547) |
| 1269. | MOUSE PROTEIN SEQUENCE (mCP15074) |
| 1270. | HUMAN GENOMIC SEQUENCE (hCG16728) |
| 1271. | HUMAN mRNA SEQUENCE (hCT7769) |
| 1272. | HUMAN PROTEIN SEQUENCE (hCP34634) |
| | CANCER GENE: mCG2479/hCG1780031 |
| 1273. | MOUSE GENOMIC SEQUENCE (mCG2479) |
| 1274. | MOUSE mRNA SEQUENCE (mCT1532) |
| 1275. | MOUSE PROTEIN SEQUENCE (mCP15071) |
| 1276. | HUMAN GENOMIC SEQUENCE (hCG1780031) |
| 1277. | HUMAN mRNA SEQUENCE (hCT1818854) |
| 1278. | HUMAN PROTEIN SEQUENCE (hCP1727062) |
| | CANCER GENE: mCG2484/hCG1788599 |
| 1279. | MOUSE GENOMIC SEQUENCE (mCG2484) |
| 1280. | MOUSE mRNA SEQUENCE (mCT1596) |
| 1281. | MOUSE PROTEIN SEQUENCE (mCP15131) |
| 1282. | HUMAN GENOMIC SEQUENCE (hCG1788599) |
| 1283. | HUMAN mRNA SEQUENCE (hCT1827788) |
| 1284. | HUMAN PROTEIN SEQUENCE (hCP1698554) |

TABLE 2-continued

IDENTIFICATION OF SEQUENCES

| SEQ ID NOS. | SEQUENCES |
|---|---|
| | CANCER GENE: mCG2509/hCG17286 |
| 1285. | MOUSE GENOMIC SEQUENCE (mCG2509) |
| 1286. | MOUSE mRNA SEQUENCE (mCT1337) |
| 1287. | MOUSE PROTEIN SEQUENCE (mCP15079) |
| 1288. | HUMAN GENOMIC SEQUENCE (hCG17286) |
| 1289. | HUMAN mRNA SEQUENCE (hCT8336) |
| 1290. | HUMAN PROTEIN SEQUENCE (hCP34736) |
| | CANCER GENE: mCG2574/hCG1784894 |
| 1291. | MOUSE GENOMIC SEQUENCE (mCG2574) |
| 1292. | MOUSE mRNA SEQUENCE (mCT1974) |
| 1293. | MOUSE PROTEIN SEQUENCE (mCP1949) |
| 1294. | HUMAN GENOMIC SEQUENCE (hCG1784894) |
| 1295. | HUMAN mRNA SEQUENCE (hCT1823882) |
| 1296. | HUMAN PROTEIN SEQUENCE (hCP1743768) |
| | CANCER GENE: mCG2609/hCG14997 |
| 1297. | MOUSE GENOMIC SEQUENCE (mCG2609) |
| 1298. | MOUSE mRNA SEQUENCE (mCT1719) |
| 1299. | MOUSE PROTEIN SEQUENCE (mCP10212) |
| 1300. | HUMAN GENOMIC SEQUENCE (hCG14997) |
| 1301. | HUMAN mRNA SEQUENCE (hCT6018) |
| 1302. | HUMAN PROTEIN SEQUENCE (hCP35459) |
| | CANCER GENE: mCG2622/hCG1747365 |
| 1303. | MOUSE GENOMIC SEQUENCE (mCG2622) |
| 1304. | MOUSE mRNA SEQUENCE (mCT1718) |
| 1305. | MOUSE PROTEIN SEQUENCE (mCP10161) |
| 1306. | HUMAN GENOMIC SEQUENCE (hCG1747365) |
| 1307. | HUMAN mRNA SEQUENCE (hCT1785697) |
| 1308. | HUMAN PROTEIN SEQUENCE (hCP1706674) |
| | CANCER GENE: mCG2706/hCG28763 |
| 1309. | MOUSE GENOMIC SEQUENCE (mCG2706) |
| 1310. | MOUSE mRNA SEQUENCE (mCT2181) |
| 1311. | MOUSE PROTEIN SEQUENCE (mCP15287) |
| 1312. | HUMAN GENOMIC SEQUENCE (hCG28763) |
| 1313. | HUMAN mRNA SEQUENCE (hCT19918) |
| 1314. | HUMAN PROTEIN SEQUENCE (hCP44127) |
| | CANCER GENE: mCG2708/hCG28766 |
| 1315. | MOUSE GENOMIC SEQUENCE (mCG2708) |
| 1316. | MOUSE mRNA SEQUENCE (mCT2183) |
| 1317. | MOUSE PROTEIN SEQUENCE (mCP15222) |
| 1318. | HUMAN GENOMIC SEQUENCE (hCG28766) |
| 1319. | HUMAN mRNA SEQUENCE (hCT19921) |
| 1320. | HUMAN PROTEIN SEQUENCE (hCP44130) |
| | CANCER GENE: mCG2727/hCG17889 |
| 1321. | MOUSE GENOMIC SEQUENCE (mCG2727) |
| 1322. | MOUSE mRNA SEQUENCE (mCT7005) |
| 1323. | MOUSE PROTEIN SEQUENCE (mCP17408) |
| 1324. | HUMAN GENOMIC SEQUENCE (hCG17889) |
| 1325. | HUMAN mRNA SEQUENCE (hCT1955643) |
| 1326. | HUMAN PROTEIN SEQUENCE (hCP1761482) |
| | CANCER GENE: mCG2740/hCG27644 |
| 1327. | MOUSE GENOMIC SEQUENCE (mCG2740) |
| 1328. | MOUSE mRNA SEQUENCE (mCT1844) |
| 1329. | MOUSE PROTEIN SEQUENCE (mCP15248) |
| 1330. | HUMAN GENOMIC SEQUENCE (hCG27644) |
| 1331. | HUMAN mRNA SEQUENCE (hCT18785) |
| 1332. | HUMAN PROTEIN SEQUENCE (hCP44293) |
| | CANCER GENE: mCG2943/hCG40040 |
| 1333. | MOUSE GENOMIC SEQUENCE (mCG2943) |
| 1334. | MOUSE mRNA SEQUENCE (mCT1378) |
| 1335. | MOUSE PROTEIN SEQUENCE (mCP11134) |
| 1336. | HUMAN GENOMIC SEQUENCE (hCG40040) |
| 1337. | HUMAN mRNA SEQUENCE (hCT31293) |
| 1338. | HUMAN PROTEIN SEQUENCE (hCP49803) |
| | CANCER GENE: mCG3043/hCG1738334 |
| 1339. | MOUSE GENOMIC SEQUENCE (mCG3043) |
| 1340. | MOUSE mRNA SEQUENCE (mCT2186) |
| 1341. | MOUSE PROTEIN SEQUENCE (mCP15235) |
| 1342. | HUMAN GENOMIC SEQUENCE (hCG1738334) |
| 1343. | HUMAN mRNA SEQUENCE (hCT1776398) |
| 1344. | HUMAN PROTEIN SEQUENCE (hCP1713151) |
| | CANCER GENE: mCG3264/hCG29513 |
| 1345. | MOUSE GENOMIC SEQUENCE (mCG3264) |
| 1346. | MOUSE mRNA SEQUENCE (mCT2390) |
| 1347. | MOUSE PROTEIN SEQUENCE (mCP10872) |
| 1348. | HUMAN GENOMIC SEQUENCE (hCG29513) |
| 1349. | HUMAN mRNA SEQUENCE (hCT20677) |
| 1350. | HUMAN PROTEIN SEQUENCE (hCP44507) |
| | CANCER GENE: mCG3413/hCG29916 |
| 1351. | MOUSE GENOMIC SEQUENCE (mCG3413) |
| 1352. | MOUSE mRNA SEQUENCE (mCT2539) |
| 1353. | MOUSE PROTEIN SEQUENCE (mCP7559) |
| 1354. | HUMAN GENOMIC SEQUENCE (hCG29916) |
| 1355. | HUMAN mRNA SEQUENCE (hCT1950711) |
| 1356. | HUMAN PROTEIN SEQUENCE (hCP1767168) |
| | CANCER GENE: mCG3601/hCG37990 |
| 1357. | MOUSE GENOMIC SEQUENCE (mCG3601) |
| 1358. | MOUSE mRNA SEQUENCE (mCT3067) |
| 1359. | MOUSE PROTEIN SEQUENCE (mCP1756) |
| 1360. | HUMAN GENOMIC SEQUENCE (hCG37990) |
| 1361. | HUMAN mRNA SEQUENCE (hCT1951562) |
| 1362. | HUMAN PROTEIN SEQUENCE (hCP1767307) |
| | CANCER GENE: mCG3698/hCG20145 |
| 1363. | MOUSE GENOMIC SEQUENCE (mCG3698) |
| 1364. | MOUSE mRNA SEQUENCE (mCT2813) |
| 1365. | MOUSE PROTEIN SEQUENCE (mCP19988) |
| 1366. | HUMAN GENOMIC SEQUENCE (hCG20145) |
| 1367. | HUMAN mRNA SEQUENCE (hCT11220) |
| 1368. | HUMAN PROTEIN SEQUENCE (hCP37850) |
| | CANCER GENE: mCG3757/hCG21349 |
| 1369. | MOUSE GENOMIC SEQUENCE (mCG3757) |
| 1370. | MOUSE mRNA SEQUENCE (mCT1505) |
| 1371. | MOUSE PROTEIN SEQUENCE (mCP6689) |
| 1372. | HUMAN GENOMIC SEQUENCE (hCG21349) |
| 1373. | HUMAN mRNA SEQUENCE (hCT12437) |
| 1374. | HUMAN PROTEIN SEQUENCE (hCP38909) |
| | CANCER GENE: mCG3767/hCG32368 |
| 1375. | MOUSE GENOMIC SEQUENCE (mCG3767) |
| 1376. | MOUSE mRNA SEQUENCE (mCT1502) |
| 1377. | MOUSE PROTEIN SEQUENCE (mCP6695) |
| 1378. | HUMAN GENOMIC SEQUENCE (hCG32368) |
| 1379. | HUMAN mRNA SEQUENCE (hCT23556) |
| 1380. | HUMAN PROTEIN SEQUENCE (hCP45892) |
| | CANCER GENE: mCG3774/hCG21354 |
| 1381. | MOUSE GENOMIC SEQUENCE (mCG3774) |
| 1382. | MOUSE mRNA SEQUENCE (mCT1490) |
| 1383. | MOUSE PROTEIN SEQUENCE (mCP6690) |
| 1384. | HUMAN GENOMIC SEQUENCE (hCG21354) |
| 1385. | HUMAN mRNA SEQUENCE (hCT12442) |
| 1386. | HUMAN PROTEIN SEQUENCE (hCP38903) |
| | CANCER GENE: mCG3775/hCG21354 |
| 1387. | MOUSE GENOMIC SEQUENCE (mCG3775) |
| 1388. | MOUSE mRNA SEQUENCE (mCT1491) |
| 1389. | MOUSE PROTEIN SEQUENCE (mCP6703) |
| 1390. | HUMAN GENOMIC SEQUENCE (hCG21354) |
| 1391. | HUMAN mRNA SEQUENCE (hCT12442) |
| 1392. | HUMAN PROTEIN SEQUENCE (hCP38903) |

TABLE 2-continued

IDENTIFICATION OF SEQUENCES

| SEQ ID NOS. | SEQUENCES |
|---|---|
| | CANCER GENE: mCG3793/hCG27352 |
| 1393. | MOUSE GENOMIC SEQUENCE (mCG3793) |
| 1394. | MOUSE mRNA SEQUENCE (mCT2635) |
| 1395. | MOUSE PROTEIN SEQUENCE (mCP23581) |
| 1396. | HUMAN GENOMIC SEQUENCE (hCG27352) |
| 1397. | HUMAN mRNA SEQUENCE (hCT18491) |
| 1398. | HUMAN PROTEIN SEQUENCE (hCP42955) |
| | CANCER GENE: mCG3824/hCG27823 |
| 1399. | MOUSE GENOMIC SEQUENCE (mCG3824) |
| 1400. | MOUSE mRNA SEQUENCE (mCT1988) |
| 1401. | MOUSE PROTEIN SEQUENCE (mCP22560) |
| 1402. | HUMAN GENOMIC SEQUENCE (hCG27823) |
| 1403. | HUMAN mRNA SEQUENCE (hCT18965) |
| 1404. | HUMAN PROTEIN SEQUENCE (hCP43375) |
| | CANCER GENE: mCG3889/hCG27192 |
| 1405. | MOUSE GENOMIC SEQUENCE (mCG3889) |
| 1406. | MOUSE mRNA SEQUENCE (mCT2598) |
| 1407. | MOUSE PROTEIN SEQUENCE (mCP11982) |
| 1408. | HUMAN GENOMIC SEQUENCE (hCG27192) |
| 1409. | HUMAN mRNA SEQUENCE (hCT1686652) |
| 1410. | HUMAN PROTEIN SEQUENCE (hCP1690976) |
| | CANCER GENE: mCG3931/hCG23145 |
| 1411. | MOUSE GENOMIC SEQUENCE (mCG3931) |
| 1412. | MOUSE mRNA SEQUENCE (mCT2920) |
| 1413. | MOUSE PROTEIN SEQUENCE (mCP21768) |
| 1414. | HUMAN GENOMIC SEQUENCE (hCG23145) |
| 1415. | HUMAN mRNA SEQUENCE (hCT14250) |
| 1416. | HUMAN PROTEIN SEQUENCE (hCP41724) |
| | CANCER GENE: mCG4010/hCG1739389 |
| 1417. | MOUSE GENOMIC SEQUENCE (mCG4010) |
| 1418. | MOUSE mRNA SEQUENCE (mCT2836) |
| 1419. | MOUSE PROTEIN SEQUENCE (mCP14449) |
| 1420. | HUMAN GENOMIC SEQUENCE (hCG1739389) |
| 1421. | HUMAN mRNA SEQUENCE (hCT1777478) |
| 1422. | HUMAN PROTEIN SEQUENCE (hCP1729056) |
| | CANCER GENE: mCG4192/hCG41911 |
| 1423. | MOUSE GENOMIC SEQUENCE (mCG4192) |
| 1424. | MOUSE mRNA SEQUENCE (mCT3038) |
| 1425. | MOUSE PROTEIN SEQUENCE (mCP12251) |
| 1426. | HUMAN GENOMIC SEQUENCE (hCG41911) |
| 1427. | HUMAN mRNA SEQUENCE (hCT33187) |
| 1428. | HUMAN PROTEIN SEQUENCE (hCP51743) |
| | CANCER GENE: mCG4251/hCG1640192 |
| 1429. | MOUSE GENOMIC SEQUENCE (mCG4251) |
| 1430. | MOUSE mRNA SEQUENCE (mCT2936) |
| 1431. | MOUSE PROTEIN SEQUENCE (mCP6497) |
| 1432. | HUMAN GENOMIC SEQUENCE (hCG1640192) |
| 1433. | HUMAN mRNA SEQUENCE (hCT1640319) |
| 1434. | HUMAN PROTEIN SEQUENCE (hCP1640057) |
| | CANCER GENE: mCG4296/hCG40093 |
| 1435. | MOUSE GENOMIC SEQUENCE (mCG4296) |
| 1436. | MOUSE mRNA SEQUENCE (mCT3280) |
| 1437. | MOUSE PROTEIN SEQUENCE (mCP5252) |
| 1438. | HUMAN GENOMIC SEQUENCE (hCG40093) |
| 1439. | HUMAN mRNA SEQUENCE (hCT31347) |
| 1440. | HUMAN PROTEIN SEQUENCE (hCP49868) |
| | CANCER GENE: mCG4317/hCG28302 |
| 1441. | MOUSE GENOMIC SEQUENCE (mCG4317) |
| 1442. | MOUSE mRNA SEQUENCE (mCT3354) |
| 1443. | MOUSE PROTEIN SEQUENCE (mCP18759) |
| 1444. | HUMAN GENOMIC SEQUENCE (hCG28302) |
| 1445. | HUMAN tnRNA SEQUENCE (hCT19451) |
| 1446. | HUMAN PROTEIN SEQUENCE (hCP43793) |

TABLE 2-continued

IDENTIFICATION OF SEQUENCES

| SEQ ID NOS. | SEQUENCES |
|---|---|
| | CANCER GENE: mCG4378/hCG40788 |
| 1447. | MOUSE GENOMIC SEQUENCE (mCG4378) |
| 1448. | MOUSE mRNA SEQUENCE (mCT3175) |
| 1449. | MOUSE PROTEIN SEQUENCE (mCP7522) |
| 1450. | HUMAN GENOMIC SEQUENCE (hCG40788) |
| 1451. | HUMAN mRNA SEQUENCE (hCT32053) |
| 1452. | HUMAN PROTEIN SEQUENCE (hCP50543) |
| | CANCER GENE: mCG4428/hCG30155 |
| 1453. | MOUSE GENOMIC SEQUENCE (mCG4428) |
| 1454. | MOUSE mRNA SEQUENCE (mCT2763) |
| 1455. | MOUSE PROTEIN SEQUENCE (mCP5816) |
| 1456. | HUMAN GENOMIC SEQUENCE (hCG30155) |
| 1457. | HUMAN mRNA SEQUENCE (hCT21322) |
| 1458. | HUMAN PROTEIN SEQUENCE (hCP44763) |
| | CANCER GENE: mCG4463/hCG21099 |
| 1459. | MOUSE GENOMIC SEQUENCE (mCG4463) |
| 1460. | MOUSE mRNA SEQUENCE (mCT2560) |
| 1461. | MOUSE PROTEIN SEQUENCE (mCP3694) |
| 1462. | HUMAN GENOMIC SEQUENCE (hCG21099) |
| 1463. | HUMAN mRNA SEQUENCE (hCT12185) |
| 1464. | HUMAN PROTEIN SEQUENCE (hCP38657) |
| | CANCER GENE: mCG4468/hCG19805 |
| 1465. | MOUSE GENOMIC SEQUENCE (mCG4468) |
| 1466. | MOUSE mRNA SEQUENCE (mCT2554) |
| 1467. | MOUSE PROTEIN SEQUENCE (mCP3698) |
| 1468. | HUMAN GENOMIC SEQUENCE (hCG19805) |
| 1469. | HUMAN mRNA SEQUENCE (hCT10877) |
| 1470. | HUMAN PROTEIN SEQUENCE (hCP38655) |
| | CANCER GENE: mCG4490/hCG39740 |
| 1471. | MOUSE GENOMIC SEQUENCE (mCG4490) |
| 1472. | MOUSE mRNA SEQUENCE (mCT3571) |
| 1473. | MOUSE PROTEIN SEQUENCE (mCP1578) |
| 1474. | HUMAN GENOMIC SEQUENCE (hCG39740) |
| 1475. | HUMAN mRNA SEQUENCE (hCT30992) |
| 1476. | HUMAN PROTEIN SEQUENCE (hCP49525) |
| | CANCER GENE: mCG4492/hCG39730 |
| 1477. | MOUSE GENOMIC SEQUENCE (mCG4492) |
| 1478. | MOUSE mRNA SEQUENCE (mCT3573) |
| 1479. | MOUSE PROTEIN SEQUENCE (mCP1586) |
| 1480. | HUMAN GENOMIC SEQUENCE (hCG39730) |
| 1481. | HUMAN mRNA SEQUENCE (hCT30982) |
| 1482. | HUMAN PROTEIN SEQUENCE (hCP49524) |
| | CANCER GENE: mCG4493/hCG1766501 |
| 1483. | MOUSE GENOMIC SEQUENCE (mCG4493) |
| 1484. | MOUSE mRNA SEQUENCE (mCT3574) |
| 1485. | MOUSE PROTEIN SEQUENCE (mCP1591) |
| 1486. | HUMAN GENOMIC SEQUENCE (hCG1766501) |
| 1487. | HUMAN mRNA SEQUENCE (hCT1805006) |
| 1488. | HUMAN PROTEIN SEQUENCE (hCP1716988) |
| | CANCER GENE: mCG4638/hCG27795 |
| 1489. | MOUSE GENOMIC SEQUENCE (mCG4638) |
| 1490. | MOUSE mRNA SEQUENCE (mCT3972) |
| 1491. | MOUSE PROTEIN SEQUENCE (mCP2223) |
| 1492. | HUMAN GENOMIC SEQUENCE (hCG27795) |
| 1493. | HUMAN mRNA SEQUENCE (hCT18937) |
| 1494. | HUMAN PROTEIN SEQUENCE (hCP43343) |
| | CANCER GENE: mCG4768/hCG22679 |
| 1495. | MOUSE GENOMIC SEQUENCE (mCG4768) |
| 1496. | MOUSE mRNA SEQUENCE (mCT3966) |
| 1497. | MOUSE PROTEIN SEQUENCE (mCP19192) |
| 1498. | HUMAN GENOMIC SEQUENCE (hCG22679) |
| 1499. | HUMAN mRNA SEQUENCE (hCT13777) |
| 1500. | HUMAN PROTEIN SEQUENCE (hCP40139) |

TABLE 2-continued
IDENTIFICATION OF SEQUENCES

| SEQ ID NOS. | SEQUENCES |
|---|---|
| | CANCER GENE: mCG4799/hCG33122 |
| 1501. | MOUSE GENOMIC SEQUENCE (mCG4799) |
| 1502. | MOUSE mRNA SEQUENCE (mCT4081) |
| 1503. | MOUSE PROTEIN SEQUENCE (mCP5240) |
| 1504. | HUMAN GENOMIC SEQUENCE (hCG33122) |
| 1505. | HUMAN mRNA SEQUENCE (hCT24315) |
| 1506. | HUMAN PROTEIN SEQUENCE (hCP46484) |
| | CANCER GENE: mCG4860/hCG22132 |
| 1507. | MOUSE GENOMIC SEQUENCE (mCG4860) |
| 1508. | MOUSE mRNA SEQUENCE (mCT3531) |
| 1509. | MOUSE PROTEIN SEQUENCE (mCP2173) |
| 1510. | HUMAN GENOMIC SEQUENCE (hCG22132) |
| 1511. | HUMAN mRNA SEQUENCE (hCT13225) |
| 1512. | HUMAN PROTEIN SEQUENCE (hCP39660) |
| | CANCER GENE: mCG4940/hCG1785738 |
| 1513. | MOUSE GENOMIC SEQUENCE (mCG4940) |
| 1514. | MOUSE mRNA SEQUENCE (mCT3631) |
| 1515. | MOUSE PROTEIN SEQUENCE (mCP3111) |
| 1516. | HUMAN GENOMIC SEQUENCE (hCG1785738) |
| 1517. | HUMAN mRNA SEQUENCE (hCT1824756) |
| 1518. | HUMAN PROTEIN SEQUENCE (hCP1735762) |
| | CANCER GENE: mCG49939/hCG22769 |
| 1519. | MOUSE GENOMIC SEQUENCE (mCG49939) |
| 1520. | MOUSE mRNA SEQUENCE (mCT50122) |
| 1521. | MOUSE PROTEIN SEQUENCE (mCP36914) |
| 1522. | HUMAN GENOMIC SEQUENCE (hCG22769) |
| 1523. | HUMAN mRNA SEQUENCE (hCT13867) |
| 1524. | HUMAN PROTEIN SEQUENCE (hCP40198) |
| | CANCER GENE: mCG5034/hCG23376 |
| 1525. | MOUSE GENOMIC SEQUENCE (mCG5034) |
| 1526. | MOUSE mRNA SEQUENCE (mCT3881) |
| 1527. | MOUSE PROTEIN SEQUENCE (mCP12076) |
| 1528. | HUMAN GENOMIC SEQUENCE (hCG23376) |
| 1529. | HUMAN mRNA SEQUENCE (hCT14483) |
| 1530. | HUMAN PROTEIN SEQUENCE (hCP40870) |
| | CANCER GENE: mCG5067/hCG19082 |
| 1531. | MOUSE GENOMIC SEQUENCE (mCG5067) |
| 1532. | MOUSE mRNA SEQUENCE (mCT4206) |
| 1533. | MOUSE PROTEIN SEQUENCE (mCP17436) |
| 1534. | HUMAN GENOMIC SEQUENCE (hCG19082) |
| 1535. | HUMAN mRNA SEQUENCE (hCT10147) |
| 1536. | HUMAN PROTEIN SEQUENCE (hCP36703) |
| | CANCER GENE: mCG51010/hCG21464 |
| 1537. | MOUSE GENOMIC SEQUENCE (mCG51010) |
| 1538. | MOUSE mRNA SEQUENCE (mCT51193) |
| 1539. | MOUSE PROTEIN SEQUENCE (mCP24980) |
| 1540. | HUMAN GENOMIC SEQUENCE (hCG21464) |
| 1541. | HUMAN mRNA SEQUENCE (hCT12553) |
| 1542. | HUMAN PROTEIN SEQUENCE (hCP39015) |
| | CANCER GENE: mCG51020/hCG1643989 |
| 1543. | MOUSE GENOMIC SEQUENCE (mCG51020) |
| 1544. | MOUSE mRNA SEQUENCE (mCT51203) |
| 1545. | MOUSE PROTEIN SEQUENCE (mCP28400) |
| 1546. | HUMAN GENOMIC SEQUENCE (hCG1643989) |
| 1547. | HUMAN mRNA SEQUENCE (hCT1644116) |
| 1548. | HUMAN PROTEIN SEQUENCE (hCP1635986) |
| | CANCER GENE: mCG5113/hCG1782397 |
| 1549. | MOUSE GENOMIC SEQUENCE (mCG5113) |
| 1550. | MOUSE mRNA SEQUENCE (mCT3569) |
| 1551. | MOUSE PROTEIN SEQUENCE (mCP8371) |
| 1552. | HUMAN GENOMIC SEQUENCE (hCG1782397) |
| 1553. | HUMAN mRNA SEQUENCE (hCT1821307) |
| 1554. | HUMAN PROTEIN SEQUENCE (hCP1703807) |
| | CANCER GENE: mCG51582/hCG39434 |
| 1555. | MOUSE GENOMIC SEQUENCE (mCG51582) |
| 1556. | MOUSE mRNA SEQUENCE (mCT51765) |
| 1557. | MOUSE PROTEIN SEQUENCE (mCP31229) |
| 1558. | HUMAN GENOMIC SEQUENCE (hCG39434) |
| 1559. | HUMAN mRNA SEQUENCE (hCT30685) |
| 1560. | HUMAN PROTEIN SEQUENCE (hCP49277) |
| | CANCER GENE: mCG51664/hCG28994 |
| 1561. | MOUSE GENOMIC SEQUENCE (mCG51664) |
| 1562. | MOUSE mRNA SEQUENCE (mCT51847) |
| 1563. | MOUSE PROTEIN SEQUENCE (mCP30940) |
| 1564. | HUMAN GENOMIC SEQUENCE (hCG28994) |
| 1565. | HUMAN mRNA SEQUENCE (hCT20153) |
| 1566. | HUMAN PROTEIN SEQUENCE (hCP44268) |
| | CANCER GENE: mCG5362/hCG16933 |
| 1567. | MOUSE GENOMIC SEQUENCE (mCG5362) |
| 1568. | MOUSE mRNA SEQUENCE (mCT4753) |
| 1569. | MOUSE PROTEIN SEQUENCE (mCP11339) |
| 1570. | HUMAN GENOMIC SEQUENCE (hCG16933) |
| 1571. | HUMAN mRNA SEQUENCE (hCT7976) |
| 1572. | HUMAN PROTEIN SEQUENCE (hCP33890) |
| | CANCER GENE: mCG54271/hCG18129 |
| 1573. | MOUSE GENOMIC SEQUENCE (mCG54271) |
| 1574. | MOUSE mRNA SEQUENCE (mCT54454) |
| 1575. | MOUSE PROTEIN SEQUENCE (mCP36490) |
| 1576. | HUMAN GENOMIC SEQUENCE (hCG18129) |
| 1577. | HUMAN mRNA SEQUENCE (hCT9184) |
| 1578. | HUMAN PROTEIN SEQUENCE (hCP36049) |
| | CANCER GENE: mCG5429/hCG38378 |
| 1579. | MOUSE GENOMIC SEQUENCE (mCG5429) |
| 1580. | MOUSE mRNA SEQUENCE (mCT4198) |
| 1581. | MOUSE PROTEIN SEQUENCE (mCP5869) |
| 1582. | HUMAN GENOMIC SEQUENCE (hCG38378) |
| 1583. | HUMAN mRNA SEQUENCE (hCT29619) |
| 1584. | HUMAN PROTEIN SEQUENCE (hCP48301) |
| | CANCER GENE: mCG5448/hCG38103 |
| 1585. | MOUSE GENOMIC SEQUENCE (mCG5448) |
| 1586. | MOUSE mRNA SEQUENCE (mCT4173) |
| 1587. | MOUSE PROTEIN SEQUENCE (mCP5974) |
| 1588. | HUMAN GENOMIC SEQUENCE (hCG38103) |
| 1589. | HUMAN mRNA SEQUENCE (hCT29339) |
| 1590. | HUMAN PROTEIN SEQUENCE (hCP48041) |
| | CANCER GENE: mCG5518/hCG22355 |
| 1591. | MOUSE GENOMIC SEQUENCE (mCG5518 |
| 1592. | MOUSE mRNA SEQUENCE (mCT4373) |
| 1593. | MOUSE PROTEIN SEQUENCE (mCP3274) |
| 1594. | HUMAN GENOMIC SEQUENCE (hCG22355) |
| 1595. | HUMAN mRNA SEQUENCE (hCT13449) |
| 1596. | HUMAN PROTEIN SEQUENCE (hCP39839) |
| | CANCER GENE: mCG5530/hCG22353 |
| 1597. | MOUSE GENOMIC SEQUENCE (mCG5530) |
| 1598. | MOUSE mRNA SEQUENCE (mCT4367) |
| 1599. | MOUSE PROTEIN SEQUENCE (mCP3095) |
| 1600. | HUMAN GENOMIC SEQUENCE (hCG22353) |
| 1601. | HUMAN mRNA SEQUENCE (hCT13447) |
| 1602. | HUMAN PROTEIN SEQUENCE (hCP39837) |
| | CANCER GENE: mCG5531/hCG20493 |
| 1603. | MOUSE GENOMIC SEQUENCE (mCG5531) |
| 1604. | MOUSE mRNA SEQUENCE (mCT4361) |
| 1605. | MOUSE PROTEIN SEQUENCE (mCP3277) |
| 1606. | HUMAN GENOMIC SEQUENCE (hCG20493) |
| 1607. | HUMAN mRNA SEQUENCE (hCT13441) |
| 1608. | HUMAN PROTEIN SEQUENCE (hCP39842) |

TABLE 2-continued

IDENTIFICATION OF SEQUENCES

| SEQ ID NOS. | SEQUENCES |
|---|---|
| | CANCER GENE: mCG5548/hCG1779020 |
| 1609. | MOUSE GENOMIC SEQUENCE (mCG5548) |
| 1610. | MOUSE mRNA SEQUENCE (mCT4831) |
| 1611. | MOUSE PROTEIN SEQUENCE (mCP6232) |
| 1612. | HUMAN GENOMIC SEQUENCE (hCG1779020) |
| 1613. | HUMAN mRNA SEQUENCE (hCT1817821) |
| 1614. | HUMAN PROTEIN SEQUENCE (hCP1711875) |
| | CANCER GENE: mCG5662/hCG14831 |
| 1615. | MOUSE GENOMIC SEQUENCE (mCG5662) |
| 1616. | MOUSE mRNA SEQUENCE (mCT5106) |
| 1617. | MOUSE PROTEIN SEQUENCE (mCP2831) |
| 1618. | HUMAN GENOMIC SEQUENCE (hCG14831) |
| 1619. | HUMAN mRNA SEQUENCE (hCT1954392) |
| 1620. | HUMAN PROTEIN SEQUENCE (hCP1764868) |
| | CANCER GENE: mCG57125/hCG1742422 |
| 1621. | MOUSE GENOMIC SEQUENCE (mCG57125) |
| 1622. | MOUSE mRNA SEQUENCE (mCT57308) |
| 1623. | MOUSE PROTEIN SEQUENCE (mCP31688) |
| 1624. | HUMAN GENOMIC SEQUENCE (hCG1742422) |
| 1625. | HUMAN mRNA SEQUENCE (hCT1780585) |
| 1626. | HUMAN PROTEIN SEQUENCE (hCP1704804) |
| | CANCER GENE: mCG5728/hCG1811271 |
| 1627. | MOUSE GENOMIC SEQUENCE (mCG5728) |
| 1628. | MOUSE mRNA SEQUENCE (mCT5307) |
| 1629. | MOUSE PROTEIN SEQUENCE (mCP22455) |
| 1630. | HUMAN GENOMIC SEQUENCE (hCG1811271) |
| 1631. | HUMAN mRNA SEQUENCE (hCT1951996) |
| 1632. | HUMAN PROTEIN SEQUENCE (hCP1751951) |
| | CANCER GENE: mCG5738/hCG37394 |
| 1633. | MOUSE GENOMIC SEQUENCE (mCG5738) |
| 1634. | MOUSE mRNA SEQUENCE (mCT5149) |
| 1635. | MOUSE PROTEIN SEQUENCE (mCP11789) |
| 1636. | HUMAN GENOMIC SEQUENCE (hCG37394) |
| 1637. | HUMAN mRNA SEQUENCE (hCT1950688) |
| 1638. | HUMAN PROTEIN SEQUENCE (hCP1764248) |
| | CANCER GENE: mCG5779/hCG21040 |
| 1639. | MOUSE GENOMIC SEQUENCE (mCG5779) |
| 1640. | MOUSE mRNA SEQUENCE (mCT4807) |
| 1641. | MOUSE PROTEIN SEQUENCE (mCP5664) |
| 1642. | HUMAN GENOMIC SEQUENCE (hCG21040) |
| 1643. | HUMAN mRNA SEQUENCE (hCT12126) |
| 1644. | HUMAN PROTEIN SEQUENCE (hCP45937) |
| | CANCER GENE: mCG5868/hCG28297 |
| 1645. | MOUSE GENOMIC SEQUENCE (mCG5868) |
| 1646. | MOUSE mRNA SEQUENCE (mCT4586) |
| 1647. | MOUSE PROTEIN SEQUENCE (mCP1369) |
| 1648. | HUMAN GENOMIC SEQUENCE (hCG28297) |
| 1649. | HUMAN mRNA SEQUENCE (hCT19445) |
| 1650. | HUMAN PROTEIN SEQUENCE (hCP45156) |
| | CANCER GENE: mCG6000/hCG1777660 |
| 1651. | MOUSE GENOMIC SEQUENCE (mCG6000) |
| 1652. | MOUSE mRNA SEQUENCE (mCT4635) |
| 1653. | MOUSE PROTEIN SEQUENCE (mCP9274) |
| 1654. | HUMAN GENOMIC SEQUENCE (hCG1777660) |
| 1655. | HUMAN mRNA SEQUENCE (hCT1816404) |
| 1656. | HUMAN PROTEIN SEQUENCE (hCP1711146) |
| | CANCER GENE: mCG6027/hCG38622 |
| 1657. | MOUSE GENOMIC SEQUENCE (mCG6027) |
| 1658. | MOUSE mRNA SEQUENCE (mCT4725) |
| 1659. | MOUSE PROTEIN SEQUENCE (mCP21553) |
| 1660. | HUMAN GENOMIC SEQUENCE (hCG38622) |
| 1661. | HUMAN mRNA SEQUENCE (hCT1952786) |
| 1662. | HUMAN PROTEIN SEQUENCE (hCP1762380) |
| | CANCER GENE: mCG6056/hCG37193 |
| 1663. | MOUSE GENOMIC SEQUENCE (mCG6056) |
| 1664. | MOUSE mRNA SEQUENCE (mCT5154) |
| 1665. | MOUSE PROTEIN SEQUENCE (mCP10360) |
| 1666. | HUMAN GENOMIC SEQUENCE (hCG37193) |
| 1667. | HUMAN mRNA SEQUENCE (hCT28423) |
| 1668. | HUMAN PROTEIN SEQUENCE (hCP48388) |
| | CANCER GENE: mCG6178/hCG33356 |
| 1669. | MOUSE GENOMIC SEQUENCE (mCG6178) |
| 1670. | MOUSE mRNA SEQUENCE (mCT5450) |
| 1671. | MOUSE PROTEIN SEQUENCE (mCP12373) |
| 1672. | HUMAN GENOMIC SEQUENCE (hCG33356) |
| 1673. | HUMAN mRNA SEQUENCE (hCT24551) |
| 1674. | HUMAN PROTEIN SEQUENCE (hCP46689) |
| | CANCER GENE: mCG6322/hCG32986 |
| 1675. | MOUSE GENOMIC SEQUENCE (mCG6322) |
| 1676. | MOUSE mRNA SEQUENCE (mCT5536) |
| 1677. | MOUSE PROTEIN SEQUENCE (mCP16472) |
| 1678. | HUMAN GENOMIC SEQUENCE (hCG32986) |
| 1679. | HUMAN mRNA SEQUENCE (hCT24178) |
| 1680. | HUMAN PROTEIN SEQUENCE (hCP46302) |
| | CANCER GENE: mCG6388/hCG38644 |
| 1681. | MOUSE GENOMIC SEQUENCE (mCG6388) |
| 1682. | MOUSE mRNA SEQUENCE (mCT5698) |
| 1683. | MOUSE PROTEIN SEQUENCE (mCP20186) |
| 1684. | HUMAN GENOMIC SEQUENCE (hCG38644) |
| 1685. | HUMAN mRNA SEQUENCE (hCT29887) |
| 1686. | HUMAN PROTEIN SEQUENCE (hCP48469) |
| | CANCER GENE: mCG6403/hCG38453 |
| 1687. | MOUSE GENOMIC SEQUENCE (mCG6403) |
| 1688. | MOUSE mRNA SEQUENCE (mCT5643) |
| 1689. | MOUSE PROTEIN SEQUENCE (mCP20171) |
| 1690. | HUMAN GENOMIC SEQUENCE (hCG38453) |
| 1691. | HUMAN mRNA SEQUENCE (hCT29696) |
| 1692. | HUMAN PROTEIN SEQUENCE (hCP48358) |
| | CANCER GENE: mCG6481/hCG40757 |
| 1693. | MOUSE GENOMIC SEQUENCE (mCG6481) |
| 1694. | MOUSE mRNA SEQUENCE (mCT5786) |
| 1695. | MOUSE PROTEIN SEQUENCE (mCP18415) |
| 1696. | HUMAN GENOMIC SEQUENCE (hCG40757) |
| 1697. | HUMAN mRNA SEQUENCE (hCT32019) |
| 1698. | HUMAN PROTEIN SEQUENCE (hCP50491) |
| | CANCER GENE: mCG6500/hCG14773 |
| 1699. | MOUSE GENOMIC SEQUENCE (mCG6500) |
| 1700. | MOUSE mRNA SEQUENCE (mCT5731) |
| 1701. | MOUSE PROTEIN SEQUENCE (mCP16037) |
| 1702. | HUMAN GENOMIC SEQUENCE (hCG14773) |
| 1703. | HUMAN mRNA SEQUENCE (hCT5794) |
| 1704. | HUMAN PROTEIN SEQUENCE (hCP35369) |
| | CANCER GENE: mCG6549/hCG37127 |
| 1705. | MOUSE GENOMIC SEQUENCE (mCG6549) |
| 1706. | MOUSE mRNA SEQUENCE (mCT6076) |
| 1707. | MOUSE PROTEIN SEQUENCE (mCP6001) |
| 1708. | HUMAN GENOMIC SEQUENCE (hCG37127) |
| 1709. | HUMAN mRNA SEQUENCE (hCT1950762) |
| 1710. | HUMAN PROTEIN SEQUENCE (hCP1767501) |
| | CANCER GENE: mCG6627/hCG27461 |
| 1711. | MOUSE GENOMIC SEQUENCE (mCG6627) |
| 1712. | MOUSE mRNA SEQUENCE (mCT4944) |
| 1713. | MOUSE PROTEIN SEQUENCE (mCP18836) |
| 1714. | HUMAN GENOMIC SEQUENCE (hCG27461) |
| 1715. | HUMAN mRNA SEQUENCE (hCT18601) |
| 1716. | HUMAN PROTEIN SEQUENCE (hCP43032) |

TABLE 2-continued

IDENTIFICATION OF SEQUENCES

| SEQ ID NOS. | SEQUENCES |
|---|---|
| | CANCER GENE: mCG6631/hCG29839 |
| 1717. | MOUSE GENOMIC SEQUENCE (mCG6631) |
| 1718. | MOUSE mRNA SEQUENCE (mCT4941) |
| 1719. | MOUSE PROTEIN SEQUENCE (mCP18882) |
| 1720. | HUMAN GENOMIC SEQUENCE (hCG29839) |
| 1721. | HUMAN mRNA SEQUENCE (hCT21006) |
| 1722. | HUMAN PROTEIN SEQUENCE (hCP44613) |
| | CANCER GENE: mCG66316/hCG29191 |
| 1723. | MOUSE GENOMIC SEQUENCE (mCG66316) |
| 1724. | MOUSE mRNA SEQUENCE (mCT66499) |
| 1725. | MOUSE PROTEIN SEQUENCE (mCP40302) |
| 1726. | HUMAN GENOMIC SEQUENCE (hCG29191) |
| 1727. | HUMAN mRNA SEQUENCE (hCT1951169) |
| 1728. | HUMAN PROTEIN SEQUENCE (hCP1766688) |
| | CANCER GENE: mCG6636/hCG33210 |
| 1729. | MOUSE GENOMIC SEQUENCE (mCG6636) |
| 1730. | MOUSE mRNA SEQUENCE (mCT4916) |
| 1731. | MOUSE PROTEIN SEQUENCE (mCP3446) |
| 1732. | HUMAN GENOMIC SEQUENCE (hCG33210) |
| 1733. | HUMAN mRNA SEQUENCE (hCT24403) |
| 1734. | HUMAN PROTEIN SEQUENCE (hCP46579) |
| | CANCER GENE: mCG6875/hCG32956 |
| 1735. | MOUSE GENOMIC SEQUENCE (mCG6875) |
| 1736. | MOUSE mRNA SEQUENCE (mCT5377) |
| 1737. | MOUSE PROTEIN SEQUENCE (mCP8851) |
| 1738. | HUMAN GENOMIC SEQUENCE (hCG32956) |
| 1739. | HUMAN mRNA SEQUENCE (hCT1686636) |
| 1740. | HUMAN PROTEIN SEQUENCE (hCP1690129) |
| | CANCER GENE: mCG6919/hCG1644194 |
| 1741. | MOUSE GENOMIC SEQUENCE (mCG6919) |
| 1742. | MOUSE mRNA SEQUENCE (mCT5869) |
| 1743. | MOUSE PROTEIN SEQUENCE (mCP10200) |
| 1744. | HUMAN GENOMIC SEQUENCE (hCG1644194) |
| 1745. | HUMAN mRNA SEQUENCE (hCT1644321) |
| 1746. | HUMAN PROTEIN SEQUENCE (hCP1641003) |
| | CANCER GENE: mCG6945/hCG14907 |
| 1747. | MOUSE GENOMIC SEQUENCE (mCG6945) |
| 1748. | MOUSE mRNA SEQUENCE (mCT5912) |
| 1749. | MOUSE PROTEIN SEQUENCE (mCP6966) |
| 1750. | HUMAN GENOMIC SEQUENCE (hCG14907) |
| 1751. | HUMAN mRNA SEQUENCE (hCT5928) |
| 1752. | HUMAN PROTEIN SEQUENCE (hCP33928) |
| | CANCER GENE: mCG6974/hCG17395 |
| 1753. | MOUSE GENOMIC SEQUENCE (mCG6974) |
| 1754. | MOUSE mRNA SEQUENCE (mCT5770) |
| 1755. | MOUSE PROTEIN SEQUENCE (mCP7427) |
| 1756. | HUMAN GENOMIC SEQUENCE (hCG17395) |
| 1757. | HUMAN mRNA SEQUENCE (hCT8445) |
| 1758. | HUMAN PROTEIN SEQUENCE (hCP33979) |
| | CANCER GENE: mCG6981/hCG1735348 |
| 1759. | MOUSE GENOMIC SEQUENCE (mCG6981) |
| 1760. | MOUSE mRNA SEQUENCE (mCT5634) |
| 1761. | MOUSE PROTEIN SEQUENCE (mCP7937) |
| 1762. | HUMAN GENOMIC SEQUENCE (hCG1735348) |
| 1763. | HUMAN mRNA SEQUENCE (hCT1773342) |
| 1764. | HUMAN PROTEIN SEQUENCE (hCP1705220) |
| | CANCER GENE: mCG7008/hCG25055 |
| 1765. | MOUSE GENOMIC SEQUENCE (mCG7008) |
| 1766. | MOUSE mRNA SEQUENCE (mCT5582) |
| 1767. | MOUSE PROTEIN SEQUENCE (mCP18363) |
| 1768. | HUMAN GENOMIC SEQUENCE (hCG25055) |
| 1769. | HUMAN mRNA SEQUENCE (hCT16177) |
| 1770. | HUMAN PROTEIN SEQUENCE (hCP41953) |
| | CANCER GENE: mCG7143/hCG32521 |
| 1771. | MOUSE GENOMIC SEQUENCE (mCG7143) |
| 1772. | MOUSE mRNA SEQUENCE (mCT6024) |
| 1773. | MOUSE PROTEIN SEQUENCE (mCP20132) |
| 1774. | HUMAN GENOMIC SEQUENCE (hCG32521) |
| 1775. | HUMAN mRNA SEQUENCE (hCT23710) |
| 1776. | HUMAN PROTEIN SEQUENCE (hCP45837) |
| | CANCER GENE: mCG7189/hCG1640838 |
| 1777. | MOUSE GENOMIC SEQUENCE (mCG7189) |
| 1778. | MOUSE mRNA SEQUENCE (mCT6099) |
| 1779. | MOUSE PROTEIN SEQUENCE (mCP6124) |
| 1780. | HUMAN GENOMIC SEQUENCE (hCG1640838) |
| 1781. | HUMAN mRNA SEQUENCE (hCT1640965) |
| 1782. | HUMAN PROTEIN SEQUENCE (hCP1622409) |
| | CANCER GENE: mCG7211/hCG1781938 |
| 1783. | MOUSE GENOMIC SEQUENCE (mCG7211) |
| 1784. | MOUSE mRNA SEQUENCE (mCT6016) |
| 1785. | MOUSE PROTEIN SEQUENCE (mCP4537) |
| 1786. | HUMAN GENOMIC SEQUENCE (hCG1781938) |
| 1787. | HUMAN mRNA SEQUENCE (hCT1820826) |
| 1788. | HUMAN PROTEIN SEQUENCE (hCP1698824) |
| | CANCER GENE: mCG7212/hCG37223 |
| 1789. | MOUSE GENOMIC SEQUENCE (mCG7212) |
| 1790. | MOUSE mRNA SEQUENCE (mCT6017) |
| 1791. | MOUSE PROTEIN SEQUENCE (mCP4540) |
| 1792. | HUMAN GENOMIC SEQUENCE (hCG37223) |
| 1793. | HUMAN mRNA SEQUENCE (hCT1952513) |
| 1794. | HUMAN PROTEIN SEQUENCE (hCP1761013) |
| | CANCER GENE: mCG7256/hCG39345 |
| 1795. | MOUSE GENOMIC SEQUENCE (mCG7256) |
| 1796. | MOUSE mRNA SEQUENCE (mCT3682) |
| 1797. | MOUSE PROTEIN SEQUENCE (mCP15726) |
| 1798. | HUMAN GENOMIC SEQUENCE (hCG39345) |
| 1799. | HUMAN mRNA SEQUENCE (hCT30596) |
| 1800. | HUMAN PROTEIN SEQUENCE (hCP49488) |
| | CANCER GENE: mCG7264/hCG39344 |
| 1801. | MOUSE GENOMIC SEQUENCE (mCG7264) |
| 1802. | MOUSE mRNA SEQUENCE (mCT3672) |
| 1803. | MOUSE PROTEIN SEQUENCE (mCP15739) |
| 1804. | HUMAN GENOMIC SEQUENCE (hCG39344) |
| 1805. | HUMAN mRNA SEQUENCE (hCT1950668) |
| 1806. | HUMAN PROTEIN SEQUENCE (hCP1752538) |
| | CANCER GENE: mCG7348/hCG28560 |
| 1807. | MOUSE GENOMIC SEQUENCE (mCG7348) |
| 1808. | MOUSE mRNA SEQUENCE (mCT6342) |
| 1809. | MOUSE PROTEIN SEQUENCE (mCP20154) |
| 1810. | HUMAN GENOMIC SEQUENCE (hCG28560) |
| 1811. | HUMAN mRNA SEQUENCE (hCT19714) |
| 1812. | HUMAN PROTEIN SEQUENCE (hCP43996) |
| | CANCER GENE: mCG7369/hCG22856 |
| 1813. | MOUSE GENOMIC SEQUENCE (mCG7369) |
| 1814. | MOUSE mRNA SEQUENCE (mCT6267) |
| 1815. | MOUSE PROTEIN SEQUENCE (mCP9400) |
| 1816. | HUMAN GENOMIC SEQUENCE (hCG22856) |
| 1817. | HUMAN mRNA SEQUENCE (hCT13954) |
| 1818. | HUMAN PROTEIN SEQUENCE (hCP40284) |
| | CANCER GENE: mCG7522/hCG32930 |
| 1819. | MOUSE GENOMIC SEQUENCE (mCG7522) |
| 1820. | MOUSE mRNA SEQUENCE (mCT6508) |
| 1821. | MOUSE PROTEIN SEQUENCE (mCP11731) |
| 1822. | HUMAN GENOMIC SEQUENCE (hCG32930) |
| 1823. | HUMAN mRNA SEQUENCE (hCT24122) |
| 1824. | HUMAN PROTEIN SEQUENCE (hCP46487) |

TABLE 2-continued

IDENTIFICATION OF SEQUENCES

| SEQ ID NOS. | SEQUENCES |
|---|---|
| | CANCER GENE: mCG7669/hCG30694 |
| 1825. | MOUSE GENOMIC SEQUENCE (mCG7669) |
| 1826. | MOUSE mRNA SEQUENCE (mCT6381) |
| 1827. | MOUSE PROTEIN SEQUENCE (mCP9354) |
| 1828. | HUMAN GENOMIC SEQUENCE (hCG30694) |
| 1829. | HUMAN mRNA SEQUENCE (hCT1952710) |
| 1830. | HUMAN PROTEIN SEQUENCE (hCP1766207) |
| | CANCER GENE: mCG7689/hCG32392 |
| 1831. | MOUSE GENOMIC SEQUENCE (mCG7689) |
| 1832. | MOUSE mRNA SEQUENCE (mCT6573) |
| 1833. | MOUSE PROTEIN SEQUENCE (mCP11083) |
| 1834. | HUMAN GENOMIC SEQUENCE (hCG32392) |
| 1835. | HUMAN mRNA SEQUENCE (hCT23580) |
| 1836. | HUMAN PROTEIN SEQUENCE (hCP46697) |
| | CANCER GENE: mCG7785/hCG24868 |
| 1837. | MOUSE GENOMIC SEQUENCE (mCG7785) |
| 1838. | MOUSE mRNA SEQUENCE (mCT6917) |
| 1839. | MOUSE PROTEIN SEQUENCE (mCP18186) |
| 1840. | HUMAN GENOMIC SEQUENCE (hCG24868) |
| 1841. | HUMAN mRNA SEQUENCE (hCT15989) |
| 1842. | HUMAN PROTEIN SEQUENCE (hCP41880) |
| | CANCER GENE: mCG7804/hCG39065 |
| 1843. | MOUSE GENOMIC SEQUENCE (mCG7804) |
| 1844. | MOUSE mRNA SEQUENCE (mCT6952) |
| 1845. | MOUSE PROTEIN SEQUENCE (mCP3002) |
| 1846. | HUMAN GENOMIC SEQUENCE (hCG39065) |
| 1847. | HUMAN mRNA SEQUENCE (hCT30312) |
| 1848. | HUMAN PROTEIN SEQUENCE (hCP48906) |
| | CANCER GENE: mCG7826/hCG1735557 |
| 1849. | MOUSE GENOMIC SEQUENCE (mCG7826) |
| 1850. | MOUSE mRNA SEQUENCE (mCT6588) |
| 1851. | MOUSE PROTEIN SEQUENCE (mCP13941) |
| 1852. | HUMAN GENOMIC SEQUENCE (hCG1735557) |
| 1853. | HUMAN mRNA SEQUENCE (hCT1773553) |
| 1854. | HUMAN PROTEIN SEQUENCE (hCP1731122) |
| | CANCER GENE: mCG7831/hCG37578 |
| 1855. | MOUSE GENOMIC SEQUENCE (mCG7831) |
| 1856. | MOUSE mRNA SEQUENCE (mCT6886) |
| 1857. | MOUSE PROTEIN SEQUENCE (mCP18535) |
| 1858. | HUMAN GENOMIC SEQUENCE (hCG37578) |
| 1859. | HUMAN mRNA SEQUENCE (hCT28811) |
| 1860. | HUMAN PROTEIN SEQUENCE (hCP47543) |
| | CANCER GENE: mCG7923/hCG22125 |
| 1861. | MOUSE GENOMIC SEQUENCE (mCG7923) |
| 1862. | MOUSE mRNA SEQUENCE (mCT6738) |
| 1863. | MOUSE PROTEIN SEQUENCE (mCP3098) |
| 1864. | HUMAN GENOMIC SEQUENCE (hCG22125) |
| 1865. | HUMAN mRNA SEQUENCE (hCT13218) |
| 1866. | HUMAN PROTEIN SEQUENCE (hCP39611) |
| | CANCER GENE: mCG7927/hCG20927 |
| 1867. | MOUSE GENOMIC SEQUENCE (mCG7927) |
| 1868. | MOUSE mRNA SEQUENCE (mCT6729) |
| 1869. | MOUSE PROTEIN SEQUENCE (mCP3261) |
| 1870. | HUMAN GENOMIC SEQUENCE (hCG20927) |
| 1871. | HUMAN mRNA SEQUENCE (hCT12009) |
| 1872. | HUMAN PROTEIN SEQUENCE (hCP38533) |
| | CANCER GENE: mCG7964/hCG27325 |
| 1873. | MOUSE GENOMIC SEQUENCE (mCG7964) |
| 1874. | MOUSE mRNA SEQUENCE (mCT7300) |
| 1875. | MOUSE PROTEIN SEQUENCE (mCP18236) |
| 1876. | HUMAN GENOMIC SEQUENCE (hCG27325) |
| 1877. | HUMAN mRNA SEQUENCE (hCT18464) |
| 1878. | HUMAN PROTEIN SEQUENCE (hCP42919) |
| | CANCER GENE: mCG8211/hCG24168 |
| 1879. | MOUSE GENOMIC SEQUENCE (mCG8211) |
| 1880. | MOUSE mRNA SEQUENCE (mCT7649) |
| 1881. | MOUSE PROTEIN SEQUENCE (mCP21082) |
| 1882. | HUMAN GENOMIC SEQUENCE (hCG24168) |
| 1883. | HUMAN mRNA SEQUENCE (hCT15282) |
| 1884. | HUMAN PROTEIN SEQUENCE (hCP41497) |
| | CANCER GENE: mCG8306/hCG18967 |
| 1885. | MOUSE GENOMIC SEQUENCE (mCG8306) |
| 1886. | MOUSE mRNA SEQUENCE (mCT7487) |
| 1887. | MOUSE PROTEIN SEQUENCE (mCP11411) |
| 1888. | HUMAN GENOMIC SEQUENCE (hCG18967) |
| 1889. | HUMAN mRNA SEQUENCE (hCT10032) |
| 1890. | HUMAN PROTEIN SEQUENCE (hCP37047) |
| | CANCER GENE: mCG8426/hCG27711 |
| 1891. | MOUSE GENOMIC SEQUENCE (mCG8426) |
| 1892. | MOUSE mRNA SEQUENCE (mCT7097) |
| 1893. | MOUSE PROTEIN SEQUENCE (mCP9700) |
| 1894. | HUMAN GENOMIC SEQUENCE (hCG27711) |
| 1895. | HUMAN mRNA SEQUENCE (hCT18853) |
| 1896. | HUMAN PROTEIN SEQUENCE (hCP43269) |
| | CANCER GENE: mCG8466/hCG29605 |
| 1897. | MOUSE GENOMIC SEQUENCE (mCG8466) |
| 1898. | MOUSE mRNA SEQUENCE (mCT7481) |
| 1899. | MOUSE PROTEIN SEQUENCE (mCP18300) |
| 1900. | HUMAN GENOMIC SEQUENCE (hCG29605) |
| 1901. | HUMAN mRNA SEQUENCE (hCT1816740) |
| 1902. | HUMAN PROTEIN SEQUENCE (hCP1739247) |
| | CANCER GENE: mCG8527/hCG34336 |
| 1903. | MOUSE GENOMIC SEQUENCE (mCG8527) |
| 1904. | MOUSE mRNA SEQUENCE (mCT7245) |
| 1905. | MOUSE PROTEIN SEQUENCE (mCP15644) |
| 1906. | HUMAN GENOMIC SEQUENCE (hCG34336) |
| 1907. | HUMAN mRNA SEQUENCE (hCT25539) |
| 1908. | HUMAN PROTEIN SEQUENCE (hCP46979) |
| | CANCER GENE: mCG8564/hCG27679 |
| 1909. | MOUSE GENOMIC SEQUENCE (mCG8564) |
| 1910. | MOUSE mRNA SEQUENCE (mCT7392) |
| 1911. | MOUSE PROTEIN SEQUENCE (mCP18404) |
| 1912. | HUMAN GENOMIC SEQUENCE (hCG27679) |
| 1913. | HUMAN mRNA SEQUENCE (hCT18820) |
| 1914. | HUMAN PROTEIN SEQUENCE (hCP43233) |
| | CANCER GENE: mCG8581/hCG14605 |
| 1915. | MOUSE GENOMIC SEQUENCE (mCG8581) |
| 1916. | MOUSE mRNA SEQUENCE (mCT7409) |
| 1917. | MOUSE PROTEIN SEQUENCE (mCP13660) |
| 1918. | HUMAN GENOMIC SEQUENCE (hCG14605) |
| 1919. | HUMAN mRNA SEQUENCE (hCT5626) |
| 1920. | HUMAN PROTEIN SEQUENCE (hCP33329) |
| | CANCER GENE: mCG8584/hCG15017 |
| 1921. | MOUSE GENOMIC SEQUENCE (mCG8584) |
| 1922. | MOUSE mRNA SEQUENCE (mCT7403) |
| 1923. | MOUSE PROTEIN SEQUENCE (mCP13663) |
| 1924. | HUMAN GENOMIC SEQUENCE (hCG15017) |
| 1925. | HUMAN mRNA SEQUENCE (hCT6038) |
| 1926. | HUMAN PROTEIN SEQUENCE (hCP35730) |
| | CANCER GENE: mCG8821/hCG31443 |
| 1927. | MOUSE GENOMIC SEQUENCE (mCG8821) |
| 1928. | MOUSE mRNA SEQUENCE (mCT9309) |
| 1929. | MOUSE PROTEIN SEQUENCE (mCP13907) |
| 1930. | HUMAN GENOMIC SEQUENCE (hCG31443) |
| 1931. | HUMAN mRNA SEQUENCE (hCT1958026) |
| 1932. | HUMAN PROTEIN SEQUENCE (hCP1762737) |

TABLE 2-continued

IDENTIFICATION OF SEQUENCES

| SEQ ID NOS. | SEQUENCES |
|---|---|
|  | CANCER GENE: mCG8835/hCG17175 |
| 1933. | MOUSE GENOMIC SEQUENCE (mCG8835) |
| 1934. | MOUSE mRNA SEQUENCE (mCT9428) |
| 1935. | MOUSE PROTEIN SEQUENCE (mCP22858) |
| 1936. | HUMAN GENOMIC SEQUENCE (hCG17175) |
| 1937. | HUMAN mRNA SEQUENCE (hCT1954427) |
| 1938. | HUMAN PROTEIN SEQUENCE (hCP1764428) |
|  | CANCER GENE: mCG8893/hCG19941 |
| 1939. | MOUSE GENOMIC SEQUENCE (mCG8893) |
| 1940. | MOUSE mRNA SEQUENCE (mCT9941) |
| 1941. | MOUSE PROTEIN SEQUENCE (mCP11443) |
| 1942. | HUMAN GENOMIC SEQUENCE (hCG19941) |
| 1943. | HUMAN mRNA SEQUENCE (hCT11013) |
| 1944. | HUMAN PROTEIN SEQUENCE (hCP37649) |
|  | CANCER GENE: mCG8963/hCG1639824 |
| 1945. | MOUSE GENOMIC SEQUENCE (mCG8963) |
| 1946. | MOUSE mRNA SEQUENCE (mCT8905) |
| 1947. | MOUSE PROTEIN SEQUENCE (mCP20497) |
| 1948. | HUMAN GENOMIC SEQUENCE (hCG1639824) |
| 1949. | HUMAN mRNA SEQUENCE (hCT1639951) |
| 1950. | HUMAN PROTEIN SEQUENCE (hCP1609218) |
|  | CANCER GENE: mCG8993/hCG34092 |
| 1951. | MOUSE GENOMIC SEQUENCE (mCG8993) |
| 1952. | MOUSE mRNA SEQUENCE (mCT8968) |
| 1953. | MOUSE PROTEIN SEQUENCE (mCP11923) |
| 1954. | HUMAN GENOMIC SEQUENCE (hCG34092) |
| 1955. | HUMAN mRNA SEQUENCE (hCT25292) |
| 1956. | HUMAN PROTEIN SEQUENCE (hCP46939) |
|  | CANCER GENE: mCG9022/hCG32769 |
| 1957. | MOUSE GENOMIC SEQUENCE (mCG9022) |
| 1958. | MOUSE mRNA SEQUENCE (mCT9076) |
| 1959. | MOUSE PROTEIN SEQUENCE (mCP14863) |
| 1960. | HUMAN GENOMIC SEQUENCE (hCG32769) |
| 1961. | HUMAN mRNA SEQUENCE (hCT23960) |
| 1962. | HUMAN PROTEIN SEQUENCE (hCP46122) |
|  | CANCER GENE: mCG9049/hCG25130 |
| 1963. | MOUSE GENOMIC SEQUENCE (mCG9049) |
| 1964. | MOUSE mRNA SEQUENCE (mCT9186) |
| 1965. | MOUSE PROTEIN SEQUENCE (mCP8512) |
| 1966. | HUMAN GENOMIC SEQUENCE (hCG25130) |
| 1967. | HUMAN mRNA SEQUENCE (hCT16254) |
| 1968. | HUMAN PROTEIN SEQUENCE (hCP42053) |
|  | CANCER GENE: mCG9061/hCG37877 |
| 1969. | MOUSE GENOMIC SEQUENCE (mCG9061) |
| 1970. | MOUSE mRNA SEQUENCE (mCT9106) |
| 1971. | MOUSE PROTEIN SEQUENCE (mCP6323) |
| 1972. | HUMAN GENOMIC SEQUENCE (hCG37877) |
| 1973. | HUMAN mRNA SEQUENCE (hCT29112) |
| 1974. | HUMAN PROTEIN SEQUENCE (hCP47826) |
|  | CANCER GENE: mCG9066/hCG37872 |
| 1975. | MOUSE GENOMIC SEQUENCE (mCG9066) |
| 1976. | MOUSE mRNA SEQUENCE (mCT9112) |
| 1977. | MOUSE PROTEIN SEQUENCE (mCP6294) |
| 1978. | HUMAN GENOMIC SEQUENCE (hCG37872) |
| 1979. | HUMAN mRNA SEQUENCE (hCT29107) |
| 1980. | HUMAN PROTEIN SEQUENCE (hCP47828) |
|  | CANCER GENE: mCG9077/hCG23504 |
| 1981. | MOUSE GENOMIC SEQUENCE (mCG9077) |
| 1982. | MOUSE mRNA SEQUENCE (mCT9209) |
| 1983. | MOUSE PROTEIN SEQUENCE (mCP4875) |
| 1984. | HUMAN GENOMIC SEQUENCE (hCG23504) |
| 1985. | HUMAN mRNA SEQUENCE (hCT1686496) |
| 1986. | HUMAN PROTEIN SEQUENCE (hCP1689892) |

TABLE 2-continued

IDENTIFICATION OF SEQUENCES

| SEQ ID NOS. | SEQUENCES |
|---|---|
|  | CANCER GENE: mCG9223/hCG15927 |
| 1987. | MOUSE GENOMIC SEQUENCE (mCG9223) |
| 1988. | MOUSE mRNA SEQUENCE (mCT9154) |
| 1989. | MOUSE PROTEIN SEQUENCE (mCP13326) |
| 1990. | HUMAN GENOMIC SEQUENCE (hCG15927) |
| 1991. | HUMAN mRNA SEQUENCE (hCT6957) |
| 1992. | HUMAN PROTEIN SEQUENCE (hCP35436) |
|  | CANCER GENE: mCG9253/hCG22665 |
| 1993. | MOUSE GENOMIC SEQUENCE (mCG9253) |
| 1994. | MOUSE mRNA SEQUENCE (mCT8974) |
| 1995. | MOUSE PROTEIN SEQUENCE (mCP4599) |
| 1996. | HUMAN GENOMIC SEQUENCE (hCG22665) |
| 1997. | HUMAN mRNA SEQUENCE (hCT13763) |
| 1998. | HUMAN PROTEIN SEQUENCE (hCP40639) |
|  | CANCER GENE: mCG9266/hCG14925 |
| 1999. | MOUSE GENOMIC SEQUENCE (mCG9266) |
| 2000. | MOUSE mRNA SEQUENCE (mCT9256) |
| 2001. | MOUSE PROTEIN SEQUENCE (mCP10547) |
| 2002. | HUMAN GENOMIC SEQUENCE (hCG14925) |
| 2003. | HUMAN mRNA SEQUENCE (hCT5946) |
| 2004. | HUMAN PROTEIN SEQUENCE (hCP35018) |
|  | CANCER GENE: mCG9336/hCG28203 |
| 2005. | MOUSE GENOMIC SEQUENCE (mCG9336) |
| 2006. | MOUSE mRNA SEQUENCE (mCT9645) |
| 2007. | MOUSE PROTEIN SEQUENCE (mCP8121) |
| 2008. | HUMAN GENOMIC SEQUENCE (hCG28203) |
| 2009. | HUMAN mRNA SEQUENCE (hCT19351) |
| 2010. | HUMAN PROTEIN SEQUENCE (hCP43708) |
|  | CANCER GENE: mCG9393/hCG16330 |
| 2011. | MOUSE GENOMIC SEQUENCE (mCG9393) |
| 2012. | MOUSE mRNA SEQUENCE (mCT8983) |
| 2013. | MOUSE PROTEIN SEQUENCE (mCP8840) |
| 2014. | HUMAN GENOMIC SEQUENCE (hCG16330) |
| 2015. | HUMAN mRNA SEQUENCE (hCT1950491) |
| 2016. | HUMAN PROTEIN SEQUENCE (hCP1766825) |
|  | CANCER GENE: mCG9397/hCG24200 |
| 2017. | MOUSE GENOMIC SEQUENCE (mCG9397) |
| 2018. | MOUSE mRNA SEQUENCE (mCT9198) |
| 2019. | MOUSE PROTEIN SEQUENCE (mCP21072) |
| 2020. | HUMAN GENOMIC SEQUENCE (hCG24200) |
| 2021. | HUMAN mRNA SEQUENCE (hCT15314) |
| 2022. | HUMAN PROTEIN SEQUENCE (hCP41513) |
|  | CANCER GENE: mCG9437/hCG16805 |
| 2023. | MOUSE GENOMIC SEQUENCE (mCG9437) |
| 2024. | MOUSE mRNA SEQUENCE (mCT9395) |
| 2025. | MOUSE PROTEIN SEQUENCE (mCP16621) |
| 2026. | HUMAN GENOMIC SEQUENCE (hCG16805) |
| 2027. | HUMAN mRNA SEQUENCE (hCT7846) |
| 2028. | HUMAN PROTEIN SEQUENCE (hCP36061) |
|  | CANCER GENE: mCG9440/hCG401128 |
| 2029. | MOUSE GENOMIC SEQUENCE (mCG9440) |
| 2030. | MOUSE mRNA SEQUENCE (mCT9084) |
| 2031. | MOUSE PROTEIN SEQUENCE (mCP2582) |
| 2032. | HUMAN GENOMIC SEQUENCE (hCG401128) |
| 2033. | HUMAN mRNA SEQUENCE (hCT401130) |
| 2034. | HUMAN PROTEIN SEQUENCE (hCP801053) |
|  | CANCER GENE: mCG9536/hCG23831 |
| 2035. | MOUSE GENOMIC SEQUENCE (mCG9536) |
| 2036. | MOUSE mRNA SEQUENCE (mCT9701) |
| 2037. | MOUSE PROTEIN SEQUENCE (mCP9054) |
| 2038. | HUMAN GENOMIC SEQUENCE (hCG23831) |
| 2039. | HUMAN mRNA SEQUENCE (hCT14943) |
| 2040. | HUMAN PROTEIN SEQUENCE (hCP41222) |

TABLE 2-continued

IDENTIFICATION OF SEQUENCES

| SEQ ID NOS. | SEQUENCES |
|---|---|
| | CANCER GENE: mCG9597/hCG37835 |
| 2041. | MOUSE GENOMIC SEQUENCE (mCG9597) |
| 2042. | MOUSE mRNA SEQUENCE (mCT9560) |
| 2043. | MOUSE PROTEIN SEQUENCE (mCP8269) |
| 2044. | HUMAN GENOMIC SEQUENCE (hCG37835) |
| 2045. | HUMAN mRNA SEQUENCE (hCT29070) |
| 2046. | HUMAN PROTEIN SEQUENCE (hCP47769) |
| | CANCER GENE: mCG9808/hCG30268 |
| 2047. | MOUSE GENOMIC SEQUENCE (mCG9808) |
| 2048. | MOUSE mRNA SEQUENCE (mCT10254) |
| 2049. | MOUSE PROTEIN SEQUENCE (mCP12786) |
| 2050. | HUMAN GENOMIC SEQUENCE (hCG30268) |
| 2051. | HUMAN mRNA SEQUENCE (hCT21439) |
| 2052. | HUMAN PROTEIN SEQUENCE (hCP44804) |
| | CANCER GENE: mCG9960/hCG1642754 |
| 2053. | MOUSE GENOMIC SEQUENCE (mCG9960) |
| 2054. | MOUSE mRNA SEQUENCE (mCT10183) |
| 2055. | MOUSE PROTEIN SEQUENCE (mCP1922) |
| 2056. | HUMAN GENOMIC SEQUENCE (hCG1642754) |
| 2057. | HUMAN mRNA SEQUENCE (hCT1642881) |
| 2058. | HUMAN PROTEIN SEQUENCE (hCP1628404) |
| 2059. | Unknown (Cytokine receptor extracellular motif found in many species) |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07892730B2). An electronic copy of the "Sequence Listing" will also be available from the USPTO upon request and payment of the fee set forth in 37 CFR 1.19(b)(3).

We claim:

1. A method of diagnosing prostate cancer in a patient comprising:
    a) determining the level of an expression product comprising a nucleotide sequence at least 98% identical to SEQ ID NO:1175, in a patient sample comprising prostate tissue; and
    b) comparing said level of the expression product in (a) to a level of the expression product in a second sample, said second sample comprising normal prostate tissue; and
    c) diagnosing prostate cancer in said patient based on an increase of at least 50% from the level of the expression product in (a) relative to the level of the expression product in the second sample; wherein the nucleotide sequence encodes sialophorin.

2. The method of claim 1 wherein the expression product comprises SEQ ID NO:1175.

3. A method for diagnosing prostate cancer in a patient comprising detecting differential expression of sialophorin SEQ ID NO: 1175 in a patient prostate tissue sample, and diagnosing prostate cancer based on differential expression of said sialophorin.

4. The method of claim 3, wherein sialophorin gene expression in the patient sample is up-regulated relative to sialophorin gene expression in a normal control.

5. The method of claim 3 wherein evidence of differential expression is detected by measuring the level of a sialophorin gene expression product.

6. The method of claim 5 wherein the expression product is a polypeptide or mRNA.

7. The method of claim 5 wherein the expression product is a mRNA having a sequence at least 98% identical to SEQ ID NO:1175; wherein the mRNA sequence encodes sialophorin.

8. The method of claim 5 wherein the expression product is a mRNA having a sequence of SEQ ID NO:1175.

9. The method of claim 5 wherein the level of expression product in the patient sample is compared to a control.

10. The method of claim 9 wherein the control is a known normal tissue of the same tissue type as in the patient sample.

11. The method of claim 9 wherein the level of the expression product in the patient sample is increased at least 50% relative to the control.

12. The method of claim 9 wherein the level of the expression product in the patient sample is increased at least 100% relative to the control.

13. The method of claim 9 wherein the level of the expression product in the patient sample is increased at least 150% relative to the control.

14. A method of diagnosing prostate cancer comprising:
    a) determining the level of an expression product comprising a nucleotide sequence having at least 98% sequence identity to SEQ ID NO:1175, in a patient sample comprising prostate tissue;
    b) comparing said level of the expression product in (a) to a level of the expression product in a normal control; and
    c) diagnosing prostate cancer based on an increase of at least 50% from the level of the expression product in (a) relative to the level of the expression product in the normal control.

15. The method of claim 14 wherein the level of the expression product in the patient sample is increased at least 200% relative to the level of the expression product in the normal control.

16. The method of claim 14 wherein the level of the expression product in the patient sample is increased at least 100% relative to the level of the expression product in the normal control.

17. The method of claim 14 wherein the level of the expression product in the patient sample is increased at least 150% relative to the level of the expression product in the normal control.

18. The method of claim 14 wherein the expression product comprises SEQ ID NO:1175.

19. A method of diagnosing prostate cancer in a patient comprising:
   (a) contacting a polynucleotide that hybridizes under highly stringent conditions to the complement of a nucleic acid having the nucleotide sequence set forth in SEQ ID NO:1175 with nucleic acids of a patient prostate tissue sample under binding conditions suitable to form a duplex, wherein hybridization is performed at 50° C. to 60° C. in 5×SSC (9 mM saline/0.9 mM sodium citrate); and
   (b) comparing the amount of the duplex formed to the amount of duplex formed when the polynucleotide is contacted with nucleic acids of a normal, non-cancerous control, and
   (c) diagnosing said patient with prostate cancer based on increased levels of the amount of duplex formed upon contacting said polynucleotide with said nucleic acids of the patient sample compared to the amount of duplex formed upon contacting said polynucleotide and said nucleic acids of the normal non-cancerous control.

* * * * *